US011191939B2

(12) United States Patent
Funk et al.

(10) Patent No.: US 11,191,939 B2
(45) Date of Patent: Dec. 7, 2021

(54) STABILIZING CONNECTOR DEVICES FOR VASCULAR ACCESS AND METHODS OF USING THE SAME

(71) Applicant: Velano Vascular, Inc., San Francisco, CA (US)

(72) Inventors: Brian Funk, San Francisco, CA (US); Pitamber Devgon, Philadelphia, PA (US); Albert G. Burdulis, Jr., San Francisco, CA (US); Joseph W. Jackson, Jr., Wilmington, DE (US); Andrew Mazzotta, Philadelphia, PA (US); Dylan J. Paproski, North Wales, PA (US); Eric Sugalski, Berwyn, PA (US)

(73) Assignee: Velano Vascular, Inc., San Francisco, CA (US)

( * ) Notice: Subject to any disclaimer, the term of this patent is extended or adjusted under 35 U.S.C. 154(b) by 240 days.

(21) Appl. No.: 16/205,674

(22) Filed: Nov. 30, 2018

(65) Prior Publication Data

US 2019/0160275 A1    May 30, 2019

Related U.S. Application Data

(60) Provisional application No. 62/592,684, filed on Nov. 30, 2017, provisional application No. 62/631,208, filed on Feb. 15, 2018.

(51) Int. Cl.
*A61M 39/02*    (2006.01)
*A61M 5/14*    (2006.01)
(Continued)

(52) U.S. Cl.
CPC ...... *A61M 39/0247* (2013.01); *A61M 5/1418* (2013.01); *A61M 39/1011* (2013.01);
(Continued)

(58) Field of Classification Search
CPC .............. A61M 25/0606; A61M 25/02; A61M 25/0097; A61M 39/0208; A61M 39/10;
(Continued)

(56) References Cited

U.S. PATENT DOCUMENTS 4,468,224 A * 8/1984 Enzmann .............. A61M 25/06
604/168.01
4,578,063 A * 3/1986 Inman ................ A61M 39/0247
604/175

(Continued)

FOREIGN PATENT DOCUMENTS

WO    WO 2017/042359 A1    3/2017
WO    WO-2017042359 A1 *    3/2017    ........ A61M 39/1011

OTHER PUBLICATIONS

Office Action for U.S. Appl. No. 15/992,661, dated Feb. 6, 2020, 16 pgs.
(Continued)

*Primary Examiner* — Manuel A Mendez
(74) *Attorney, Agent, or Firm* — The Webb Law Firm

(57) ABSTRACT

A stabilizing connector includes a connector portion and a stabilization portion. The connector portion is configured to couple to an access device. The connector portion defines at least one lumen that is configured to be placed in fluid communication with a lumen of the access device. The stabilization portion is coupled to the connector portion. The stabilization portion is configured to be placed in contact with a surface of a patient's skin to stabilize at least one of the stabilizing connector or the access device.

18 Claims, 24 Drawing Sheets

(51) Int. Cl.
*A61M 39/10* (2006.01)
*A61M 5/158* (2006.01)

(52) U.S. Cl.
CPC ............... *A61M 2005/1586* (2013.01); *A61M 2005/1587* (2013.01); *A61M 2039/027* (2013.01); *A61M 2039/0258* (2013.01); *A61M 2039/0261* (2013.01); *A61M 2039/0273* (2013.01); *A61M 2039/0276* (2013.01); *A61M 2039/0285* (2013.01); *A61M 2039/1033* (2013.01); *A61M 2209/088* (2013.01)

(58) Field of Classification Search
CPC .......... A61M 39/0247; A61M 25/0662; A61M 39/1011; A61B 17/0057
See application file for complete search history.

(56) References Cited

U.S. PATENT DOCUMENTS

| | | | |
|---|---|---|---|
| 5,336,195 | A | 8/1994 | Daneshvar |
| 5,556,381 | A | 9/1996 | Ensiminger et al. |
| 5,681,290 | A | 10/1997 | Alexander |
| 5,693,032 | A | 12/1997 | Bierman |
| 5,755,225 | A | 5/1998 | Hutson |
| 5,807,342 | A | 9/1998 | Musgrave et al. |
| 5,810,781 | A | 9/1998 | Bierman et al. |
| 5,833,666 | A | 11/1998 | Davis et al. |
| 6,086,564 | A | 7/2000 | Mclaughlin |
| 6,213,979 | B1 | 4/2001 | Bierman |
| 6,283,945 | B1 | 9/2001 | Bierman |
| 6,332,874 | B1 | 12/2001 | Eliasen et al. |
| 6,361,523 | B1 | 3/2002 | Bierman |
| 6,413,240 | B1 | 7/2002 | Bierman et al. |
| 6,418,966 | B2 | 7/2002 | Loo |
| 6,428,513 | B1 | 8/2002 | Abrahamson |
| 6,551,284 | B1 | 4/2003 | Greenberg et al. |
| 6,663,600 | B2 | 12/2003 | Bierman et al. |
| 6,929,625 | B2 | 8/2005 | Bierman |
| 6,951,550 | B2 | 10/2005 | Bierman |
| 7,014,627 | B2 * | 3/2006 | Bierman ................ A61M 25/02 604/174 |
| 7,018,362 | B2 | 3/2006 | Bierman et al. |
| 7,198,616 | B2 | 4/2007 | Mossanen-Shams et al. |
| 7,223,256 | B2 | 5/2007 | Bierman |
| 7,247,150 | B2 | 7/2007 | Bierman |
| 7,563,251 | B2 | 7/2009 | Bierman et al. |
| 7,591,803 | B2 | 9/2009 | Bierman |
| 7,594,910 | B2 | 9/2009 | Butts et al. |
| 7,635,355 | B2 | 12/2009 | Bierman |
| 7,722,571 | B2 | 5/2010 | Bierman et al. |
| 7,785,295 | B2 | 8/2010 | Bierman |
| 7,879,013 | B2 | 2/2011 | Smith et al. |
| 7,981,087 | B2 | 7/2011 | Gesler |
| 8,016,793 | B2 | 9/2011 | Wright et al. |
| 8,025,643 | B2 | 9/2011 | Bierman |
| 8,029,476 | B2 | 10/2011 | Rosenberg et al. |
| 8,052,648 | B2 | 11/2011 | Dikeman et al. |
| 8,052,649 | B2 | 11/2011 | Wright |
| 8,083,723 | B2 | 12/2011 | Glenn |
| 8,105,289 | B2 | 1/2012 | Bierman et al. |
| 8,105,290 | B2 | 1/2012 | Wright et al. |
| 8,114,054 | B2 | 2/2012 | Bierman et al. |
| 8,137,323 | B2 | 3/2012 | Rosenberg et al. |
| 8,177,756 | B2 | 5/2012 | Wright |
| 8,241,253 | B2 | 8/2012 | Bracken |
| 8,246,583 | B2 | 8/2012 | Bierman |
| 8,337,461 | B2 | 12/2012 | Burkholz |
| 8,394,066 | B2 | 3/2013 | Rosenberg et al. |
| 8,398,599 | B2 | 3/2013 | Bierman |
| 8,425,476 | B2 | 4/2013 | Glenn |
| 8,506,533 | B2 | 8/2013 | Carlyon et al. |
| 8,585,655 | B2 | 11/2013 | Bierman |
| 8,622,972 | B2 | 1/2014 | Nystroem et al. |
| 8,636,698 | B2 | 1/2014 | Bierman et al. |
| 8,657,791 | B2 | 2/2014 | Bierman et al. |
| 8,795,237 | B2 | 8/2014 | Vitaris et al. |
| 8,915,885 | B2 | 12/2014 | Smith et al. |
| 8,915,891 | B2 | 12/2014 | Bornhoft |
| 8,932,263 | B2 | 1/2015 | Rosenberg et al. |
| 8,979,805 | B1 | 3/2015 | Khalaj |
| 9,056,186 | B2 | 6/2015 | Wright et al. |
| 9,061,122 | B2 | 6/2015 | Bierman et al. |
| 9,314,596 | B2 | 4/2016 | Rosenberg et al. |
| 9,333,323 | B2 | 5/2016 | Racz et al. |
| 9,408,569 | B2 | 8/2016 | Andreae et al. |
| 9,433,754 | B2 | 9/2016 | Mogg |
| 9,480,821 | B2 | 11/2016 | Ciccone et al. |
| 9,486,613 | B2 | 11/2016 | Dickert et al. |
| 9,526,869 | B2 | 12/2016 | Beran |
| 9,545,502 | B2 | 1/2017 | Maseda et al. |
| 9,550,043 | B2 | 1/2017 | Rosenberg et al. |
| 9,550,044 | B2 | 1/2017 | Maseda et al. |
| 9,782,567 | B2 | 10/2017 | Rosenberg et al. |
| 10,105,085 | B2 | 10/2018 | Andreae et al. |
| 10,357,636 | B2 | 7/2019 | Sonderegger et al. |
| 10,426,929 | B2 | 10/2019 | Burkholz et al. |
| 2005/0131351 | A1 | 6/2005 | Bierman |
| 2006/0084922 | A1 | 4/2006 | Botha |
| 2006/0217669 | A1 | 9/2006 | Botha |
| 2006/0270994 | A1 | 11/2006 | Bierman |
| 2007/0066958 | A1 | 3/2007 | Wright |
| 2007/0142782 | A2 | 6/2007 | Bierman |
| 2007/0149930 | A1 | 6/2007 | Bierman |
| 2008/0125718 | A1 | 5/2008 | Tsuchiya et al. |
| 2008/0200880 | A1 | 8/2008 | Kyvik |
| 2009/0149814 | A1 | 6/2009 | Bailey |
| 2010/0100049 | A1 | 4/2010 | Godfrey |
| 2010/0179481 | A1 | 7/2010 | Bierman et al. |
| 2010/0179563 | A1 | 7/2010 | Skakoon et al. |
| 2010/0298777 | A1 | 11/2010 | Nishtala |
| 2011/0213310 | A1 | 9/2011 | Bierman |
| 2011/0282291 | A1 | 11/2011 | Ciccone |
| 2012/0016312 | A1 | 1/2012 | Brown et al. |
| 2012/0041377 | A1 | 2/2012 | Haak et al. |
| 2012/0059328 | A1 | 3/2012 | Dikeman et al. |
| 2012/0136314 | A1 | 5/2012 | Ciccone et al. |
| 2012/0197205 | A1 | 8/2012 | Peters |
| 2012/0232490 | A1 | 9/2012 | Andino |
| 2012/0271240 | A1 | 10/2012 | Andino et al. |
| 2013/0053785 | A1 | 2/2013 | Parvatiyar et al. |
| 2013/0138045 | A1 | 5/2013 | Bierman |
| 2014/0061408 | A1 | 3/2014 | Heinecke et al. |
| 2014/0200517 | A1 | 7/2014 | Humphries et al. |
| 2014/0343531 | A1 | 11/2014 | Larkin |
| 2014/0364766 | A1 * | 12/2014 | Devgon ........... A61B 5/150221 600/581 |
| 2015/0112270 | A1 | 4/2015 | Smith et al. |
| 2015/0119845 | A1 | 4/2015 | Collins et al. |
| 2015/0141962 | A1 | 5/2015 | Collins et al. |
| 2015/0217088 | A1 | 8/2015 | Zyzelewski et al. |
| 2015/0224286 | A1 | 8/2015 | Teh et al. |
| 2015/0367102 | A1 | 12/2015 | Andino et al. |
| 2016/0015932 | A1 | 1/2016 | Catudal |
| 2016/0184554 | A1 | 6/2016 | Rosenberg et al. |
| 2016/0354580 | A1 | 12/2016 | Teoh et al. |
| 2016/0367789 | A1 | 12/2016 | Beran |
| 2017/0043130 | A1 | 2/2017 | Jones et al. |
| 2017/0080187 | A1 | 3/2017 | Maseda et al. |
| 2017/0274182 | A1 | 9/2017 | O'Bryan et al. |
| 2017/0368312 | A1 | 12/2017 | Rosenberg et al. |
| 2018/0001059 | A1 | 1/2018 | Rosenberg et al. |
| 2018/0161543 | A1 | 6/2018 | Burkholz |
| 2018/0289921 | A1 | 10/2018 | Burkholz |
| 2018/0289922 | A1 | 10/2018 | Burkholz |
| 2018/0339132 | A1 * | 11/2018 | Brunetti ............. A61M 39/1011 |
| 2018/0344983 | A1 * | 12/2018 | Funk ................. A61M 25/0097 |

(56) References Cited

U.S. PATENT DOCUMENTS

2020/0023166 A1    1/2020   Burkholz et al.
2020/0078565 A1    3/2020   Scherich et al.

OTHER PUBLICATIONS

International Search Report and Written Opinion for International Application No. PCT/US2018/035065, dated Oct. 22, 2018, 10 pgs.
International Search Report and Written Opinion for International Application No. PCT/US2018/63262, dated Feb. 15, 2019, 11 pgs.

* cited by examiner

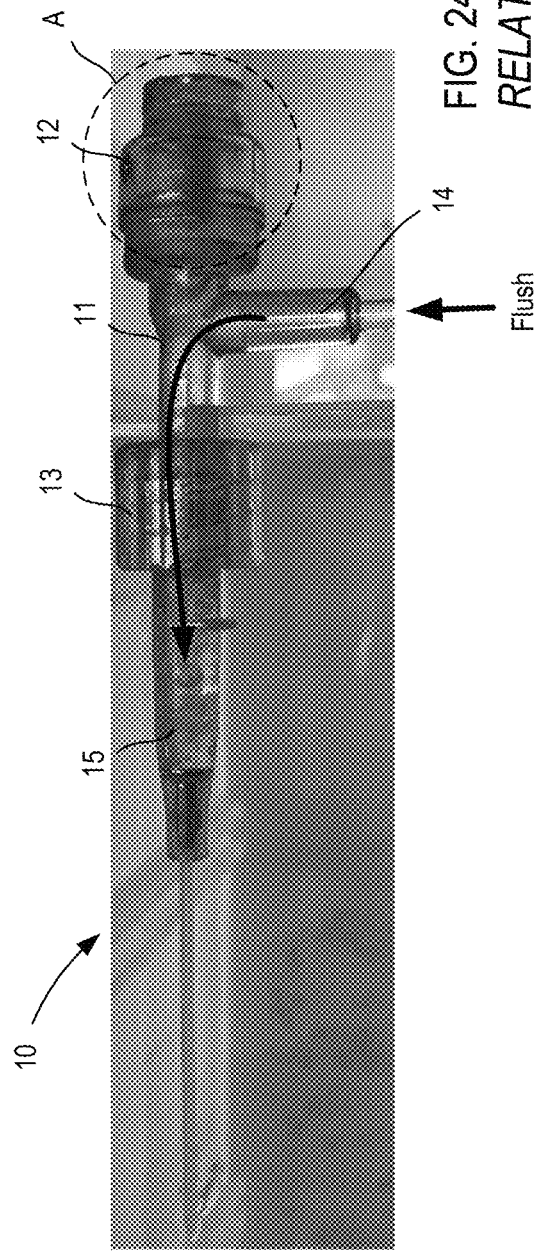
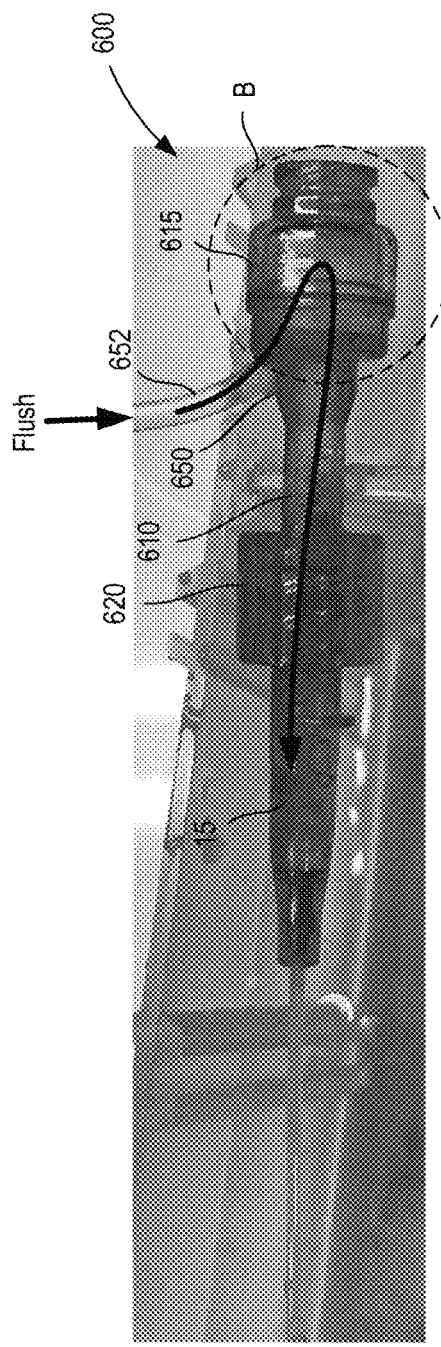
FIG. 24
RELATED ART
FIG. 25

STABILIZING CONNECTOR DEVICES FOR VASCULAR ACCESS AND METHODS OF USING THE SAME

CROSS-REFERENCE TO RELATED APPLICATIONS

This application claims priority to and the benefit of U.S. Provisional Patent Application Ser. No. 62/592,684 entitled, "Stabilizing Connector Devices for Vascular Access and Methods of Using the Same," filed Nov. 30, 2017, the disclosure of which is incorporated herein by reference in its entirety.

This application also claims priority to and the benefit of U.S. Provisional Patent Application Ser. No. 62/631,208 entitled, "Stabilizing Connector Devices for Vascular Access and Methods of Using the Same," filed Feb. 15, 2018, the disclosure of which is incorporated herein by reference in its entirety.

BACKGROUND

The embodiments described herein relate generally to medical devices and, more particularly, to devices and methods for connecting and/or stabilizing vascular access devices such as intravenous catheters and/or devices coupled thereto.

Many medical procedures and/or surgical interventions include inserting an access device or fluid transfer device into a portion of the body. For example, catheters and/or other lumen-defining devices can be inserted into and/or through vascular structures to access portions of the body and/or to transfer fluids from and/or to a patient. In some instances, vascular access devices (VADs) such as, for example, peripheral intravenous catheters (PIVs), are inserted into patients (e.g., when a patient is hospitalized or during other medical procedures) and are designed and/or intended to remain within the patient for an extended period.

VADs typically include a catheter formed from a soft bio-reactive polymer that is partially disposed in the body and that is attached, at a proximal end (e.g., the end outside of the body) to a hub, which in turn, can provide an interface, coupler, and/or port for attaching any suitable device. After placing the VAD (e.g., a PIV catheter or the like) within a vein (or artery) of the patient, it is often desirable to stabilize and/or secure the VAD relative to the patient. For example, in some instances, movement of the VAD relative to the patient can result in undesirable bending, flexing, and/or kinking of the catheter. In other instances, movement of the VAD (e.g., along a longitudinal axis of the VAD) can withdraw a portion of the catheter from the patient's body, which in turn, can expose that portion of the catheter to an unsterile environment. Moreover, moving the VAD back to its original position can result in the potentially contaminated portion of the VAD (e.g., the catheter) being inserted back in the patient, thereby increasing the chances of infection.

Stabilizing and/or securing devices are often used in an effort to minimize movement of a placed or indwelling VAD (e.g., a PIV catheter). Some known stabilizing and/or securing devices, however, are complicated and/or time consuming to use, while others may provide inadequate stabilization. In addition, the shape and/or configuration of some known stabilizing and/or securing devices can negatively affect a flow rate through a portion the VAD and/or the vein (or artery) in which the catheter is disposed. Moreover, VADs are often used with an intermediate device or connector such as, for example, an extension set. In such instances, adding a stabilization device increases the complexity and/or cost of the procedure sought to be performed. In addition, some such stabilization devices are designed for use with a specific VAD and/or a specific extension set.

Thus, a need exists for improved devices and methods for connecting to and/or stabilizing placed vascular access devices.

SUMMARY

Devices and methods for stabilizing or otherwise using placed or indwelling vascular access devices such as, for example, intravenous or arterial catheters are described herein. In some embodiments, an apparatus includes a connector portion and a stabilization portion integrally formed with at least a part of the connector portion. The connector portion has a distal coupler and a proximal coupler and defines a lumen extending between the distal coupler and the proximal coupler. The distal coupler is configured to be coupled to a hub of an access device inserted, at least in part, into a patient at a predetermined angle relative to an insertion site of the patient such that the lumen of the connector portion is placed in fluid communication with a lumen defined by the access device. The stabilization portion is configured to be in contact with the patient when the distal coupler is coupled to the hub of the access device to stabilize at least one of the connector portion or the access device. The connector portion is disposed at about the predetermined angle when the stabilization portion is in contact with the patient such that a common axis extends through the lumen defined by the connector portion and at least a portion of the lumen defined by the access device.

BRIEF DESCRIPTION OF THE DRAWINGS

FIG. 24 is a side view of a known dual port connector or extension set coupled to an access device such as, for example, an intravenous catheter.

FIG. 25 is a side view of a dual port connector or extension set coupled to an access device such as, for example, an intravenous catheter, according to an embodiment.

DETAILED DESCRIPTION

Figure 1:
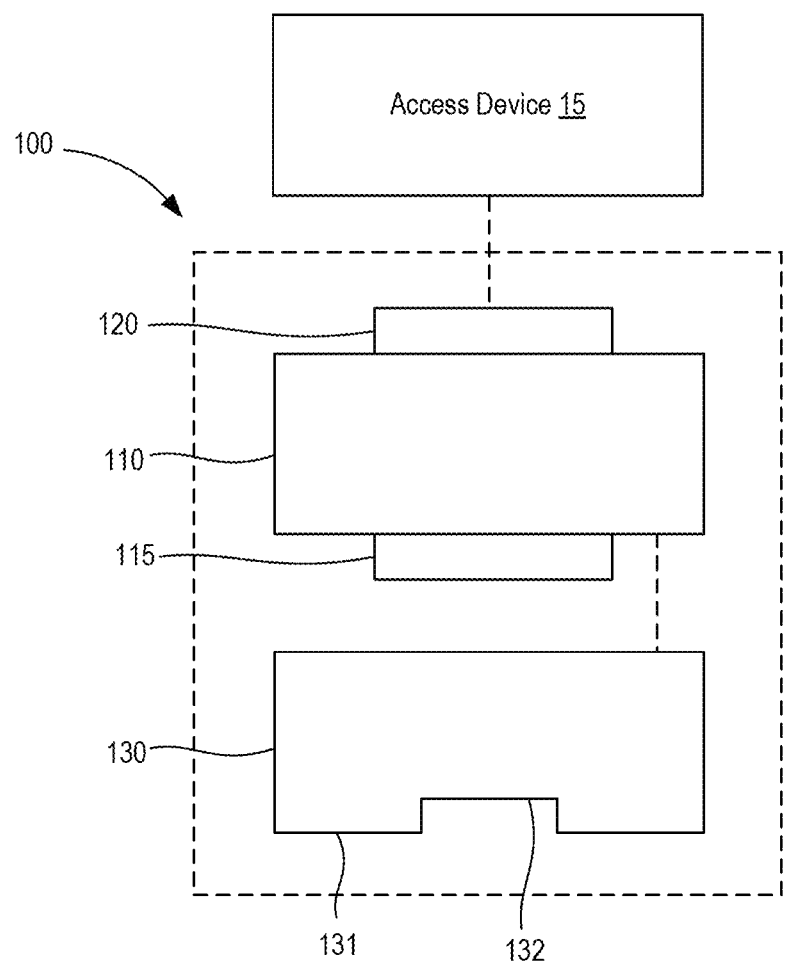
FIG. 1 is a schematic illustration of a stabilizing connector according to an embodiment.
Figure 2:
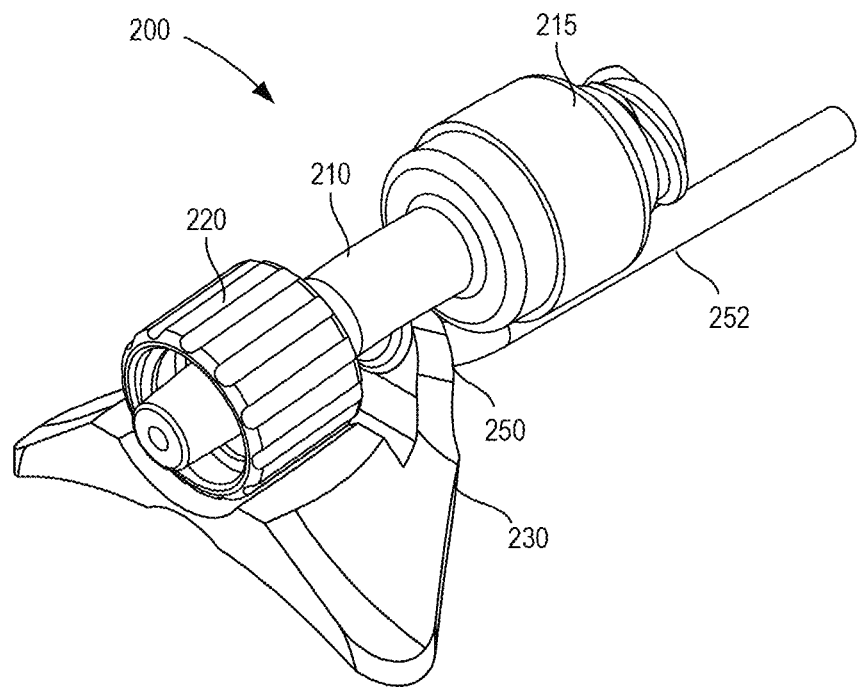
FIGS. 2 and 3 are a perspective view and a side view, respectively, of a stabilizing connector according to an embodiment.
Figure 3:
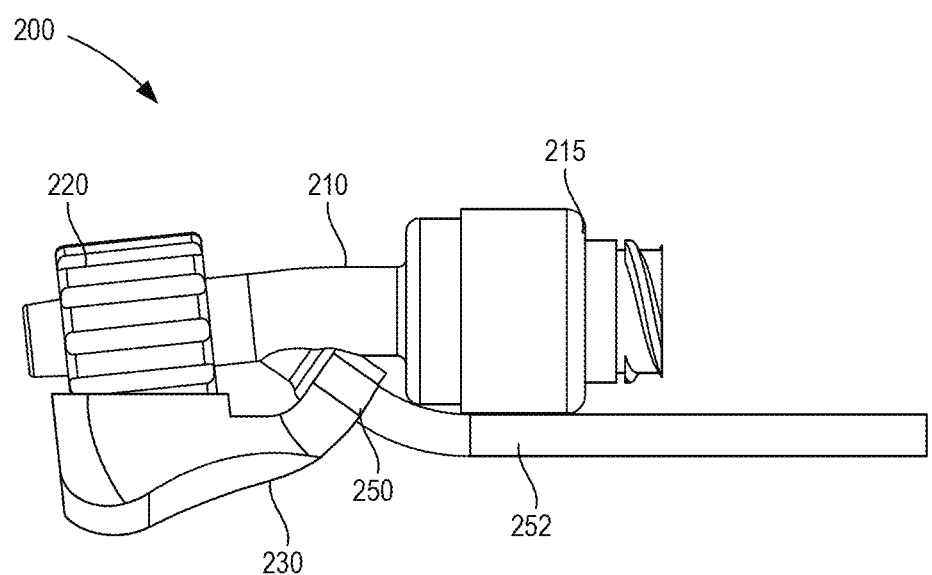
Figure 4:
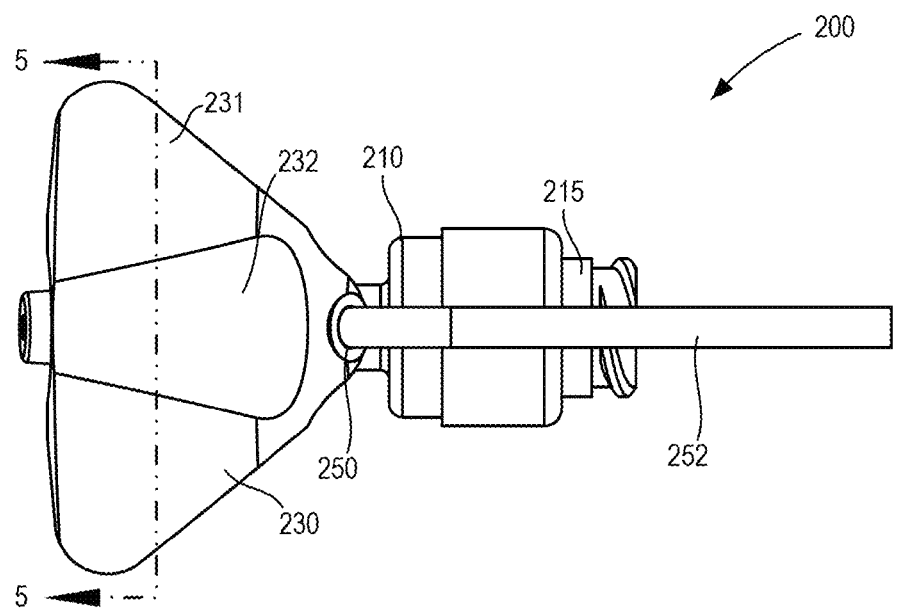
FIG. 4 is a bottom view of the stabilizing connector of FIG. 2.
Figure 5:
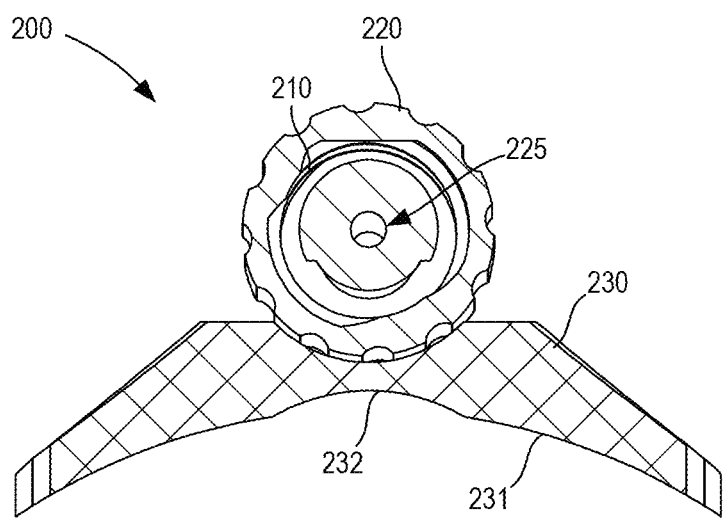
FIG. 5 is a cross-sectional view of the stabilizing connector taken along the line 5-5 in FIG. 4.
Figure 6:
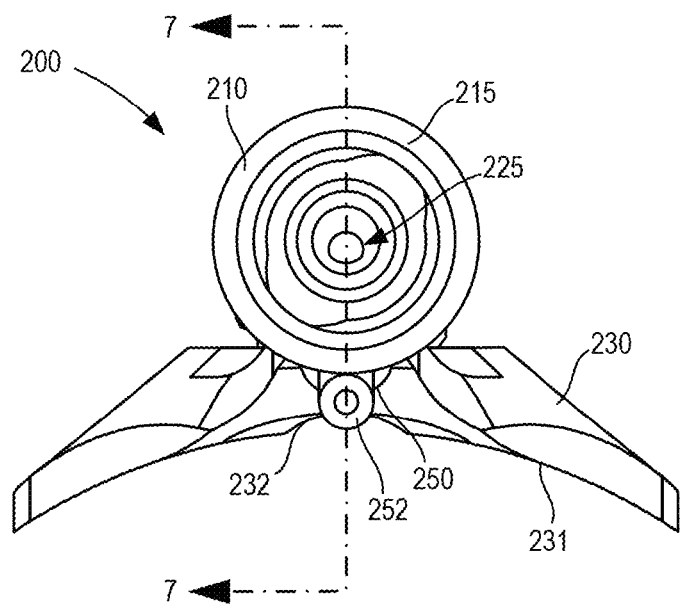
FIG. 6 is a rear view of the stabilizing connector of FIG. 2.

In some embodiments, an apparatus includes a connector portion and a stabilization portion integrally formed with at least a part of the connector portion. The connector portion has a distal coupler and a proximal coupler and defines a lumen extending between the distal coupler and the proximal coupler. The distal coupler is configured to be coupled to a hub of an access device inserted, at least in part, into a patient at a predetermined angle relative to an insertion site of the patient such that the lumen of the connector portion is placed in fluid communication with a lumen defined by the access device. The stabilization portion is configured to be in contact with the patient when the distal coupler is coupled to the hub of the access device to stabilize at least one of the connector portion or the access device. The connector portion is disposed at about the predetermined angle when the stabilization portion is in contact with the patient such that a common axis extends through the lumen defined by the connector portion and at least a portion of the lumen defined by the access device.

In some embodiments, an apparatus includes a connector portion and a stabilization portion integrally formed with at least a part of the connector portion. The connector portion has a distal coupler and a proximal coupler and defines a lumen extending between the distal coupler and the proximal coupler. The distal coupler is configured to be coupled to a hub of an access device at least partially inserted into a vein of a patient such that the lumen of the connector portion is placed in fluid communication with a lumen defined by the access device. The stabilization portion has a base surface. A portion of the base surface is configured to be in contact with the patient when the distal coupler is coupled to the hub of the access device such that (1) the stabilization portion stabilizes at least one of the connector portion or the access device and (2) a common axis extends through the lumen defined by the connector portion and at least a portion of the lumen defined by the access device. The base surface forms a recess configured to be aligned with the vein and spaced apart from the patient when the portion of the base surface is in contact with the patient.

In some embodiments, an apparatus includes a connector portion and a stabilization portion integrally formed with at least a part of the connector portion. The connector portion has a distal coupler and a proximal coupler and defines a lumen extending between the distal coupler and the proximal coupler. The distal coupler is configured to be coupled to a hub of an access device at least partially inserted into a patient such that the lumen of the connector portion is in fluid communication with a lumen defined by the access device. The stabilization portion has a base surface. A portion of the base surface is configured to be in contact with the patient when the distal coupler is coupled to the hub of the access device to stabilize at least one of the connector portion or the access device. The base surface forms a recess configured to be spaced apart from the patient when the portion of the base surface is in contact with the patient. The connector portion is disposed at a predetermined angle when the distal coupler is coupled to the hub of the access device and the base surface is in contact with the patient such that a common axis extends through the lumen defined by the connector portion and at least a portion of the lumen defined by the access device.

In some embodiments, a stabilizing connector includes a connector portion and a stabilization portion. The connector portion is configured to couple to an access device. The connector portion defines at least one lumen that is configured to be placed in fluid communication with a lumen of the access device. The stabilization portion is coupled to the connector portion. The stabilization portion is configured to be placed in contact with a surface of a patient's skin to stabilize at least one of the stabilizing connector or the access device.

As used in this specification, the singular forms "a," "an," and "the" include plural referents unless the context clearly dictates otherwise. Thus, for example, the term "a member" is intended to mean a single member or a combination of members, "a material" is intended to mean one or more materials or a combination thereof, "a device" is intended to mean a single device or a combination of devices.

The devices and methods described herein are configured to stabilize devices and/or components of devices that are directly or indirectly inserted in a patient. Such devices are generally referred to herein as access devices. The devices and/or methods described herein can be used with any suitable access device that allows access to any portion of a patient. Though the devices and methods are not intended to be limited to use with a particular access device, a specific example of such a device is/are vascular access device(s) (VADs). Non-limiting examples of a VAD can include intravenous (IV) access devices such as peripheral intravenous catheters (M), peripheral intravenous central catheters (PICCs or PIC lines), midline catheters, extended dwell catheters (EDCs), etc. In other embodiments, a VAD can be an intra-arterial access device such as an arterial line, and/or the like. While reference to use with specific access devices is made herein, it should be understood that such reference is presented by way of example and not limitation.

As used herein, the term "catheter" describes an element configured to define a passageway such as a cannula, a tube, and/or other lumen-defining structure. In some instances, a catheter can be used for moving a bodily fluid from a first location to a second location (e.g., a fluid passageway to move a bodily fluid out of the body). While cannulas can be configured to receive a trocar, a guide wire, and/or an introducer to deliver the cannula to a volume inside the body of a patient, the catheters and/or cannulas referred to herein need not include or receive a trocar, guide wire, and/or introducer and can be positioned and/or inserted into, for example, the vasculature of a patient using any suitable method. Moreover, references to catheters herein is provided by way of example only and not limitation. Accordingly, describing a lumen-defining structure as a "catheter" is not intended to preclude the use of any other suitable lumen-defining structure where desirable.

As used in this specification, the term "extension set" generally refers to a device or connector that is coupled to a hub of a VAD such as a peripheral IV catheter or the like. The "extension sets" can be any suitable configuration. For example, in some embodiments, an extension set can be a single port or a multi-port connector. As a specific example, an extension set can be and/or can refer to a "Y-shaped" dual port extension. In other embodiments, an extension set can be and/or can refer to a "T-shaped" dual port extension set. In still other embodiments, an extension set can be and/or can refer to single port extension set (i.e., an extension set defining a single lumen therethrough). In general, some known extension sets are configured to couple between a hub of a VAD and any suitable medical device and can allow one or more objects, devices, medicaments, fluids, etc. to access a portion of the body of a patient (e.g., via the VAD). More particularly, in some instances, an extension set can be coupled to an indwelling access device (e.g., a PIV or the like) to facilitate the transfer and/or collection of one of more fluids. In some instances, the fluid can be a bodily fluid including, but not limited to, blood, cerebrospinal fluid, urine, bile, lymph, saliva, synovial fluid, serous fluid, pleural fluid, amniotic fluid, mucus, vitreous, air, and the like, or any combination thereof.

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

FIG. 1 illustrates a stabilizing connector 100 according to an embodiment. The stabilizing connector 100 is configured to be placed in contact with the skin of a patient at or near an insertion site of an indwelling or placed vascular access device (VAD) such as those described above. The stabilizing connector 100 is configured to couple to and/or otherwise engage the VAD. Once coupled to the VAD, the stabilizing connector 100 can be secured to the skin of the patient (e.g., via medical tape, a clear sterile barrier such as Tegaderm™, and/or the like), which in turn, secures and/or stabilizes at least a portion of the VAD relative to the patient, as described in further detail herein.

The stabilizing connector 100 can be any suitable shape, size, and/or configuration. For example, as shown, the stabilizing connector 100 (also referred to herein as "connector") has a connector portion 110 and a stabilization portion 130. In some embodiments, the connector 100 can be configured as a combination of one or more stabilization device(s) and an extension set. Each of the connector portion 110 and/or the stabilization portion 130 can be arranged in any suitable manner to facilitate at least one of the functions of providing stabilization to one or more devices (e.g., a VAD or the like) and/or at least one of the functions of providing an extension set for use with a VAD.

The connector portion 110 can have any suitable shape, size, and/or configuration. For example, in some embodiments, the connector portion 110 can be and/or can form a single port or dual port adapter or extension set configured to be used with and/or coupled to, for example, an access device 15. As shown in FIG. 1, the connector portion 110 has a proximal coupler 115 and a distal coupler 120 and defines at least one lumen (not shown in FIG. 1) extending through or otherwise in fluid communication with the couplers 115 and 120. The proximal coupler 115 and/or the distal coupler 120 can be, for example, male or female luer locks, needle-free connectors (NFCs), and/or any other suitable coupler or combination of couplers. As described in further detail herein, the proximal coupler 115 can be physically and fluidically coupled to any suitable medical device. The distal coupler 120 can be physically and fluidically coupled to, for example, the access device 15 such as a VAD, a PIV, a PICC line, an arterial IV, and/or the like such that the lumen of the connector portion 110 is at least selectively in fluid communication with the access device 15 and/or a portion of the body in which the access device 15 is at least partially disposed. In some embodiments, the lumen of the connector portion 110 can be substantially straight and/or can allow for a substantially straight line of sight therethrough (e.g., at least between the proximal coupler 115 and the distal coupler 120).

Although not shown in FIG. 1, in some embodiments, the connector portion 110 can include one or more additional ports (e.g., one or more side ports or the like). In some such instances, the port can define a lumen that is in fluid communication with the lumen extending between the proximal connector 115 and the distal connector 120. In other words, the connector portion 110 and/or the port can include and/or define a first lumen and a second lumen. As such, the port can provide access to the lumen extending between the couplers 115 and 120, which in turn, can provide access, via the distal coupler 120, to the access device 15 coupled thereto and/or can provide access to a portion of the body in which the access device 15. Moreover, the port can be coupled to tubing or the like configured to establish fluid communication between the port and one or more devices, mechanisms, reservoirs, pumps, syringes, etc. coupled to an end portion of the tubing, as described in further detail herein with reference to specific embodiments.

The stabilization portion 130 is coupled to the connector portion 110 and is configured to be placed in contact with a portion of a patient (e.g., the skin of the patient) at or near an insertion site associated with the access device 15. The stabilization portion 130 can be any suitable shape, size, and/or configuration. For example, in some embodiments, the stabilization portion 130 can be and/or can form a base structure that is angled, tapered, flared, curved, rounded, and/or the like. In some embodiments, the stabilization portion 130 can have a contour and/or shape that is generally concave. In some embodiments, the concave contour and/or shape can be based at least in part on a curvature and/or shape of a portion of the patient's anatomy. In some embodiments, forming the contour and/or shape of the stabilization portion 130 to be similar to and/or at least partially based on the curvature and/or angle of an IV insertion site of the patient, for example, can increase a surface area of the stabilization portion 130 that is in contact with the skin of the patient, which in turn, can increase the stability of the stabilizing connector 100, and reduce a pressure associated with securing the stabilizing connector 100 to the skin of the patient, as described in further detail herein. Moreover, in some embodiments, a base surface 131 of the stabilization portion 130 can include one or more contours, recess, notches, cutouts, etc. (referred to herein as "recess" 132) configured to reduce an amount of force exerted by a portion of the stabilization portion 130 on or more veins of the patient (e.g., the vein in which the access device 15 is disposed), which might otherwise result in an occlusion of and/or a reduced flow rate through at least a portion of the vein.

In some embodiments, the base surface 131 of the stabilization portion 130 can be selectively formed of one or more materials (e.g., a relatively hard material and/or a relatively soft material) configured to provide both stabilization and comfort. In some embodiments, the stabilization portion 130 can be configured to provide increased stabilization to a given or desired portion (e.g., a proximal portion, a distal portion, one or more side portions, and/or the like) thereof. In some embodiments, the stabilization portion 130 can be reconfigurable, which can allow a user to selectively control an amount of stabilization provided by the stabilization portion 130. Moreover, in some such embodiments, a user can reconfigure (e.g., bend, flex, deform, conform, stretch, break, cut, add to, etc.) one or more portions of the stabilization portion 130 to, for example, control an amount or manner of stabilization, conform at least a portion of the stabilization portion 130 to the contours of a specific patient, reduce or substantially prevent pressure points, and/or the like.

The stabilization portion 130 is configured to be placed in contact with a portion of the patient's skin at or near the insertion site (as described above). In addition, the stabilization portion 130 and/or the stabilizing connector 100 in general, is configured to be secured to the skin of the patient using any suitable securement means. For example, in some instances, the stabilization portion 130 can be taped to the skin of the patient using medical tape or the like or the base surface 131 can include and/or can be coated with an adhesive configured to secure the connector 100 to the patient. In other instances, the stabilization portion 130 can be secured to the skin of the patient using a clear sterile barrier such as, for example, Tegaderm™. In still other embodiments, the stabilization portion 130 can be secured to the skin of the patient using any suitable combination of securement methods (e.g., any combination of the methods described herein). In some embodiments, the size, shape, and/or configuration of at least the stabilization portion 130 can facilitate the securement of the stabilizing connector 100 to the skin of the patient. For example, in some embodiments, the stabilization portion 130 can be configured such that at least a portion of a clear sterile barrier (e.g., Tegaderm™) can wrap around the stabilization portion 130 such that the stabilization portion 130 is disposed within or under the barrier. In some instances, configuring the stabilization portion 130 to allow for the barrier to surround the stabilization portion 130 can, for example, reduce and/or substantially prevent openings in the barrier that may otherwise result in points of contamination or the like.

FIGS. 2-7 illustrate a stabilizing connector 200 according to an embodiment. The stabilizing connector 200 is configured to be placed in contact with the skin of a patient at or near an insertion site of an indwelling or placed vascular access device (VAD) such as those described above. The stabilizing connector 200 is configured to couple to and/or otherwise engage the VAD. Once coupled to the VAD, the stabilizing connector 200 can be secured to the skin of the patient (e.g., via medical tape, a clear sterile barrier such as Tegaderm™, and/or the like), which in turn, secures and/or stabilizes at least a portion of the VAD relative to the patient, as described in further detail herein.

The stabilizing connector 200 can be any suitable shape, size, and/or configuration. For example, as shown, the stabilizing connector 200 (also referred to herein as "connector") has a connector portion 210 and a stabilization portion 230. In some embodiments, the connector 200 can be configured as a combination of one or more stabilization device(s) and an extension set. Each of the connector portion 210 and/or the stabilization portion 230 can be arranged in any suitable manner to facilitate at least one of the functions of providing stabilization to one or more devices (e.g., a VAD or the like) and/or at least one of the functions of providing an extension set for use with a VAD.

The connector portion 210 has a proximal coupler 215 and a distal coupler 220 and defines at least one lumen 225 extending through or otherwise in fluid communication with the couplers 215 and 220. The proximal coupler 215 and/or the distal coupler 220 can be, for example, male or female luer locks, needle-free connectors (NFCs), and/or any other suitable coupler or combination of couplers. As described in further detail herein, the proximal coupler 215 can be physically and fluidically coupled to any suitable medical device. The distal coupler 220 can be physically and fluidically coupled to, for example, a VAD or the like such that the lumen 225 of the connector portion 210 is at least selectively in fluid communication with the VAD and/or a portion of the body in which the VAD is at least partially disposed. In some embodiments, the lumen 225 of the connector portion 210 can be substantially straight and/or can allow for a substantially straight line of sight therethrough (e.g., at least between the proximal coupler 215 and the distal coupler 220).

The stabilization portion 230 is coupled to the connector portion 210 and is configured to be placed in contact with a portion of a patient (e.g., the skin of the patient) at or near an insertion site associated with the VAD (or other similar device). The stabilization portion 230 can be any suitable shape, size, and/or configuration. For example, in some embodiments, the stabilization portion 230 can be and/or can form a base structure that is angled, tapered, flared, curved, rounded, and/or the like. In some embodiments, the stabilization portion 230 can have a contour and/or shape that is generally concave. In some embodiments, the concave contour and/or shape can be based at least in part on a curvature and/or shape of a portion of the patient's anatomy. In some embodiments, forming the contour and/or shape of the stabilization portion 230 to be similar to and/or at least partially based on the curvature and/or angle of an IV insertion site of the patient, for example, can increase a surface area of the stabilization portion 230 that is in contact with the skin of the patient, which in turn, can increase the stability of the stabilizing connector 200, and reduce a pressure associated with securing the stabilizing connector 200 to the skin of the patient, as described in further detail herein. Moreover, in some embodiments, a base surface 231 of the stabilization portion 230 can include one or more contours, recess, notches, cutouts, etc. (referred to herein as a "recess" 232 (see e.g., FIGS. 4-6)) configured to reduce an amount of force exerted by a portion of the stabilization portion 230 on or more veins of the patient (e.g., the vein in which the VAD is disposed), which might otherwise result in an occlusion of and/or a reduced flow rate through at least a portion of the vein.

In some embodiments, the base surface 231 of the stabilization portion 230 can be selectively formed of one or more materials (e.g., a relatively hard material and/or a relatively soft material) configured to provide both stabilization and comfort. In some embodiments, the stabilization portion 230 can be configured to provide increased stabilization to a given or desired portion (e.g., a proximal portion, a distal portion, one or more side portions, and/or the like). In some embodiments, the stabilization portion 230 can be reconfigurable, which can allow a user to selectively control an amount of stabilization provided by the stabilization portion 230. Moreover, in some such embodiments, a user can reconfigure (e.g., bend, flex, deform, conform, stretch, break, cut, add to, etc.) one or more portions of the stabilization portion 230 to, for example, control an amount or manner of stabilization, conform at least a portion of the stabilization portion 230 to the contours of a specific patient, reduce or substantially prevent pressure points, and/or the like.

The stabilization portion 230 is configured to be placed in contact with a portion of the patient's skin at or near the insertion site (as described above). In addition, the stabilization portion 230 and/or the stabilizing connector 200 in general, is configured to be secured to the skin of the patient using any suitable securement means. For example, in some instances, the stabilization portion 230 can be taped to the skin of the patient using medical tape or the like or the base surface 231 can include and/or can be coated with an adhesive configured to secure the connector 200 to the patient. In other instances, the stabilization portion 230 can be secured to the skin of the patient using a clear sterile barrier such as, for example, Tegaderm™. In still other embodiments, the stabilization portion 230 can be secured to the skin of the patient using any suitable combination of securement methods (e.g., any combination of the methods described herein). In some embodiments, the size, shape, and/or configuration of at least the stabilization portion 230 can facilitate the securement of the stabilizing connector 200 to the skin of the patient. For example, in some embodiments, the stabilization portion 230 can be configured such that at least a portion of a clear sterile barrier (e.g., Tegaderm™) can wrap around the stabilization portion 230 such that the stabilization portion 230 is disposed within or under the barrier. In some instances, configuring the stabilization portion 230 to allow for the barrier to surround the stabilization portion 230 can, for example, reduce and/or substantially prevent openings in the barrier that may otherwise result in points of contamination or the like.

The connector 200 also includes a port 250. The port 250 can be included in and/or can be a part of the connector portion 210, the stabilization portion 230, and/or a combination thereof. As shown, the port 250 can define a lumen 255 that is in fluid communication with the lumen 225. In other words, the connector portion 210 and/or the port 250 can include and/or define a first lumen (e.g., the lumen 225) and a second lumen (e.g., the lumen 255), as shown, for example, in FIG. 7. As such, the port 250 can provide access to the lumen 225, which in turn, can provide access, via the distal coupler 220, to a device (e.g., a VAD) coupled thereto and/or can provide access to a portion of the body in which the VAD is at least partially disposed. As shown in FIGS. 2-7, the port 250 is coupled to tubing 252 that is in fluid communication with the lumen 255 of the port 250.

Although not shown in FIGS. 2-7, an end portion of the tubing 252 (e.g., an end portion opposite the port 250) can include and/or can be coupled to a connector, a port, a coupler, a luer lock, and/or any suitable flow control device or mechanism. In some embodiments, such a device can include one or more features, elements, members, devices, etc. configured to selectively control a flow of fluid through at least a portion of the tubing 252, as described in further detail herein.

In some embodiments, the connector 200 and/or any suitable portion thereof can include one or more features configured to manage and/or direct at least a portion of the tubing 252 extending from the port 250. Moreover, in some embodiments, the arrangement of the port 250 can be such that the connector 200 forms, for example, a Y-connector (see e.g., FIGS. 2-7) or a T-connector. In the embodiment shown in FIGS. 2-7, the port 250 can be disposed below or at least partially below the proximal coupler 215. In some embodiments, such an arrangement of the port 250 being disposed below the proximal coupler 215 and along a midline of the connector 200 can allow the port 250 and/or the tubing 252 coupled thereto to be routed to either side of the connector 200. Moreover, such an arrangement can reduce a profile and/or size of the connector 200 in at least one of a vertical or lateral direction. In some embodiments, the port 250 and/or the tubing 252 coupled thereto can be and/or can form at least a portion of a fluid line that can be used to deliver fluid, remove fluid, flush fluid, and/or the like. In other embodiments, the connector 200 can be a single port connector that does not include the port 250.

As described herein, the connector 200 can include any suitable feature or combination of features and/or can be configured to perform any suitable function or combination of functions. As an example, in some embodiments, the connector 200 can be a stable, comfortable, and sleek IV extension set that is configured for use with one or more VADs or other access devices. In some embodiments, the connector 200 can provide a stable and secure connection for a VAD (e.g., a PIV or the like) and/or any other device coupled to the connector 200. In some embodiments, the connector 200 can be configured as a dual port access connector 200 with a port or lumen available for one or more objects to be passed therethrough (e.g., a blood draw catheter or device) and a second port or lumen available for one or more fluids to be passed therethrough—independently or substantially concurrently. In some embodiments, the connector 200 can include one or more features and/or a combination thereof that can, for example, provide for and/or improve patient comfort, provide for and/or improve blood flow through one or more veins underneath the connector 200, prevent accidental unlocking of a spin collar, luer lock, and/or coupler as a result of undesirable rotational motion, provide for and/or improve ease of handling and/or grip of one or more portions of the connector 200, reduce motion otherwise transferred to an insertion site of the patient or indwelling VAD (e.g., less "pistoning"), provide for and/or facilitate the use with and/or connection to any suitable device (e.g., fluid transfer device, fluid collection device, access device, etc.), and/or the like.

In some embodiments, the connector 200 can be included in and/or can at least partially form a transfusion system for the delivery, withdraw, and/or transfer of fluids, medications, blood or blood products, objects, devices, etc. For example, the connector 200 can allow for the delivery and/or aspiration of fluids, substances, etc. via the VAD without an additional needle stick, venipuncture, and/or the like. In some embodiments, the connector 200 can be configured for use with one or more fluid transfer devices for use as a direct blood draw device into a vacuum tube, syringe or blood culture holder (e.g., without use of a needle).

For example, in some embodiments, the connector 200 can be coupled between a VAD at least partially disposed in a portion of the body and a device configured to advance a catheter or other fluid conduit through the connector 200 and through the VAD to allow for aspiration of bodily fluid (e.g., blood) and/or to allow for delivery of a fluid. For example, in some embodiments, the connector 200 can be coupled to and/or otherwise used with a VAD (e.g., a PIV or the like) and a medical device such as those described in U.S. Patent Publication No. 2014/0364766 entitled, "Systems and Methods for Phlebotomy Through a Peripheral IV Catheter," filed Aug. 26, 2014; U.S. Patent Publication No. 2017/0216564 entitled, "Devices and Methods for Fluid Transfer Through a Placed Peripheral Intravenous Catheter," filed Feb. 3, 2016; and/or U.S. Pat. No. 9,744,344 entitled, "Devices and Methods for Catheter Placement Within a Vein," filed Jun. 30, 2016, the disclosures of which are incorporated herein by reference in their entireties.

The connector 200 can be formed of or from any suitable material or combination of materials such as those described herein. In some embodiments, for example, the connector 200 can be formed of a material that is bio-compatible (e.g., compatible with ISO 10993-1:2009 standards regarding, for example, cytotoxicity, acute systemic toxicity, sub-chronic toxicity, hemo-compatibility, and/or the like). The material and/or combination of materials can also be compatible with alcohol, lipids, chlorhexidine, chemotherapy, contrast dye, etc. In some embodiments, the connector 200 can be formed of a material or combination of materials having a shelf-life stability of 1 year, 2 years, 3 years, or more. Moreover, the material or combination of materials can be compatible with any suitable sterilization process (e.g., ethylene oxide (ETO), Gamma sterilization, and/or the like) substantially without discoloration or other adverse effects. In some embodiments, for example, the connector 200 can be sterile (or sterilizable) and non-pyrogenic, can be compatible with magnetic resonance imaging (MRI), and/or can be diethylhexyl phthalate (DEHP)-free and/or latex-free. Moreover, the connector 200 can adhere to and/or surpass standards, recommendations, and/or guidelines provided by the Food and Drug Administration ("FDA").

In some embodiments, the connector 200 can be configured to improve patient comfort, improve stabilization and/or securement, improve ease of use, and/or provide a relatively low profile/footprint (e.g., when compared to some known IV extension sets and/or stabilization devices) while allowing for high volume manufacturing. In some embodiments, the connector 200 can be configured to minimize skin pressure points such that the connector 200 can be comfortable to wear for 1 day, 2 days, 3 days, 4 days, 5 days, or more. The connector 200 and/or the stabilization portion 230 thereof can be easy to tape or secure with industry standard dressings, including Tegaderm™ and/or the like. The connector 200 can have a relatively small size (e.g., height and area) and can be configured to reduce or limit overhang on the hand or other suitable insertion site. For example, in some embodiments, the connector 200 can have a length that is about 1.48 inches (about 37.6 millimeters (mm)). In other embodiments, the connector 200 can have a length that is greater than or less than 1.48 inches (about 37.6 mm).

In some embodiments, the connector 200, connector portion 210, and/or an inner surface defining the lumen 225 can include and/or can incorporate one or more internal aligning features configured to allow the passage of one or more objects, tubes, guidewires, catheters, and/or any other suitable device and/or member. In some embodiments, the lumen 225 of the connector portion 210 can be substantially straight and/or can allow for a substantially straight line of sight therethrough (e.g., at least between the proximal coupler 215 and the distal coupler 220). For example, in some embodiments, a substantially straight path and/or a substantially straight portion of the inner surface defining the lumen 225 can define, for example, an opening, path, or lumen having a diameter of about 1.4 mm, which can guide, direct, support, align, center, etc. one or more objects or devices (e.g., a catheter or the like) through the connector 200. In other embodiments, the lumen or a portion of the lumen can define an opening, path, or lumen having a diameter that is less than 1.4 mm or greater than 1.4 mm.

In some embodiments, the couplers 215 and/or 220 can be configured for use with any suitable coupler, connector, and/or attachment means. For example, in some embodiments, the proximal coupler 215 and/or the distal coupler 220 can be luer locks and/or any other suitable attachment means (e.g., couplers and/or connectors compatible with the ISO luer standards—male connector standard ISO 594-1 and the female connector standard 594-2). More specifically, the connector 200 can be luer activated to accommodate coupling to products and/or devices using luer connectors (e.g., VADs, fluid collection or transfer devices, syringes, access devices, and/or any other suitable device). Furthermore, the in some embodiments, the couplers 215 and/or 220 can include and/or can form a needle-free connector (NFC), and/or can include a NFC valve or the like.

In some embodiments, the couplers 215 and/or 220 can be arranged and/or configured to accept a click to connect coupling (e.g., a click-lock-snap™ connection), a threaded coupling, a luer connection, and/or the like and can be compatible with any suitable valve and/or seal (e.g., a valve used in a luer lock). In some embodiments, the couplers 215 and/or 220 can be a needleless or needle-free connector, can be an independent connector, and/or can be swappable. The couplers 215 and/or 220 can include, for example, a spin collar or the like and/or can otherwise be configured to form relatively easy, secure, and fluid tight connections.

Figure 7:
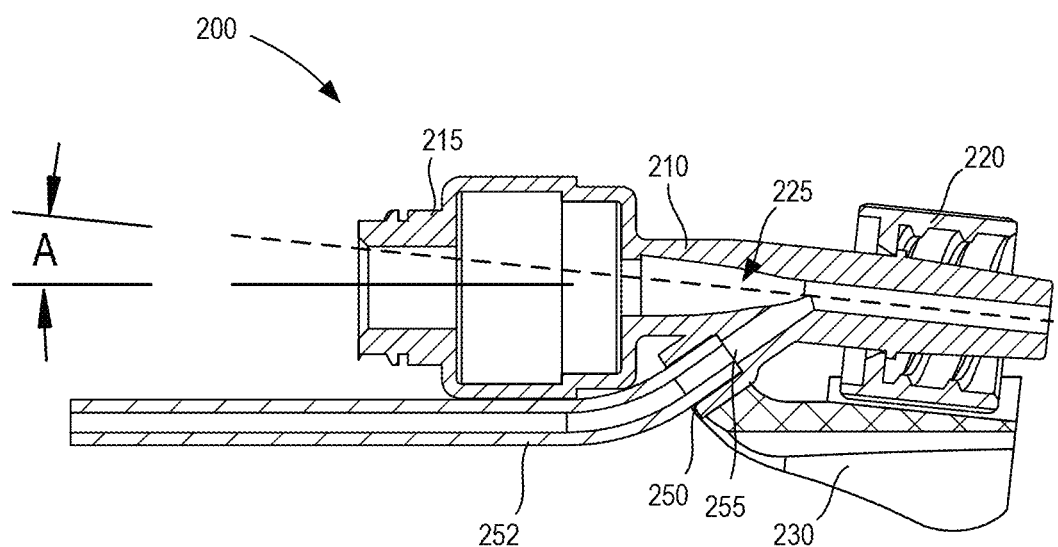
FIG. 7 is a cross-sectional view of the stabilizing connector taken along the line 7-7 in FIG. 6.
Figure 8:
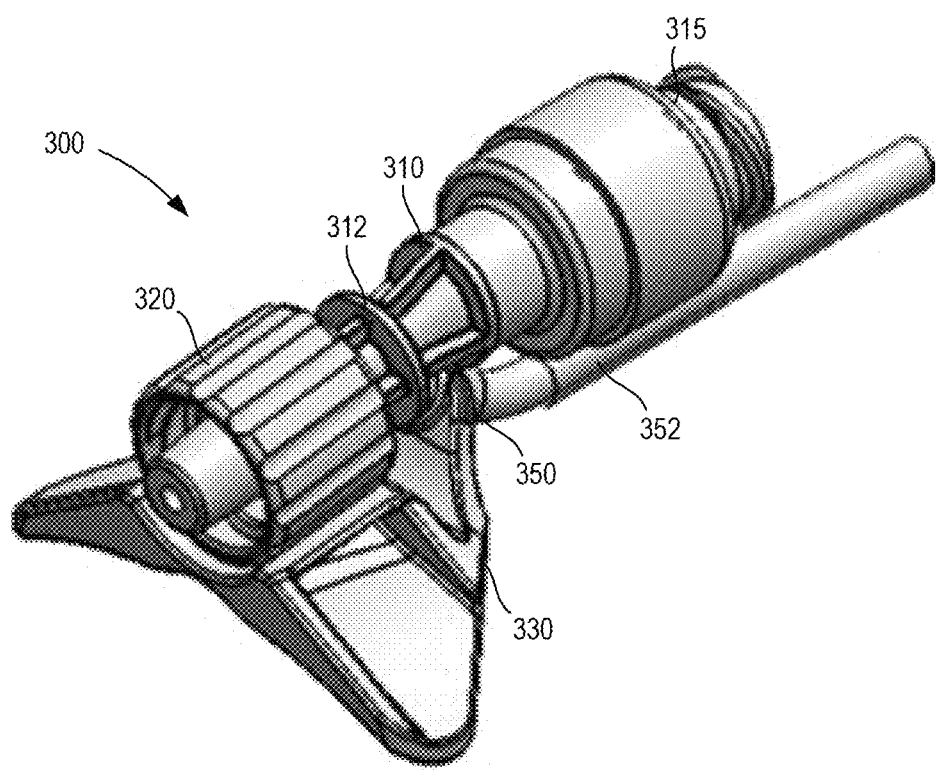
FIGS. 8 and 9 are a top perspective view and a bottom perspective view, respectively, of a stabilizing connector according to an embodiment.
Figure 9:
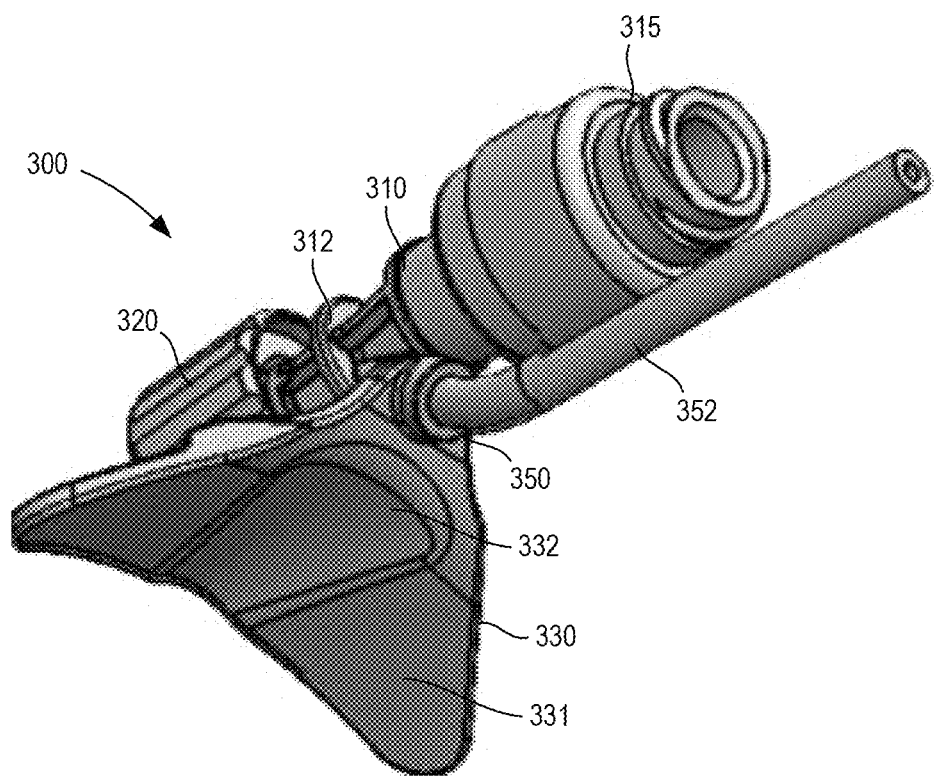
Figure 10:
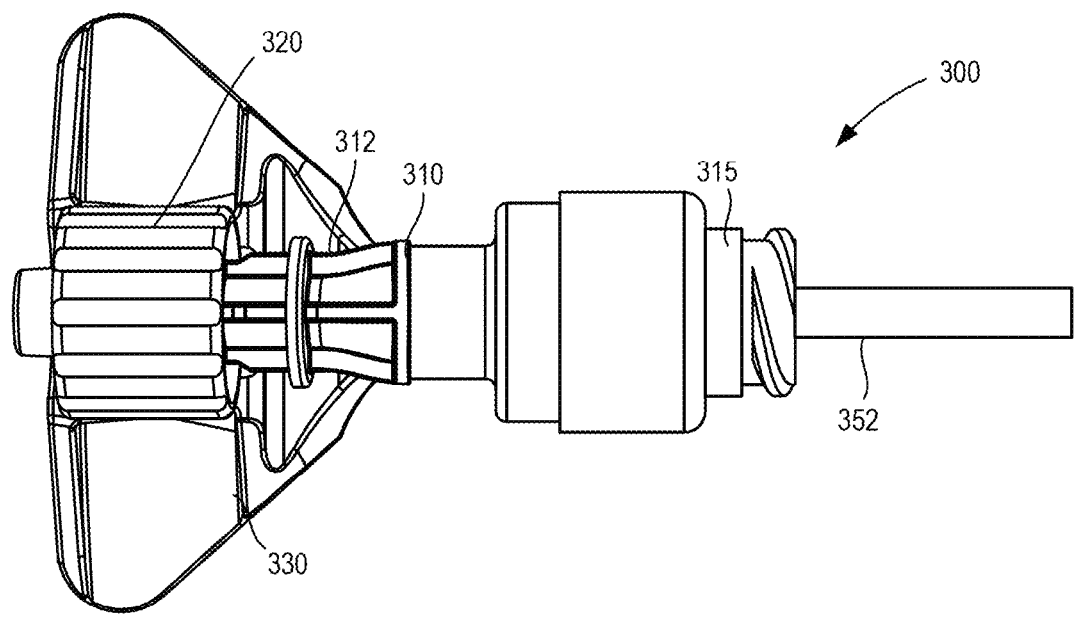
FIGS. 10-14 are a top view, a bottom view, a side view, a front view, and a rear view, respectively, of the stabilizing connector of FIG. 8.
Figure 11:
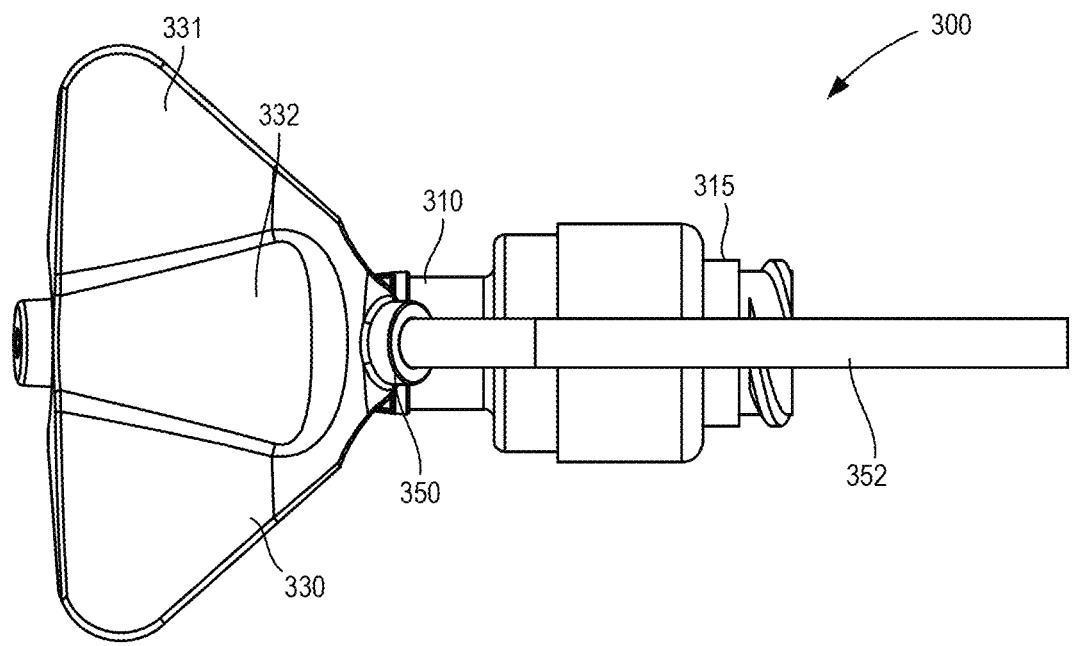
Figure 12:
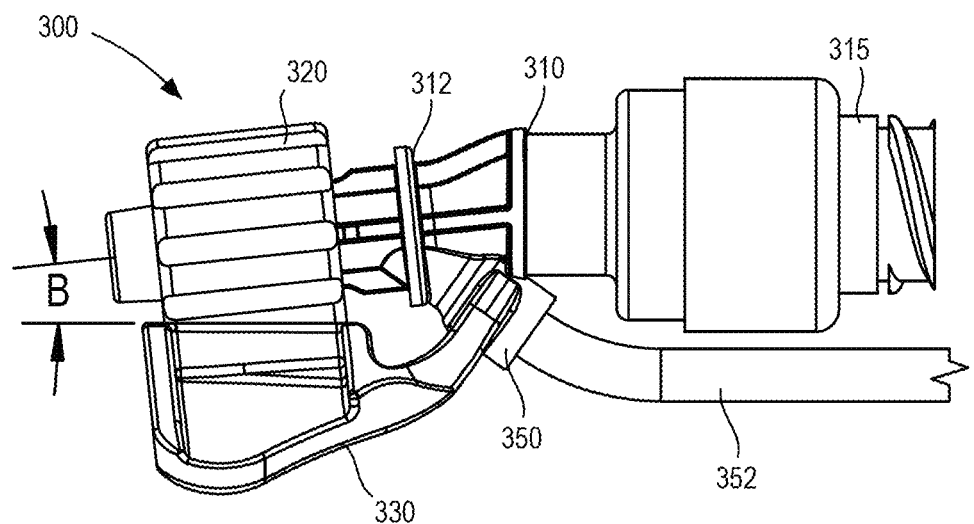

In some embodiments, the arrangement of connector portion 210 and/or the couplers 215 and/or 220 can be configured to maintain a catheter, a VAD, and/or any other suitable device in a desired angle A (referred to herein as a "desired angle" or a "predetermined angle"), as shown in FIG. 7. For example, in some embodiments, the angle A can be a desired or predetermined angle of entry into the body.

In some embodiments, for example, the angle A may be defined with respect to the lumen 225 (or an axis defined by or associated with the lumen 225) extending through or otherwise in fluid communication with the couplers 215 and 220 and a reference plane such as may be formed by an area or plane of contact of the connector 200 with a portion of a patient. That is, the connector portion 210 may be disposed at about the predetermined angle A when the stabilization portion 230 is in contact with the patient such that a common axis extends through the lumen 225 defined by the connector portion 210 and at least a portion of the lumen defined by the access device (not shown). In some embodiments, the angle A can include and/or can be at least partially based on an insertion angle of at least a portion of the access device. In some cases, the stabilization portion 230 can be configured to place the connector portion 210 at about the predetermined angle A relative to the insertion site when the distal coupler 220 is coupled to the hub of the access device and the base surface 231 of the stabilization portion 230 is in contact with the patient.

In some embodiments, the couplers 215 and/or 220 can be configured to couple to, for example, a VAD such that engagement allows a tapered portion thereof to slip into a hub or the like to establish hemostasis, and can include a floating collar or the like such that the connector 200 remains coupled to the VAD during manipulation of one or more devices coupled thereto. In some embodiments, the couplers 215 and/or 220 can be configured to be compatible with any suitable known coupler or connector (e.g., such as those produced by Smiths Medical, Inc. ("Smiths"), Becton, Dickinson, and Company ("BD"), B. Braun Medical, Inc. ("Braun"), ICU Medical, Inc. ("ICU Medical"), Terumo Medical Corporation ("Terumo"), etc.). Moreover, in some embodiments, the couplers 215 and/or 220 can include protective caps and/or the like that are removably coupled to the couplers 215 and 220. Such protective caps can be slip or friction fit or can be coupled via a threaded coupling.

In some embodiments, the connector 200 can be configured for use with and/or configured to control a pressure or flow rate through at least a portion of the connector 200. For example, in some embodiments, the connector 200 can include one or more features and/or can be configured to accept one or more features of a different device that are configured to enhance a flow rate within a vein (e.g., a channel or support). In some embodiments, the connector 200 can be configured to be primed prior to use. In such embodiments, the connector 200 can reduce an amount of a priming volume and an amount of dead space within the connector 200 (e.g., within a range between about 0.3 milliliters (ml) and about 1.0 ml). In some embodiments, the connector 200 can include and/or can be configured to allow for neutral displacement flushing and/or the like. In some embodiments, the connector 200 can enable single port flushing to clear the entire system or substantially the entire system in the double port configuration (e.g., via the port 250). In some embodiments, the connector 200 can be configured to be flushed with a fluid having a volume of, for example, about 1 ml, about 2 ml, about 3 ml, about 4 ml, about 5 ml, about 10 ml, about 20 ml, or more. In addition, the connector 200 can include one or more backflow preventers and/or valves (e.g., check-valves or the like).

In some embodiments, the connector 200 can be used with low-pressure devices such as, for example, syringes, evacuated containers, pumps, injectors, power injectors, etc. (e.g., rated up to 325 pounds-per-square-inch ("psi") or more and configured to support a flow rate of up to 10 milliliters (ml)/second (ml/s) or more). In some embodiments, at least one of the couplers 215 and/or 220 can be a needleless connector port (also referred to herein as a "needle-free connector" (NFC)) with a gravity flow rate similar to or substantially equal to a gravity flow rate of, for example, a 16-gauge PIV (e.g., about 200 ml/min at 1 psi). In other embodiments, the connector 200 and/or at least one of the couplers 215 and/or 220 can have a gravity flow rate flow similar to or substantially equal to a gravity flow rate of, for example, an 18-gauge PIV (e.g., 80-100 ml/min at 1 psi).

While the connector 200 is particularly described above with reference to FIGS. 2-7, in other embodiments, a stabilizing connector can be any suitable shape, size, and/or configuration. For example, in some embodiments, a connector can be a substantially rigid device (e.g., formed of a substantially rigid material) that can have a size that is configured to reduce and/or limit weight, area, and/or footprint (e.g., the connector 200 shown in FIGS. 2-7). In other embodiments, however, a stabilizing connector and/or at least a portion thereof can be formed of a substantially flexible material or a material having a relatively low durometer.

For example, FIGS. 8-15 illustrate a stabilizing connector 300 according to an embodiment. As described above, the stabilizing connector 300 is configured to be placed in contact with the skin of a patient at or near an insertion site of an indwelling or placed vascular access device (VAD) such as those described above. The stabilizing connector 300 is configured to couple to and/or otherwise engage the VAD. Once coupled to the VAD, the stabilizing connector 300 can be secured to the skin of the patient, which in turn, secures and/or stabilizes at least a portion of the VAD relative to the patient, as described in further detail herein. The stabilizing connector 300 can be any suitable shape, size, and/or configuration. For example, in some embodiments, the stabilizing connector 300 and/or at least a portion thereof can be similar in at least form and/or function to the stabilizing connectors 100 and/or 200, described above with reference to FIG. 1 and FIGS. 2-7, respectively. Accordingly, portions of the stabilizing connector 300 may not be described in further detail herein.

As shown, the stabilizing connector 300 (also referred to herein as "connector") has a connector portion 310 and a stabilization portion 330. In some embodiments, the connector 300 can be configured as a combination of one or more stabilization device(s) and an extension set. Each of the connector portion 310 and/or the stabilization portion 330 can be arranged in any suitable manner to facilitate at least one of the functions of providing stabilization to one or more devices (e.g., a VAD or the like) and/or at least one of the functions of providing an extension set for use with a VAD.

The connector portion 310 has a proximal coupler 315 and a distal coupler 320 and defines at least one lumen 325 extending through or otherwise in fluid communication with the couplers 315 and 320. The proximal coupler 315 and/or the distal coupler 320 can be, for example, male or female luer lock and/or any other suitable coupler. As described in further detail herein, the proximal coupler 315 can be physically and fluidically coupled to any suitable medical device such as those described above. The distal coupler 320 can be physically and fluidically coupled to, for example, a VAD or the like (not shown in FIGS. 8-15) such that the lumen 325 of the connector portion 310 is at least selectively in fluid communication with the VAD and/or a portion of the body in which the VAD is at least partially disposed. In some embodiments, the lumen 325 of the connector portion 310 can be substantially straight and/or can allow for a substantially straight line of sight therethrough. In some embodiments, an inner surface of the connector portion 310 can be configured to provide alignment, guidance, centering, etc. to an object or device (e.g., a blood draw catheter or the like) being advanced therethrough.

In the embodiment shown in FIGS. 8-15, the connector portion 310 includes a flexible region 312, which is formed and/or included between the proximal coupler 315 and the distal coupler 320. In some embodiments, the flexible region 312 can be configured to allow the connector portion 310 to flex, bend, bow, and/or otherwise reconfigure. In some instances, the flexing of the connector portion 310 and/or the flexing of the flexible region 312 can, for example, increase a patient's sense of comfort. In other instances, the flexing of the connector portion 310 and/or the flexible region 312 can allow for greater access through the lumen 325 of the connector portion 310 that can allow, for example, an object or device (e.g., a catheter) to be advanced through the lumen 325 substantially without kinking, bending, and/or deforming. In some embodiments, the bending and/or flexing of the connector portion 310 and/or the flexible region 312 can allow the connector 300 to be manipulated such that a substantially straight passage, opening, lumen (or portion thereof), etc. can extend through the connector 300 and/or at least the lumen 325 of the connector portion 310. Moreover, in some embodiments, the connector 300 can be manipulated such that the lumen 325 of the connector portion 310 and/or one or more devices coupled to the connector portion 310 can be disposed at a desired angle B (see e.g., FIG. 12). In some embodiments, the angle B can be a desired angle of insertion into the body, as described above with reference to the connector 200.

The stabilization portion 330 is coupled to the connector portion 310. The stabilization portion 330 can be any suitable shape, size, and/or configuration. For example, in some embodiments, the stabilization portion 330 can be and/or can form a base structure that is angled, tapered, flared, curved, rounded, and/or the like. In some embodiments, the stabilization portion 330 can have a base surface 331 that has a contour and/or shape that is generally concave. In some embodiments, the concave contour and/or shape of the base surface 331 can be based at least in part on a curvature and/or shape of a portion of the patient's anatomy. In some embodiments, forming the contour and/or shape of the base surface 331 to be similar to and/or at least partially based on the curvature of an IV insertion site of the patient, for example, can increase a surface area of the stabilization portion 330 that is in contact with the skin of the patient, which in turn, can increase the stability of the stabilizing connector 300 when secured to the skin of the patient, as described above.

In some embodiments, the base surface 331 of the stabilization portion 330 can be selectively formed of one or more materials (e.g., a relatively hard material and/or a relatively soft material) configured to provide both stabilization and comfort. In some embodiments, the stabilization portion 330 can be configured to provide increased stabilization to a given or desired portion (e.g., a proximal portion, a distal portion, one or more side portions, and/or the like). In some embodiments, the stabilization portion 330 can be reconfigurable, which can allow a user to selectively control an amount of stabilization provided by the stabilization portion 330. Moreover, in some such embodiments, a user can reconfigure (e.g., bend, flex, deform, conform, stretch, break, cut, add to, etc.) one or more portions of the stabilization portion 330 to, for example, control an amount or manner of stabilization, conform at least a portion of the stabilization portion 330 (e.g., the base surface 331) to the contours of a specific patient, reduce or substantially prevent pressure points, and/or the like.

Figure 13:
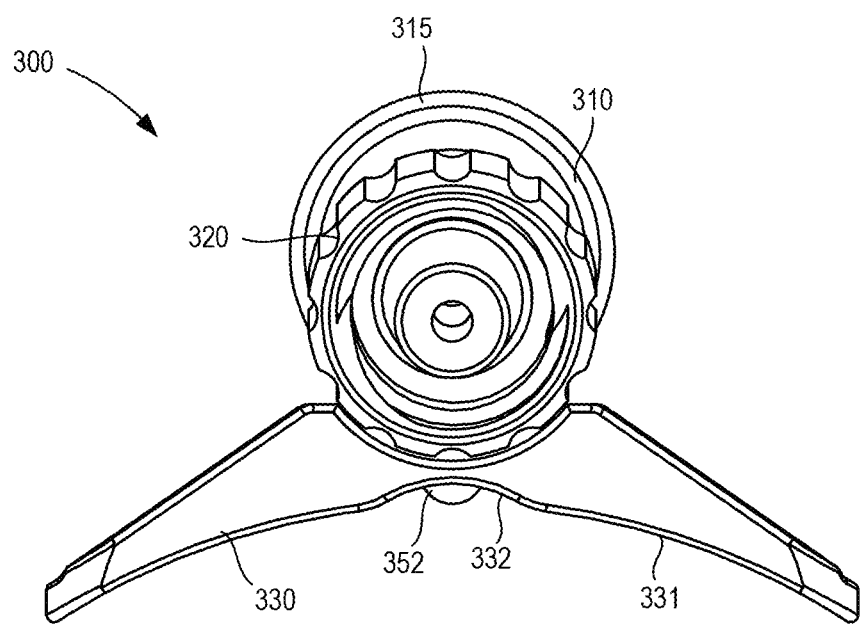
Figure 14:
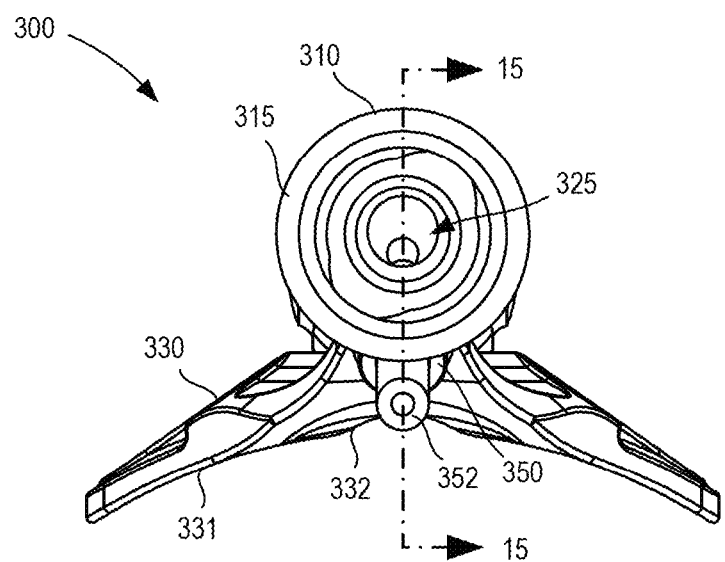

The stabilization portion 330 is configured to be placed in contact with a portion of the patient's skin at or near the insertion site (as described above). As described above with reference to the stabilization portions 130 and/or 230 of the connectors 100 and/or 200, respectively, the base surface 331 of the stabilization portion 330 includes and/or forms a recess, notch, cutout, contour, and/or the like (referred to herein as "recess" 332). For example, as shown in FIGS. 13 and 14, the base surface 331 can form the recess 332 about and/or substantially along a centerline or longitudinal axis of the connector 300. As described above, the recess 332 can be configured to be aligned with and/or disposed above a vein in which the VAD is inserted and arranged such that when the base surface 331 is in contact with the skin of the patient, the recess 332 (or a portion of the base surface 331 defining the recess 332) is spaced apart from the skin of the patient. In some instances, such an arrangement can reduce a force that otherwise may be exerted on the vein, which can result in a pinching, clamping, crimping, and/or occlusion of at least a portion of the vein.

The stabilization portion 330 and/or the stabilizing connector 300 in general, is configured to be secured to the skin of the patient using any suitable securement means. For example, in some instances, the stabilization portion 330 can be taped to the skin of the patient using medical tape or the like or the base surface 331 can include and/or can be coated with an adhesive configured to secure the connector 300 to the patient. In other instances, the stabilization portion 330 can be secured to the skin of the patient using a clear sterile barrier such as, for example, Tegaderm™. In some embodiments, the size, shape, and/or configuration of at least the stabilization portion 330 can be configured to facilitate the securement of the stabilizing connector 300 to the skin of the patient. For example, in some embodiments, the stabilization portion 330 can be configured such that at least a portion of a clear sterile barrier (e.g., Tegaderm™) can wrap around the stabilization portion 330 such that the stabilization portion 330 is disposed within or under the barrier. In some instances, configuring the stabilization portion 330 to allow for the barrier to surround the stabilization portion 330 can, for example, reduce and/or substantially prevent openings in the barrier that may otherwise result in points of contamination or the like.

Figure 15:
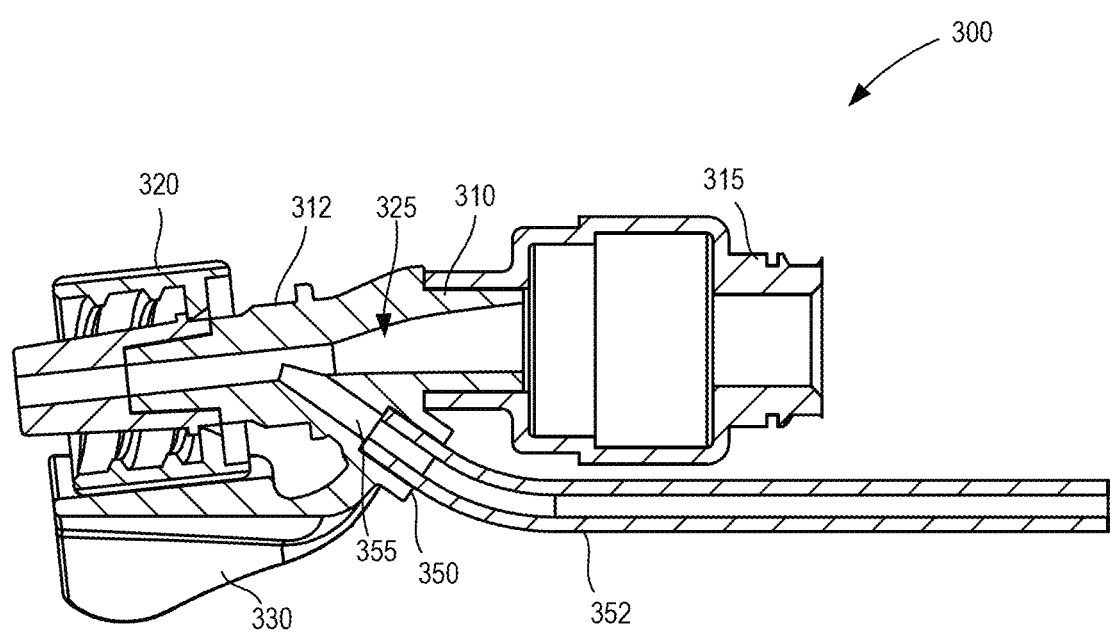
FIG. 15 is a cross-sectional view of the stabilizing connector taken along the line 15-15 in FIG. 14.

The connector 300 also includes a port 350 (see e.g., FIGS. 14 and 15). The port 350 can be included in and/or a part of the connector portion 310, the stabilization portion 330, and/or a combination thereof. As shown, the port 350 can define a lumen 355 that is in fluid communication with the lumen 325. In other words, the connector portion 310 and/or the port 350 can include and/or define a first lumen (e.g., the lumen 325) and a second lumen (e.g., the lumen 355), as shown, for example, in FIG. 15. As such, the port 350 can provide access to the lumen 325, which in turn, can provide access to a device (e.g., a VAD) that is coupled to the distal coupler 320 and/or can provide access to a portion of the body in which the VAD is at least partially disposed. As shown in FIGS. 8-15, the port 350 is coupled to tubing 352 that is in fluid communication with the lumen 355 of the port 350.

In some embodiments, the connector 300 and/or any suitable portion thereof can include one or more features configured to manage and/or direct at least a portion of the tubing 352 extending from the port 350. Moreover, in some embodiments, the arrangement of the port 350 can be such that the connector 300 forms, for example, a Y-connector or a T-connector. In the embodiment shown in FIGS. 8-15, the port 350 can be disposed below or at least partially below the proximal coupler 315. In some embodiments, such an arrangement of the port 350 being disposed below the proximal coupler 315 and along a midline of the connector 300 can allow the port 350 and/or the tubing 352 coupled thereto to be routed to either side of the connector 300. Moreover, such an arrangement can reduce a profile and/or size of the connector 300 in at least one of a vertical or lateral direction. In some embodiments, the port 350 and/or the tubing 352 can be and/or can form at least a portion of a fluid line that can be used to deliver fluid, remove fluid, flush fluid, and/or the like. In other embodiments, the connector 300 can be a single port connector that does not include the port 350.

As described above with reference to the connectors 100 and/or 200, the connector 300 can include any suitable feature or combination of features and/or can be configured to perform any suitable function or combination of functions. As an example, in some embodiments, the connector 300 can be a stable, comfortable, and sleek IV extension set that is configured for use with one or more VADs or other access devices. In some embodiments, the connector 300 can provide a stable and secure connection for a VAD (e.g., a PIV or the like) and any coupled to the connector 300. In some embodiments, the connector 300 can be configured as a dual port access connector 300 with a port or lumen available for one or more objects to be passed therethrough and a second port or lumen available for one or more fluids to be passed therethrough—independently or substantially concurrently. In some embodiments, the connector 300 can include any of the features (or combination of features) and/or can be configured for use with any of the devices (or combination of devices) described above with reference to the connectors 100 and/or 300. Accordingly, such features (or combination of features) and/or such devices (or combination of devices are not described in further detail herein.

As described above, securing the stabilizing connector 300 to the skin of the patient (e.g., via the strips of medical tape) results in the stabilizing connector 300 and/or the medical tape securing, stabilizing, and/or substantially immobilizing the IV catheter relative to the patient. That is to say, the arrangement of the stabilizing connector 300 is such that securing the stabilizing connector 300 and the IV catheter to the skin of the patient can reduce and/or substantially prevent movement of the IV catheter or at least a portion of the IV catheter relative to the vein in which the IV catheter is at least partially disposed. Moreover, the arrangement of the recess 332 along the base surface 331 of the stabilization portion 330 is such that securing and/or adhering the stabilizing connector 300 to the skin of the patient does not exert a force on the vein in which the IV catheter is disposed, thereby reducing and/or substantially eliminating any obstruction and/or restriction otherwise resulting from such a force.

FIGS. 16-19 illustrate at least a portion of a stabilizing connector 400 according to another embodiment. The stabilizing connector 400 (also referred to as "connector" 400) can be substantially similar in form and/or function to the connectors 100, 200, and/or 300 described in detail above. Accordingly, portions of the connector 400 may not be described in further detail herein. In the embodiment shown in FIGS. 16-19, the connector 400 can be configured and/or arranged to facilitate, simplify, and/or otherwise enable manufacturing of the connector 400, as described in further detail herein.

Figure 16:
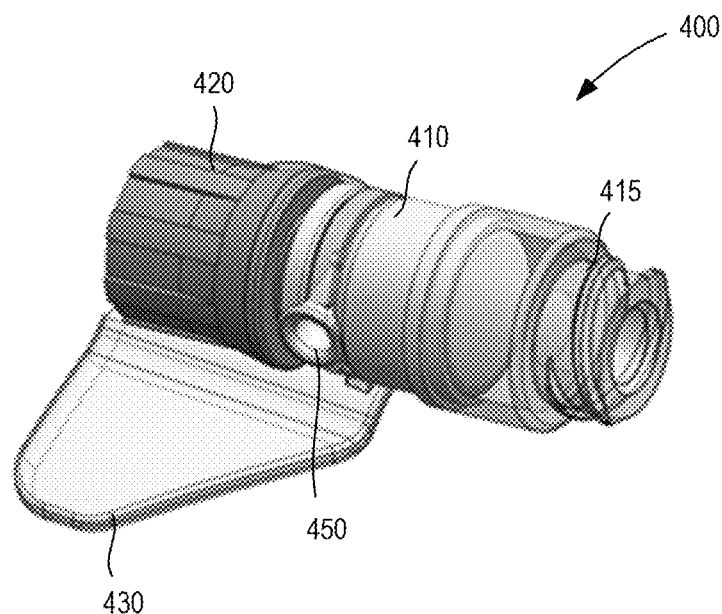
FIGS. 16-19 are various views of at least a portion of a stabilizing connector according to an embodiment.

As shown in FIG. 16, the connector 400 includes a connector portion 410 and a stabilization portion 430. The connector portion 410 includes a proximal coupler 415, a distal coupler 420, and a port 450. The connector portion 410 can be substantially similar in at least form and/or function to the connector portions 110, 200, and/or 310 described in detail above. As shown in FIGS. 16, 18, and 19, the connector portion 410 is configured such that the proximal coupler 415 and the distal coupler 420 can be coupled (e.g., threaded, snapped, pressed, and/or otherwise fixed) to the connector portion 410. In some embodiments, the port 450 similarly can be coupled to the connector portion 410. In other embodiments, the port 450 can be integrally formed with the connector portion 410 (e.g., as in the embodiment shown in FIGS. 16-19). As such, the connector portion 410 can be, for example, formed of three pieces—the connector portion 410, the proximal coupler 415, and the distal coupler 420. In some embodiments, forming the connector portion 410 in three parts (e.g., the connector portion 410, proximal coupler 415, and distal coupler 420) can enhance, facilitate, simplify, and/or reduce the costs associated with manufacturing. Moreover, the proximal coupler 415 and distal coupler 420 are configured to be coupled to and/or assembled with the connector portion 410 during one or more manufacturing processes.

Figure 17:
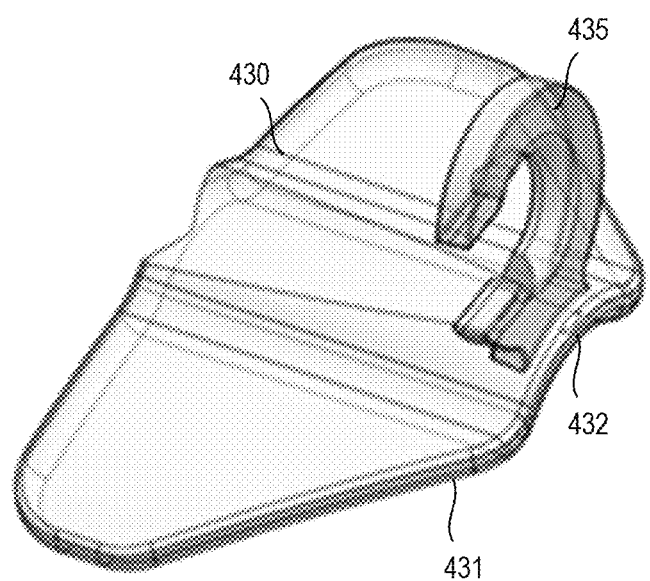
Figure 18:
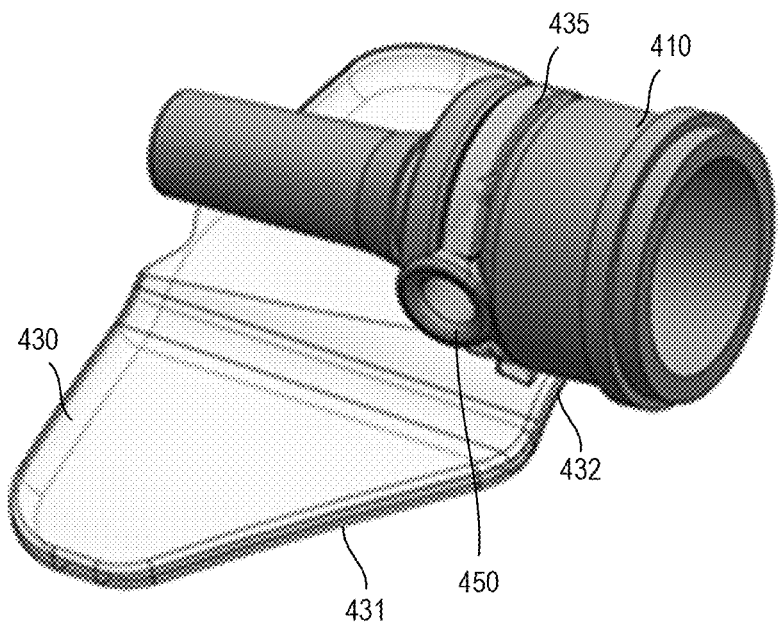
Figure 19:
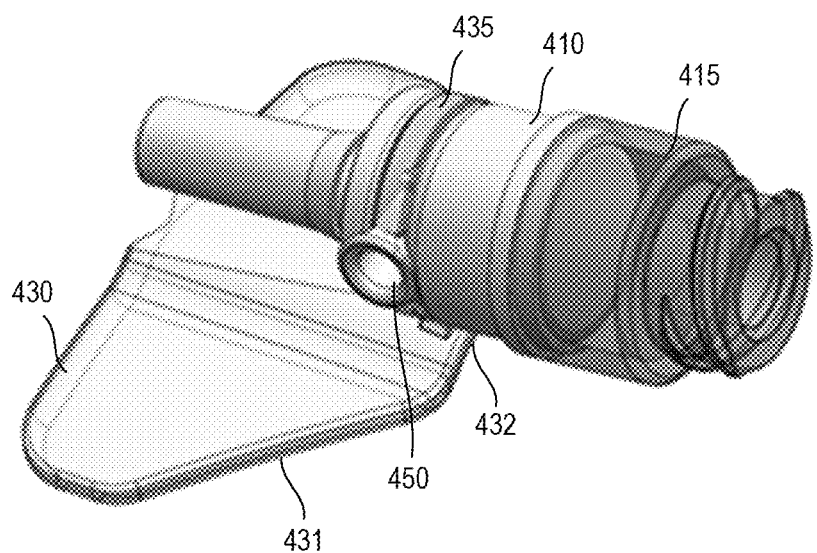

As shown in FIGS. 17 and 18, the stabilization portion 430 includes a coupler 435 configured to couple the stabilization portion 430 to the connector portion 410. The stabilization portion 430 can be any suitable shape, size, and/or configuration. For example, in some embodiments, the stabilization portion 430 can be substantially similar in at least form and/or function to the stabilization portions 130, 230, and/or 330 of the connectors 100, 200, and/or 300, respectively. As shown in FIGS. 17-19, the stabilization portion 430 includes a base surface 431 configured to be placed in contact with the skin of a patient. As described above, the base surface 431 can have a contour that is at least partially based on a size and/or shape of an IV insertion site on the skin of the patient. Moreover, the base surface 431 forms and/or defines a recess 432 configured to be aligned with and/or disposed above a vein of the patient when the connector 400 is secured to the patient. As described in detail above with reference to the connectors 100, 200, and/or 300, the arrangement of the recess 432 can be configured to reduce, limit, and/or substantially eliminate a force otherwise exerted on the vein in which at least a portion of the VAD is inserted.

In the embodiment shown in FIGS. 16-19, the stabilization portion 430 can be formed separately from the connector portion 410 and can be coupled to the connector portion 410 via the coupler 435 during one or more manufacturing processes. More specifically, as shown in FIG. 17, the coupler 435 can be a semi-ring, clamp, clip, and/or any other suitable securement device configured to receive a portion of the connector portion 410 to couple the stabilization portion 430 thereto. Moreover, the arrangement can be such that coupling the stabilization portion 430 to the connector portion 410 does not block or otherwise inhibit access to the port 450, as shown in FIGS. 18 and 19. During manufacturing, the stabilization portion 430 can be coupled to the connector portion 410 by inserting at least a portion of the connector portion 410 into the coupler 435 of the stabilization portion 430 and, for example, fixedly coupling the components via, for example, ultrasonic welding, friction welding, an adhesive, and/or the like.

As described above, in some embodiments, a connector (e.g., the connector 400) can be formed from multiple components that are coupled together and/or assembled during manufacturing. In some embodiments, such an arrangement can reduce costs that might otherwise be associated with, for example, complex molds or the like.

While the stabilizing connector 400 is particularly described above with reference to FIGS. 16-19, in other embodiments, a stabilizing connector can be formed of multiple components having any suitable configuration, which are coupled together and/or assembled during manufacturing to form the assembled stabilizing connector. For example, FIGS. 20-23 illustrate at least a portion of a stabilizing connector 500 according to another embodiment. The stabilizing connector 500 (also referred to as "connector" 500) can be substantially similar in form and/or function to the connectors 100, 200, 300, and/or 400 described in detail above. Accordingly, portions of the connector 500 may not be described in further detail herein. In the embodiment shown in FIGS. 20-23, the connector 500 can be configured and/or arranged to facilitate, simplify, and/or otherwise enable manufacturing of the connector 500, as described in further detail herein.

Figure 20:
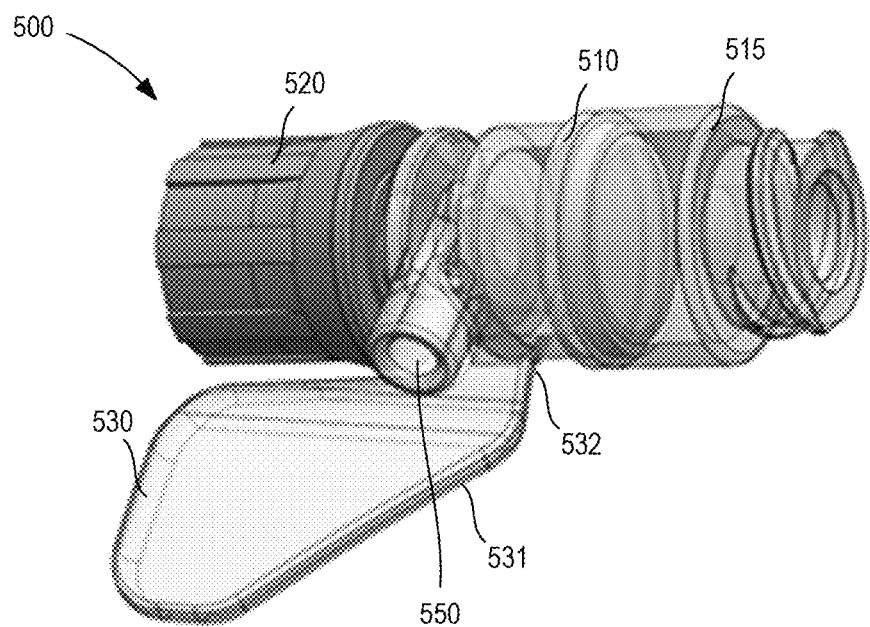
FIGS. 20-23 are various view of at least a portion of a stabilizing connector according to an embodiment.
Figure 22:
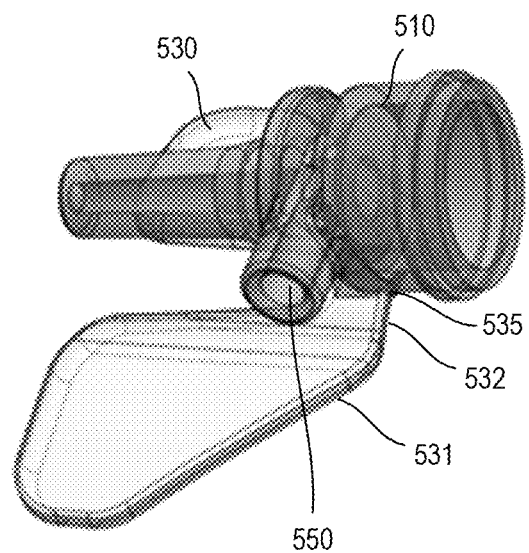
Figure 23:
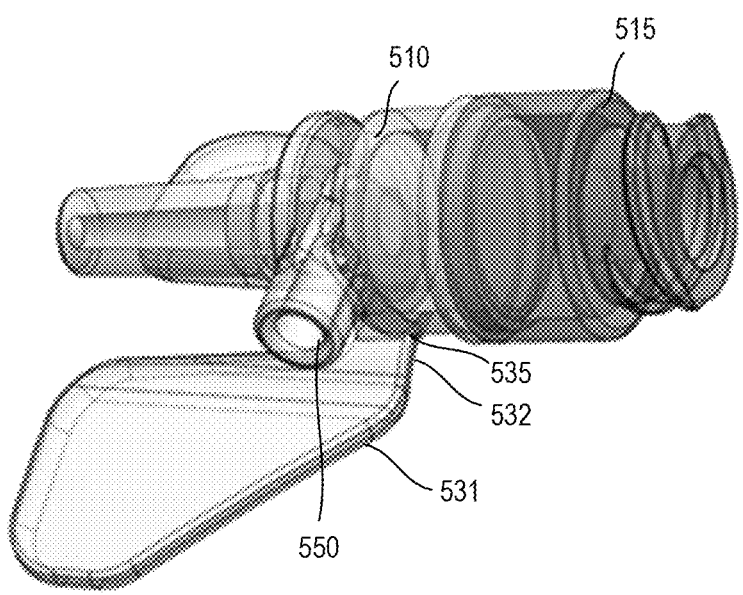

As shown in FIG. 20, the connector 500 includes a connector portion 510 and a stabilization portion 530. The connector portion 510 includes a proximal coupler 515, a distal coupler 520, and a port 550. The connector portion 510 can be substantially similar in at least form and/or function to the connector portions 110, 210, 310, and/or 410 described in detail above. More specifically, as shown in FIGS. 20, 22, and 23, the connector portion 510 is configured such that the proximal coupler 515 and the distal coupler 520 can be coupled (e.g., threaded, snapped, pressed, and/or otherwise fixed) to the connector portion 510. In some embodiments, the port 550 similarly can be coupled to the connector portion 510. In other embodiments, the port 550 can be integrally formed with the connector portion 510 (e.g., as in the embodiment shown in FIGS. 20-23). As such, the connector portion 510 can be, for example, formed of three pieces—the connector portion 510, the proximal coupler 515, and the distal coupler 520, as described in detail above with reference to the connector portion 410. In some embodiments, forming the connector portion 510 in three parts (e.g., the connector portion 510, proximal coupler 515, and distal coupler 520) can enhance, facilitate, simplify, and/or reduce the costs associated with manufacturing.

Figure 21:
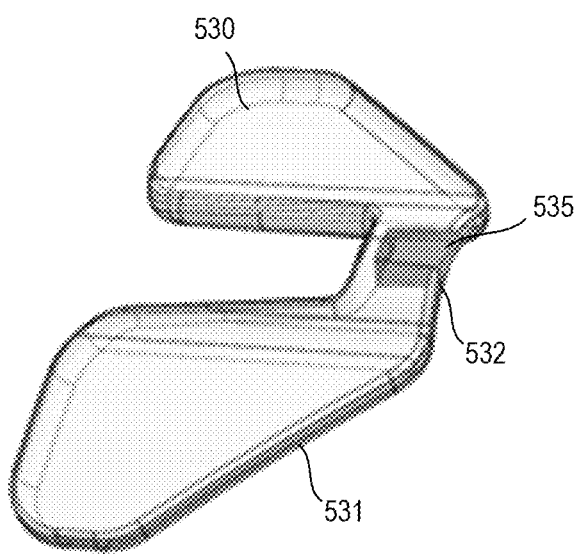

As shown in FIGS. 20 and 21, the stabilization portion 530 includes a coupler 535 configured to couple the stabilization portion 530 to the connector portion 510. The stabilization portion 530 can be any suitable shape, size, and/or configuration. For example, in some embodiments, the stabilization portion 530 can be substantially similar in at least form and/or function to the stabilizing portions 130, 230, 330, and/or 430 of the connectors 100, 200, 300, and/or 400, respectively. As shown, the stabilization portion 530 includes a base surface 531 configured to be placed in contact with the skin of a patient. As described above, the base surface 531 can have a contour that is at least partially based on a size and/or shape of an IV insertion site on the skin of the patient. Moreover, the base surface 531 forms and/or defines a recess 532 configured to be aligned with and/or disposed above a vein of the patient when the connector 500 is secured to the patient. As described in detail above with reference to the connectors 100, 200, 300, and/or 400, the arrangement of the recess 532 can be configured to reduce, limit, and/or substantially eliminate a force otherwise exerted on the vein in which at least a portion of the VAD is inserted.

As described above with reference to the connector 400, the stabilization portion 530 of the connector 500 can be formed separately from the connector portion 510 and can be coupled to the connector portion 510 via the coupler 535 or coupler portion during one or more manufacturing processes. While the coupler 435 of the stabilization portion 430 was shown as forming a ring, clip, clamp, etc., the coupler 535 of the stabilization portion 530 shown in FIGS. 20-23 can be configured to form a dovetail and/or any other suitable coupling, mating, and/or connection with the connector portion 510. Moreover, once the stabilization portion 530 is disposed adjacent to and/or coupled to the connector portion 510 (i.e., during manufacturing), the two components can be fixedly coupled and/or assembled via, for example, ultrasonic welding, friction welding, an adhesive, and/or the like. Thus, as described above with reference to the connector 400, forming the connector 500 of or from multiple components which are coupled together and/or assembled during manufacturing can facilitate, simplify, enhance, and/or reduce costs associated with manufacturing.

While the connectors 200, 300, 400, and/or 500 have each been described as having a port 250, 350, 450, and/or 550, respectively, in other embodiments, a connector need not include such a port or can include a port having any suitable configuration. For example, FIG. 24 is a side view of a known connector 10 (e.g., a dual port extension set) coupled to an intravenous catheter 15. As shown, the connector 10 includes a connector portion 11 (or body), a proximal coupler 12, a distal coupler 13, and a side port 14. The connector portion 11 (or body) can be any suitable shape, size, and/or configuration. The proximal coupler 12 and the distal coupler 13 can be physical and/or fluidic couplers or locks configured to couple to one or more devices. For example, the couplers 12 and 13 can be, for example, needless connectors, luer connectors, and/or the like. In some instances, the distal coupler 13 can be coupled to, for example, the IV catheter 15, while the proximal coupler can be coupled to any suitable device such as an infusion or transfusion device, an aspiration device, an interventional device, and/or the like.

As shown in FIG. 24, the side port 14 can be coupled to and/or can include tubing that can be used to transfer fluids into or out of the connector 10. The arrangement of some known connectors such as the connector 10 can be such that the side port 14 extends substantially perpendicularly from the connector portion 11 (or body). In some instances, a medical procedure can include and/or can call for flushing of connector with a sterile fluid such as saline prior to infusion of a drug or other fluid or prior to aspiration of a bodily fluid. As identified by the region A in FIG. 24, however, such an arrangement can, in some instances, result in a volume of fluid or gas being retained in, trapped in, and/or otherwise not flushed from the proximal coupler 12 (or a portion of the connector portion 11 or body adjacent to the proximal coupler 12). As such, contaminants contained in the non-flushed volume may result in contamination of a sample of bodily fluid, the infusion of the contaminants into an undesirable portion of the body, and/or an undesirable interaction of the unflushed volume (e.g., of fluid or gas) with a subsequent volume of fluid such as bodily fluid, medicament, and/or the like. Moreover, in order to fully flush the connector 10, some medical procedures and/or protocols can include flushing the connector 10 using the side port 14 as well as the proximal coupler 12, which in some instances, can result in increased time or effort in using the connector 10.

In some embodiments, any of the devices described herein can include a side port, one or more internal features, and/or the like configured to fully flush the connector via the side port. For example, FIG. 25 is a side view of a connector 600 according to an embodiment. The connector 600 can be substantially similar to any of the connectors described herein. In other embodiments, the connector can be substantially similar to a standard or known dual port connector or extension set. In other words, the connector can be an integrated stabilizing connector including a connector portion and a stabilizing portion or can be a connector without a stabilizing base or the like. As shown in FIG. 25, the connector 600 includes a connector portion 610 (or body), a proximal coupler 615, a distal coupler 620, and a side port 650. The connector portion 610 (or body) can be any suitable shape, size, and/or configuration. The proximal coupler 615 and the distal coupler 620 can be physical and/or fluidic couplers or locks configured to couple to one or more devices. For example, the couplers 615 and 620 can be, for example, needless or needle-free connectors, luer connectors, and/or the like. In some instances, the distal coupler 620 can be coupled to, for example, an IV catheter 15, while the proximal coupler 615 can be coupled to any suitable device such as an infusion or transfusion device, an aspiration device, an interventional device, and/or the like.

As shown in FIG. 25, the side port 650 can be coupled to and/or can include tubing 652 that can be used to transfer fluids into or out of the connector 600. In this embodiment, the side port 650 can be is a position that is proximal to an otherwise standard or known position of a side port (e.g., the position of the side port 14 shown in FIG. 24) and can extend from the connector portion 610 (or body) at an angle other than a substantially perpendicular angle. For example, in some instances, the side port 650 can be angled such that a lumen of the port is directed toward, for example, the proximal coupler 615. As shown in FIG. 25, in some instances, this arrangement of the side port 650 can be such that when a fluid is flushed through the side port 650 and into the connector portion 610 (or body), the fluid (e.g., saline) flows in a proximal direction toward the proximal coupler 615, which in turn, produces a turbulent flow of the fluid at or near a proximal end portion of the connector 600. As indicated by the region B in FIG. 25, in some instances, such an arrangement can result in a flushing of the proximal end portion of the connector 600 that can be sufficient to remove or flush a volume of fluid or gas that might otherwise be retained in, trapped in, and/or not flushed from the proximal coupler 615 (or a portion of the connector portion 610 or body adjacent to the proximal coupler 615). As such, forming a connector with a side port that is at least one of (1) angled toward a proximal coupler and/or (2) disposed adjacent to the proximal coupler or otherwise offset in the proximal direction can result in complete or otherwise sufficient of the connector via the side port.

Although not shown in FIG. 25, in some embodiments, the connector portion 610 can have an internal surface that can form and/or that can define one or more features configured to facilitate a flushing of the connector 600 via the side port 650. For example, in some embodiments, the internal or inner surface of the connector portion 610 can include, can form, and/or can define one or more features, walls, channels, ports, weirs, veins, flow paths, etc. configured to direct a flow of fluid from the side port 650 toward, for example, the proximal coupler 615. In some embodiments, the one or more features can result in a flow of fluid having a rotational or cyclonic motion. In some embodiments, the one or more features can be configured in increase an amount of turbulence associated with the flow of fluid. In still other embodiments, the one or more features can be configured to facilitate a flushing of the entire connector portion 610 or substantially the entire connector portion 610 in any suitable manner.

FIGS. 26-31 illustrate a stabilizing connector 700 according to an embodiment. As described above, the stabilizing connector 700 is configured to be placed in contact with the skin of a patient at or near an insertion site of an indwelling or placed vascular access device (VAD) such as those described above. The stabilizing connector 700 is configured to couple to and/or otherwise engage the VAD. Once coupled to the VAD, the stabilizing connector 700 can be secured to the skin of the patient (e.g., via medical tape, a clear sterile barrier such as Tegaderm™, and/or the like), which in turn, secures and/or stabilizes at least a portion of the VAD relative to the patient, as described in further detail herein.

The stabilizing connector 700 can be any suitable shape, size, and/or configuration. For example, in some embodiments, the stabilizing connector 700 and/or at least a portion thereof can be similar in at least form and/or function to any of the stabilizing connectors 100, 200, 300, 400, 500, and/or 600 described above. Accordingly, portions of the stabilizing connector 700 may not be described in further detail herein.

Figure 26:
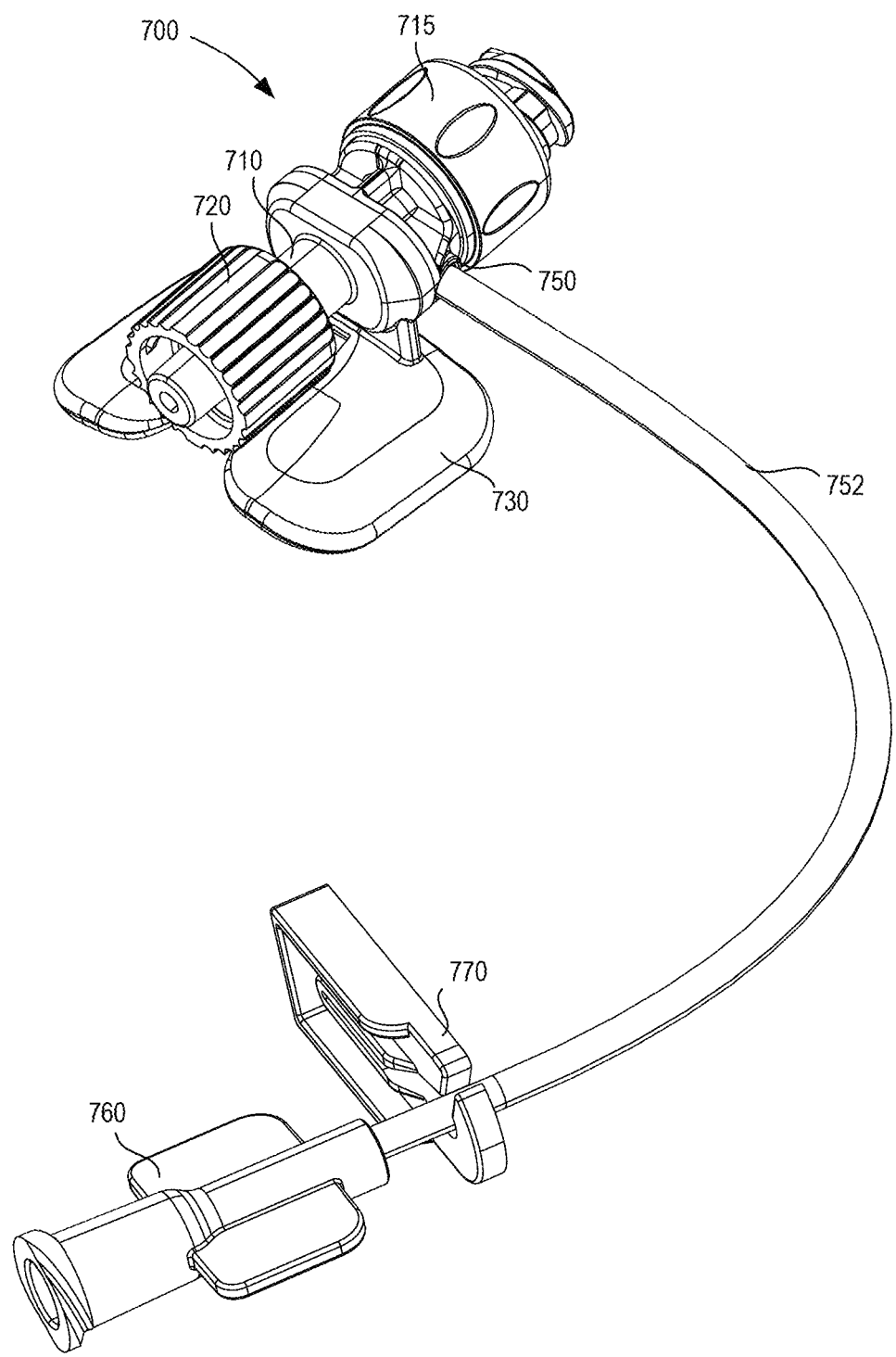
FIGS. 26 and 27 are a perspective view and a side view, respectively, of a stabilizing connector, according to an embodiment.
Figure 27:
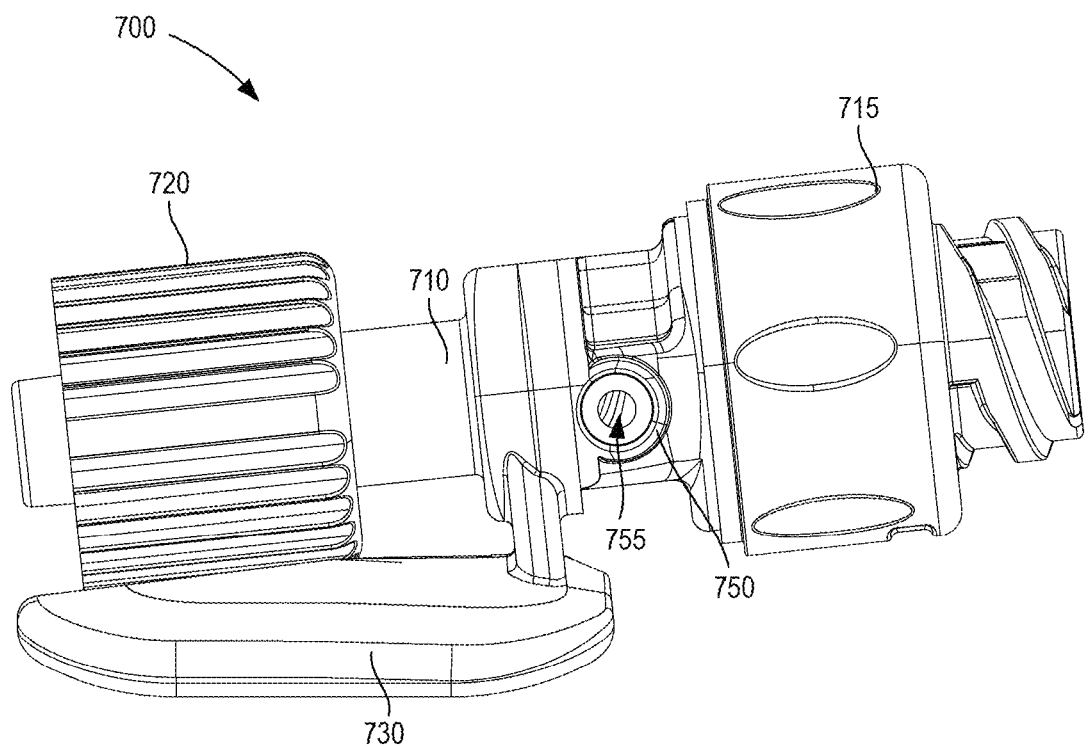
Figure 28:
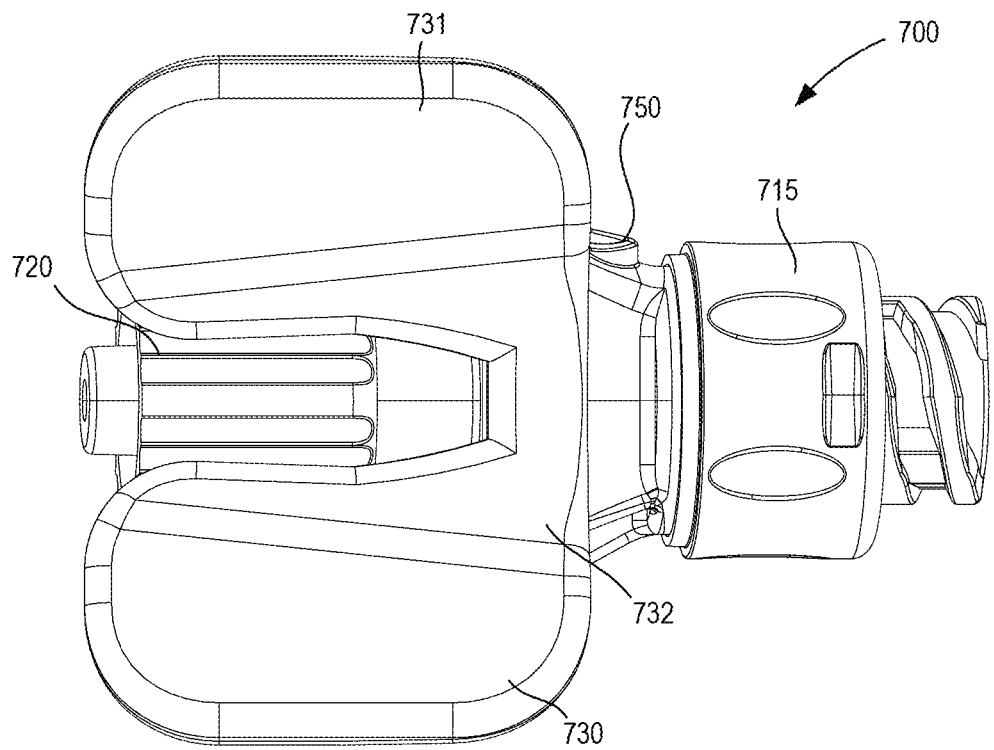
FIG. 28 is a bottom view of the stabilizing connector of FIG. 26.

As shown in FIG. 26, the stabilizing connector 700 (also referred to herein as "connector") has a connector portion 710 and a stabilization portion 730. In some embodiments, the connector 700 can be configured as a combination of one or more stabilization device(s) and an extension set. Each of the connector portion 710 and/or the stabilization portion 730 can be arranged in any suitable manner to facilitate at least one of the functions of providing stabilization to one or more devices (e.g., a VAD or the like) and/or at least one of the functions of providing an extension set for use with a VAD.

The connector portion 710 has a proximal coupler 715 and a distal coupler 720 and defines at least one lumen 725 extending through or otherwise in fluid communication with the couplers 715 and 720. The proximal coupler 715 and/or the distal coupler 720 can be, for example, male or female luer locks, and/or any other suitable coupler. The proximal coupler 715 can be physically and fluidically coupled to any suitable medical device such as those described above. The distal coupler 720 can be physically and fluidically coupled to, for example, a VAD or the like such that the lumen 725 of the connector portion 710 is at least selectively in fluid communication with the VAD and/or a portion of the body in which the VAD is at least partially disposed. In some embodiments, the lumen 725 of the connector portion 710 can be substantially straight and/or can allow for a substantially straight line of sight therethrough. In some embodiments, an inner surface of the connector portion 710 can be configured to provide alignment, guidance, centering, etc. to an object or device (e.g., a blood draw catheter or the like) being advanced therethrough, as described above with reference to the connectors 100, 200, 300, 400, 500, and/or 600.

Figure 29:
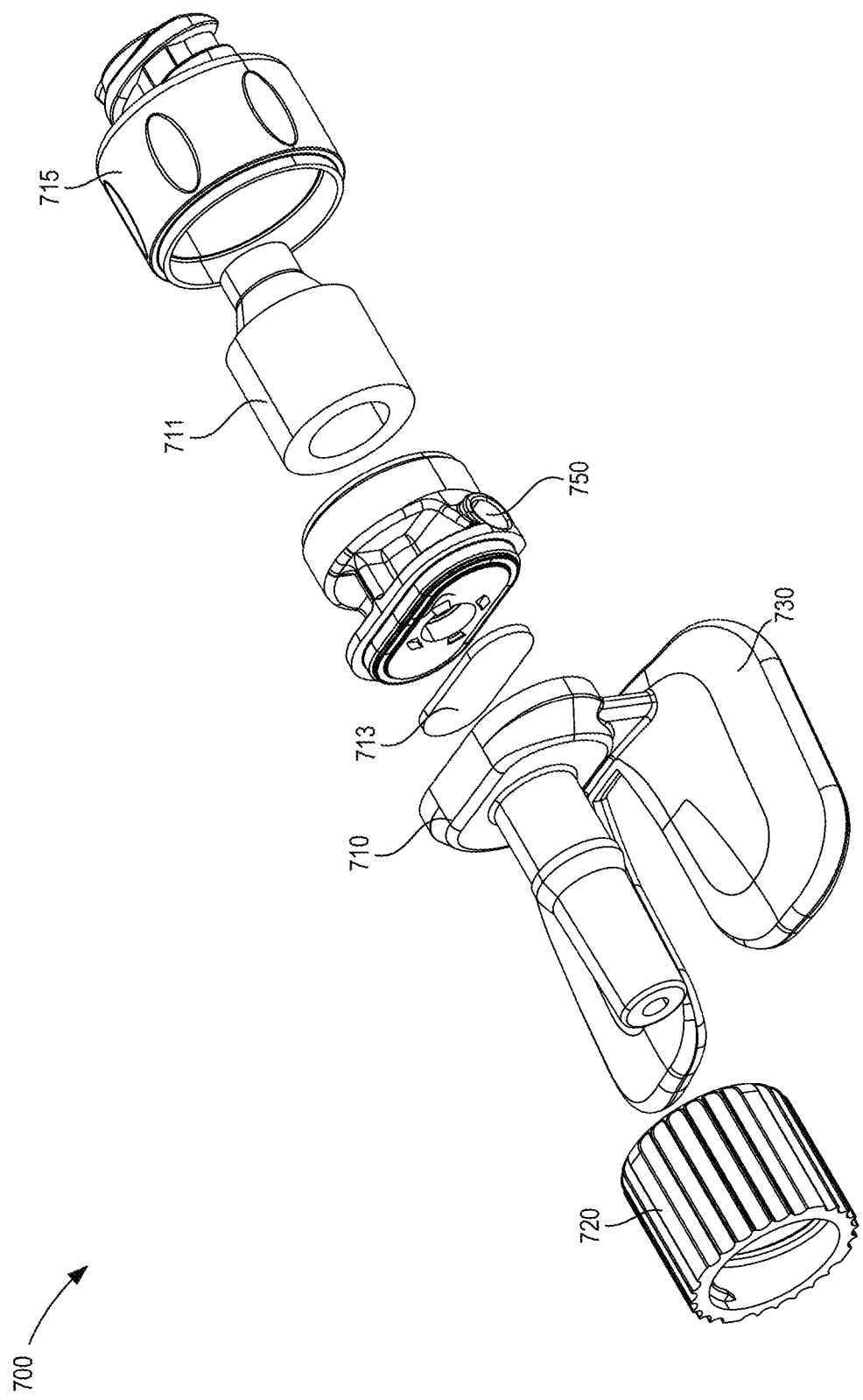
FIG. 29 is an exploded perspective view of the stabilizing connector of FIG. 26.
Figure 30:
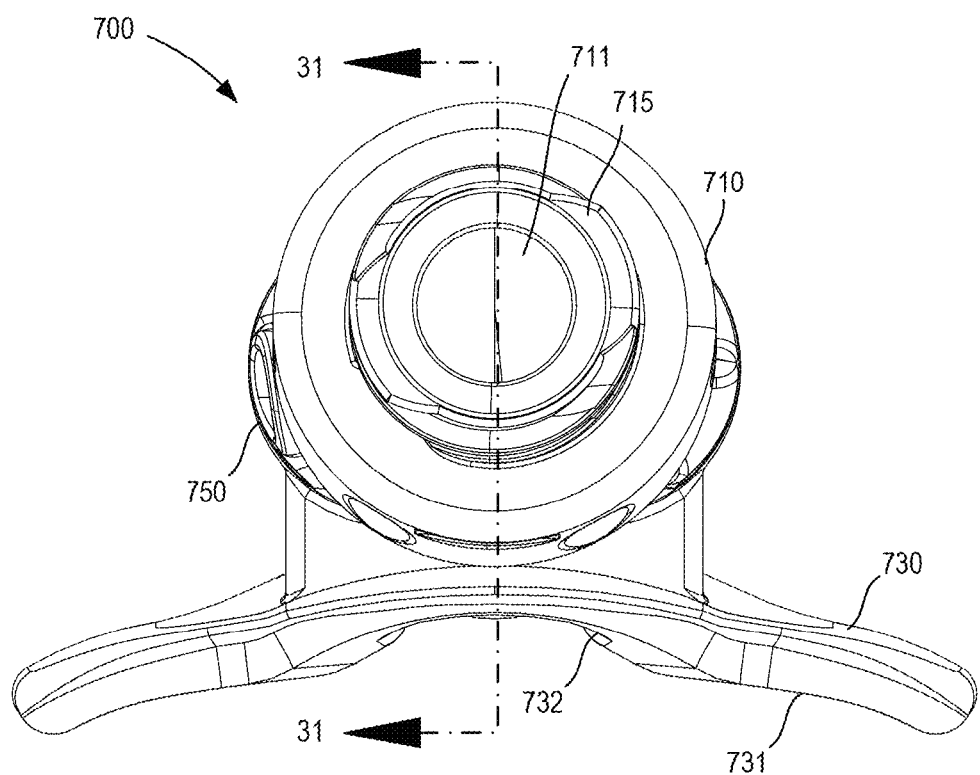
FIG. 30 is a rear view of the stabilizing connector of FIG. 26.
Figure 31:
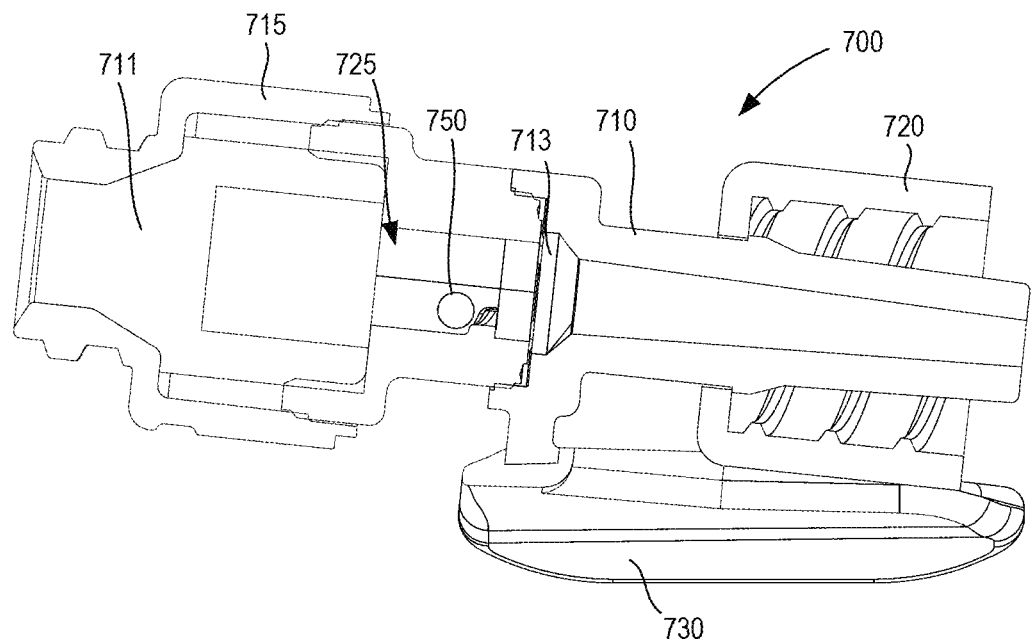
FIG. 31 is a cross-sectional view of the stabilizing connector taken along the line 31-31 in FIG. 30.

In some embodiments, the couplers 715 and/or 720 can be arranged and/or configured to accept a click to connect coupling (e.g., a click-lock-snap™ connection), a threaded coupling, a luer connection, and/or the like. In some embodiments, the couplers 715 and/or 720 can include, for example, a spin collar or the like and/or can otherwise be configured to form relatively easy, secure, and fluid tight connections. In some embodiments, the couplers 715 and/or 720 can be a needleless or needle-free connector, an independent connector, and/or a swappable connector, and/or can be compatible with any suitable valve and/or seal (e.g., a valve used in a luer lock, a NFC valve, a split septum, and/or the like). For example, as shown in FIGS. 29-31, the proximal coupler 715 can include a valve 711 configured to selectively control a flow of fluid through the proximal coupler 715. In some embodiments, the valve 711 can be, for example, an NFC valve, a split septum, a resealable valve or membrane, and/or any other suitable valve. As a specific example, the proximal port 715 can be configured as a needle-free connector or the like and the valve 711 can be, for example, an NFC valve (e.g., similar to or the same as known needle-free connectors and/or known NFC valves).

In some embodiments, the distal coupler 720 can be configured to couple to, for example, a VAD such that engagement allows a tapered portion thereof to slip into a hub or the like to establish hemostasis, and can include a floating collar or the like such that the connector portion 710 remains coupled to the VAD during manipulation of one or more devices coupled thereto. In some embodiments, the couplers 715 and/or 720 can be configured to be compatible with any suitable known coupler or connector (e.g., such as those produced by Smiths, BD, Braun, ICU Medical, Terumo, etc.). In some embodiments, the coupler 720 can be or can include, for example, a floating male luer spin collar, a rotating male luer lock collar, or the like. Moreover, in some embodiments, the couplers 715 and/or 720 can include protective caps and/or the like that are removably coupled to the couplers 715 and 720. Such protective caps can be slip or friction fit or can be coupled via a threaded coupling.

The connector portion 710 also includes and/or defines a port 750. The port 750 can be included in, and/or can be a part of the connector portion 710, the proximal coupler 715, the distal coupler 720, and/or a combination thereof. For example, in the embodiment shown in FIGS. 26-31, the port 750 is distal to the proximal coupler 715. In other embodiments, however, a connector portion can include and/or define a port that is formed by a structure or feature forming a proximal coupler. In some instances, positioning the port 750 in a desired position along a length of the connector portion 710 between the couplers 715 and 720, can allow for a reduced length of the connector portion 710 and/or can facilitate flushing and/or fluid transfer via the port 750.

The port 750 can define a lumen 755 that is in fluid communication with the lumen 725. In other words, the connector portion 710 and/or the port 750 can include and/or define a first lumen (e.g., the lumen 725) and a second lumen (e.g., the lumen 755). As such, the port 750 can provide access to the lumen 725, which in turn, can provide access to a device (e.g., a VAD) that is coupled to the distal coupler 720 and/or can provide access to a portion of the body in which the VAD is at least partially disposed.

As shown in FIG. 26, the port 750 is coupled to tubing 752 that is in fluid communication with the lumen 755 of the port 750. In some embodiments, the connector 700 and/or any suitable portion thereof can include one or more features configured to manage and/or direct at least a portion of the tubing 752 extending from the port 750. As shown, an end portion of the tubing 752 (e.g., an end portion opposite the port 750) can include and/or can be coupled to an attachment device, coupler, connector, port, and/or the like. For example, in the embodiment shown in FIGS. 26-31, the tubing 752 can include a coupler 760 configured to couple to any suitable device such as a fluid source, a fluid collection device, an evacuated container, a pump, a syringe, and/or any other suitable device. Moreover, in some embodiments, the connector 700 can include a clamp 770 coupled to the tubing 752 and configured to selectively engage the tubing 752 to constrict, crimp, clamp, and/or otherwise occlude a lumen defined by the tubing 752 to limit and/or substantially prevent a flow of fluid therethrough. Although the clamp 770 is shown as being separate from the coupler 760, in other embodiments, at least a portion of the clamp 770 can be integrated into the coupler 760, as described in further detail herein with respect to specific embodiments.

In some embodiments, the arrangement of the port 750 can be such that the connector portion 710 forms, for example, a Y-connector or a T-connector. More particularly, in the embodiment shown in FIGS. 26-31, the port 750 can be disposed substantially perpendicular to the lumen 725 of the connector portion 710 and near or adjacent the proximal coupler 715. In some embodiments, a position of the port 750 can be shifted along the connector portion 710 in a desired manner to enable use of a shorter proximal connector (e.g., the proximal coupler 715). In some embodiments, the port 750 and/or the tubing 752 coupled thereto can be and/or can form at least a portion of a fluid line that can be used to deliver fluid, remove fluid, flush fluid, and/or the like. In such embodiments, for example, an arrangement in which the port 750 is disposed adjacent to the proximal coupler 715 can enable flushing of the proximal coupler 715 the valve 711, and/or a space between the valve 711 and an inner surface of the connector portion 710 (e.g., defining at least a portion of the lumen 725). In other embodiments, the connector portion 710 can be a single port connector that does not include the port 750 (and that can be flushed, for example, through the proximal port 715).

In some embodiments, the connector 700 can be configured for use with and/or configured to control a pressure or flow rate through at least a portion of the connector portion 710 and/or the lumen 725 thereof. In some embodiments, the connector portion 710 can include and/or can accept one or more features, members, devices, and/or the like configured to control a flow of fluid through at least a portion of the connector portion 710 and/or the lumen 725. For example, in the embodiment shown in FIGS. 26-31, the connector portion 710, the distal coupler 720, and/or the proximal coupler 715 can include a fluid flow control device 713 (see e.g., FIGS. 29 and 31). The fluid flow control device 713 can be implemented to and/or can be operable in controlling a pressure or flow rate through at least a portion of the lumen 725. The fluid flow control device 713 can include, for example, one or more backflow preventers and/or valves (e.g., anti-reflux valves, check-valves, split septums, and/or the like), one or more pressure regulators, and/or any other suitable flow control device in accordance with specific embodiments. In some embodiments, the fluid flow control device 713 can be, for example, incorporated in, integral with, and/or otherwise disposed within or adjacent to the connector portion 710, the distal coupler 720, and/or the proximal coupler 715. More particularly, in some embodiments, the fluid flow control device 713 can be disposed in a position distal to the port 750, while the valve 711 is proximal to the port 750, as shown in FIG. 31.

In some embodiments, the connector portion 710 can be configured to be primed and/or flushed prior to use. In some embodiments, the connector portion 710 can include and/or can be configured to allow for neutral displacement flushing and/or the like. In some embodiments, the connector portion 710 can enable single port flushing to clear the entire system and/or substantially the entire system in the double port configuration (e.g., via the port 750). In some embodiments, the connector portion 710 can be configured to be flushed with a fluid in an amount of, for example, about 1 ml, about 2 ml, about 3 ml, about 4 ml, about 5 ml, about 10 ml, about 20 ml, or more.

In some embodiments, the connector portion 710 can include one or more internal flushing features configured to define one or more fluid flow paths and/or otherwise configured to control and/or direct a flow of fluid through at least a portion of the lumen 725. In some such embodiments, the internal flushing feature(s) can be a feature, a wall, a channel, a flow path, a protrusion, and/or any other suitable feature that can be configured to reduce an amount of a priming volume and an amount of dead space within the connector portion 710 and/or lumen 725 (e.g., within a range between about 0.3 ml and about 1.0 ml). In other embodiments, the connector potion 710 can include any suitable feature configured to facilitate and/or enhance a priming and/or flushing of the connector portion 710, the proximal coupler 715, an NFC valve and/or other valve included in the proximal coupler 715, the distal coupler 720, and/or any other suitable component, part, or region of the connector portion 710.

For example, in some embodiments, an NFC valve and/or any other suitable fluid flow control device can be sized and/or shaped to allow for a complete or substantially complete flushing of, for example, the proximal coupler 715 and/or any other portion of the lumen 725. In some embodiments, a fluid flow control device (e.g., an NFC valve or the like) can include and/or define one or more features, channels, contours, openings, and/or the like configured to facilitate and/or enhance flushing of the proximal coupler 715 and/or any portion of the lumen 725 defined by the connector portion 710. For example, although not shown, in some embodiments, an NFC valve and/or any other suitable fluid flow control device can define an opening and/or hole on a side of the NFC valve (or other suitable device) opposite the port 750. In such embodiments, when priming and/or flushing the connector portion 710 via the port 750, the position of the opening and/or hole on the valve (or the like) can result in a flow of fluid circulating around at least a portion of the valve (or the like), which in turn, can facilitate and/or enhance priming and/or flushing of at least a portion of the lumen 725. Moreover, after the flow of fluid circulates around at least a portion of the valve (or the like), the fluid can flow through the opening and/or hole to flush an internal portion of the valve (or the like) and/or the rest of the lumen 725 of the connector portion 710.

The stabilization portion 730 is coupled to the connector portion 710 and is configured to be placed in contact with a portion of a patient (e.g., the skin of the patient) at or near an insertion site associated with the VAD (or other similar device). The stabilization portion 730 can be any suitable shape, size, and/or configuration. For example, in some embodiments, the stabilization portion 730 can be and/or can form a base structure that is angled, tapered, flared, curved, rounded, and/or the like. In some embodiments, the stabilization portion 730 can have a base surface 731 (or bottom surface) that has a contour and/or shape that is generally concave. In some embodiments, the concave contour and/or shape of the base surface 731 can be based at least in part on a curvature and/or shape of a portion of the patient's anatomy. In some embodiments, forming the contour and/or shape of the base surface 731 to be similar to and/or at least partially based on the curvature and/or angle of an IV insertion site of a patient, for example, can increase a surface area of the stabilization portion 730 (e.g., base surface 731) that is in contact with the skin of the patient, which in turn, can increase the stability of the stabilizing connector 700, and reduce a pressure associated with the stabilizing connector 700, when secured to the skin of the patient, as described in further detail herein.

In some embodiments, the base surface 731 of the stabilization portion 730 can be selectively formed of one or more materials (e.g., a relatively hard material and/or a relatively soft material) configured to provide both stabilization and comfort. In some embodiments, the stabilization portion 730 can be configured to provide increased stabilization to a given or desired portion (e.g., a proximal portion, a distal portion, one or more side portions, and/or the like). In some embodiments, the stabilization portion 730 can be reconfigurable, which can allow a user to selectively control an amount of stabilization provided by the stabilization portion 730. Moreover, in some such embodiments, a user can reconfigure (e.g., bend, flex, deform, conform, stretch, break, cut, add to, etc.) one or more portions of the stabilization portion 730 to, for example, control an amount or manner of stabilization, conform at least a portion of the stabilization portion 730 to the contours of a specific patient, reduce or substantially prevent pressure points, and/or the like.

The base surface 731 can include one or more contours, recesses, notches, cutouts, channels, etc. (referred to herein as a "recess" 732 (see e.g., FIGS. 28 and 30)) configured to reduce an amount of force exerted by the stabilization portion 730 on or more veins of the patient (e.g., the vein in which the VAD is disposed), which might otherwise result in an occlusion of and/or a reduced flow rate through at least a portion of the vein, as described in detail above with reference to the connectors 100, 200, 300, and/or 400. The contour and/or shape of the base surface 731 can be based, for example, at least in part on a curvature and/or shape of a portion of the patient's anatomy. In some embodiments, at least one of the one or more recesses 732 can substantially extend between a proximal edge and a distal edge of the base surface 731.

The stabilization portion 730 and/or the stabilizing connector 700 in general, is configured to be secured to the skin of the patient using any suitable securement means. For example, in some instances, the stabilization portion 730 can be taped to the skin of the patient using medical tape or the like or the bottom surface can include and/or can be coated with an adhesive configured to secure the connector 700 to the patient. In other instances, the stabilization portion 730 can be secured to the skin of the patient using a clear sterile barrier such as, for example, Tegaderm™. In some embodiments, the size, shape, and/or configuration of at least the stabilization portion 730 can be configured to facilitate the securement of the stabilizing connector 700 to the skin of the patient. For example, in some embodiments, the stabilization portion 730 can be configured such that at least a portion of a clear sterile barrier (e.g., Tegaderm™) can wrap around the stabilization portion 730 such that the stabilization portion 730 is disposed within or under the barrier. In some instances, configuring the stabilization portion 730 to allow for the barrier to surround the stabilization portion 730 can, for example, reduce and/or substantially prevent openings in the barrier that may otherwise result in points of contamination or the like.

In some embodiments, the stabilization portion 730 and/or the base surface 731 of the stabilization portion 730 can be configured to enable and/or facilitate free motion of at least a portion of the coupler 720, with respect to various loading conditions (e.g. in the form of applied forces or pressure) to which the stabilizing connector 700 may be subject. For example, in an unloaded condition of the stabilizing connector 700, the stabilization portion 730 can be configured to enable and/or facilitate free motion of at least a portion of the distal coupler 720, such as when the distal coupler 720 is or includes a floating male luer spin collar, or the like. In some such embodiments, when in a loaded condition of the stabilizing connector 700 (e.g., such as when a force or pressure is applied to the stabilization portion 730 in direction substantially perpendicular to an area of contact of the base surface 731 with the patient), the stabilization portion 730 and/or the base surface 731 can be configured to support the coupler 720 (e.g., from below). Accordingly, such support of the coupler 720 can reduce, limit, and/or substantially prevent pressure from being transferred to the patient. In the example shown in FIGS. 26-31, the portion of the coupler 720 for which such free motion can be enabled and/or facilitated can include, for example, the spinnable, rotatable, or otherwise angularly displaceable collar of the male luer.

In some embodiments, the connector 700 can include one or more features and/or a combination thereof that can, for example, provide for and/or improved ease of handling and grip of one or more portions of the connector 700, and/or facilitate the use with and/or connection to any suitable device (e.g., fluid transfer device, fluid collection device, access device, etc.). For example, as shown in FIGS. 26-31, the connector portion 710, the distal coupler 720, or the proximal coupler 715 can include a tapered portion to improve grip and facilitate handling of one or more portions of the connector 700. As another example, the connector 700 can include a flat upper surface having surface area-increasing elements such as grooves for facilitating secure attachment to the skin of a patient (e.g., via medical tape, a clear sterile barrier such as Tegaderm™, and/or the like) to thereby facilitate use with and/or connection to another device.

In some embodiments, the connector 700 can include indicia (not shown) to facilitate use of the connector 700 with respect to a patient and/or connection to any suitable device, such as to prevent user-error (e.g. taping over extension tubing or any other improper portion of the connector 700). For example, the indicia can include markings or symbols to indicate proper alignment of the connector 700 with respect to a treatment site of the patient, proper positioning of the connector 700 with respect to tubing coupled to or configured to be coupled to the connector (e.g., for fluid communication between the tubing 752 and the lumen 755 of the port 750), proper tape application zones of the connector 700, and so on. In some embodiments, the connector 700 can include any of the features (or combination of features) and/or can be configured for use with any of the devices (or combination of devices) described above with reference to the connector 100, 200, 300, 400, 500, and/or 600.

As described above with reference to the connector 100, 200, 300, 400, 500, and/or 600, the connector 700 can include any suitable feature or combination of features and/or can be configured to perform any suitable function or combination of functions. As an example, in some embodiments, the connector 700 can be a stable, comfortable, and sleek IV extension set that is configured for use with one or more VADs or other access devices. In some embodiments, the connector 700 can provide a stable and secure connection for a VAD (e.g., a PIV or the like) and/or any other device coupled to the connector 700. In some embodiments, the connector 700 can be configured as a dual port access connector 700 with a port or lumen available for one or more objects to be passed therethrough (e.g., a blood draw catheter or device) and a second port or lumen available for one or more fluids to be passed therethrough—independently or substantially concurrently.

While the connector 700 is particularly described above with reference to FIGS. 26-31, in other embodiments, a stabilizing connector can be any suitable shape, size, and/or configuration, and/or can be formed of multiple components having any suitable configuration, which are coupled together and/or assembled during manufacturing to form the assembled stabilizing connector. Thus, it should be understood that the size, shape, and/or arrangement of the embodiments and/or components thereof could be adapted for a given use unless the context explicitly states otherwise. For example, while the connector 700 is described above with reference to FIGS. 26-31 as being a dual port stabilizing connector having the proximal coupler 715, the distal coupler 720, and the port 750, in other embodiments, a stabilizing connector can be a single port stabilizing connector having a proximal coupler and a distal coupler but not having an addition port (e.g., no side port or the like).

For example, FIGS. 32-35 illustrate at least a portion of a stabilizing connector 800, according to an embodiment. As described above, the stabilizing connector 800 is configured to be placed in contact with the skin of a patient at or near an insertion site of an indwelling or placed vascular access device (VAD) such as those described above. The stabilizing connector 800 is configured to couple to and/or otherwise engage the VAD. Once coupled to the VAD, the stabilizing connector 800 can be secured to the skin of the patient, which in turn, secures and/or stabilizes at least a portion of the VAD relative to the patient, as described in further detail herein.

The stabilizing connector 800 can be any suitable shape, size, and/or configuration. For example, in some embodiments, the stabilizing connector 800 and/or at least a portion thereof can be similar in at least form and/or function to any of the stabilizing connectors 100, 200, 300, 400, 500, 600, and/or 700 described above. Accordingly, portions of the stabilizing connector 800 may not be described in further detail herein.

As shown in FIGS. 32-35, the stabilizing connector 800 (also referred to herein as "connector") has a connector portion 810 and a stabilization portion 830. In some embodiments, the connector 800 can be configured as a combination of one or more stabilization device(s) and an extension set. Each of the connector portion 810 and/or the stabilization portion 830 can be arranged in any suitable manner to facilitate at least one of the functions of providing stabilization to one or more devices (e.g., a VAD or the like) and/or at least one of the functions of providing an extension set for use with a VAD.

Figure 35:
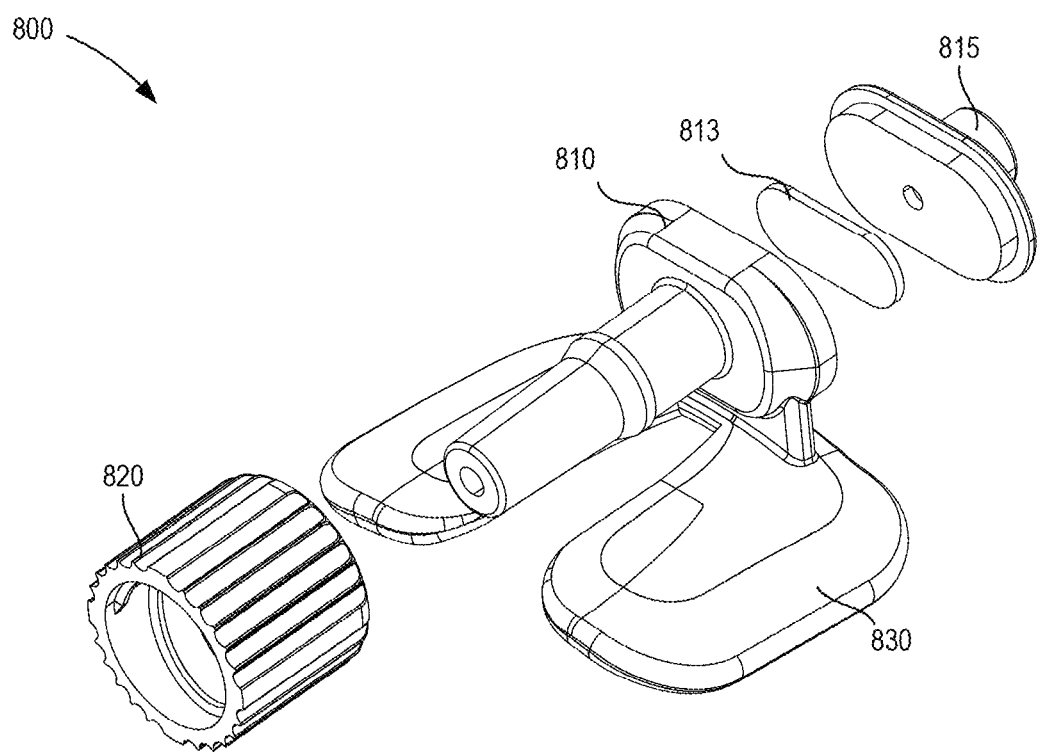
FIG. 35 is an exploded perspective view of the stabilizing connector of FIG. 32.

The connector portion 810 has a proximal coupler 815 and a distal coupler 820 and defines at least one lumen 825 extending through or otherwise in fluid communication with the couplers 815 and 820. The proximal coupler 815 and/or the distal coupler 820 can be, for example, male or female luer locks and/or any other suitable coupler. As described in further detail herein, the proximal coupler 815 can be physically and fluidically coupled to any suitable medical device such as those described above. The distal coupler 820 can be physically and fluidically coupled to, for example, a VAD or the like such that the lumen 825 of the connector portion 810 is at least selectively in fluid communication with the VAD and/or a portion of the body in which the VAD is at least partially disposed. In some embodiments, the lumen 825 of the connector portion 810 can be substantially straight and/or can allow for a substantially straight line of sight therethrough, such as shown in FIG. 35. In some embodiments, an inner surface of the connector portion 810 can be configured to provide alignment, guidance, centering, etc. to an object or device (e.g., a blood draw catheter or the like) being advanced therethrough. In some embodiments, the proximal coupler 815 and/or the distal coupler 820 can be substantially similar to the proximal coupler 715 and/or the distal coupler 720, respectively, described above with reference to the connector 700. Accordingly, similar portions and/or aspects of the proximal coupler 815 and/or the distal coupler 820 are not described in further detail herein.

Figure 32:
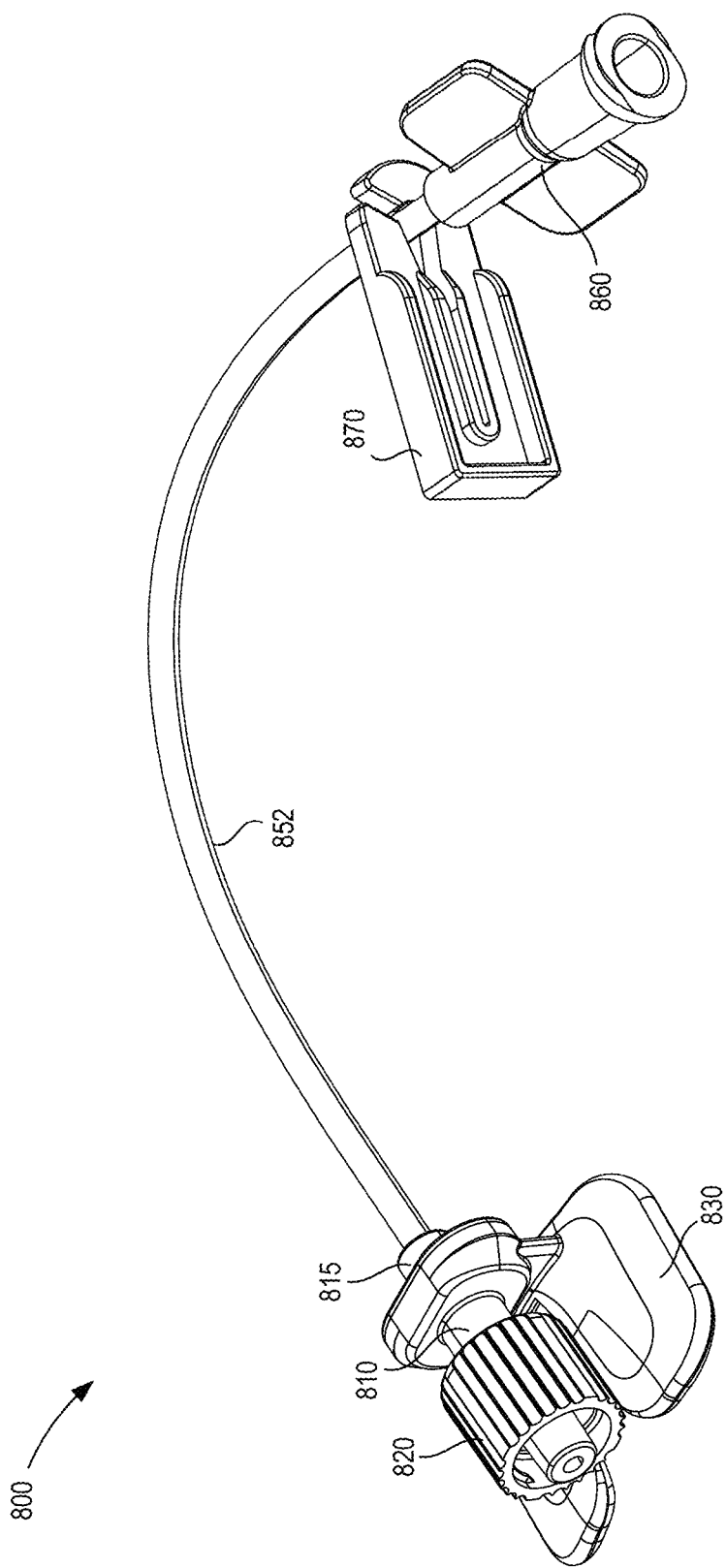
FIG. 32 is a perspective view of a stabilizing connector, according to an embodiment.
Figure 33:
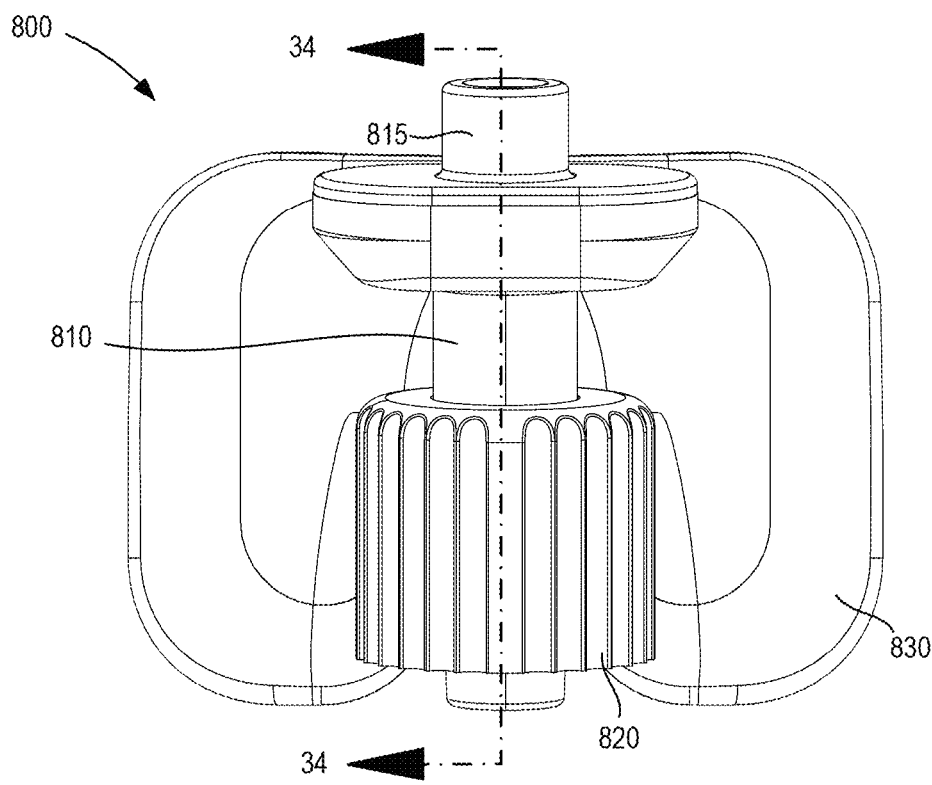
FIG. 33 is a top view of the stabilizing connector of FIG. 32.

As shown in FIG. 32, in some embodiments, the proximal coupler 815 is coupled to tubing 852 such that the tubing 852 is in fluid communication with the lumen 825. In some embodiments, the connector 800 and/or any suitable portion thereof can include one or more features configured to manage and/or direct at least a portion of the tubing 852 extending from the proximal coupler 815. While the tubing 752 is described above as being coupled to the port 750 and used to flush the connector portion 710 of the stabilizing connector 700, in the embodiment shown in FIGS. 32-35, the tubing 852 is coupled to the proximal coupler 815. As such, a user can flush the connector portion 810 via the tubing 852 and the proximal coupler 815.

As described above, an end portion of the tubing 852 (e.g., an end portion opposite the proximal coupler 815) can include and/or can be coupled to an attachment device, coupler, connector, port, and/or the like. For example, in the embodiment shown in FIGS. 32-35, the tubing 852 can include a coupler 860 configured to couple to any suitable device such as a fluid source, a fluid collection device, an evacuated container, a pump, a syringe, and/or any other suitable device. Moreover, in some embodiments, the connector 800 can include a clamp 870 coupled to the tubing 852 and configured to selectively engage the tubing 852 to constrict, crimp, clamp, and/or otherwise occlude a lumen defined by the tubing 852 to limit and/or substantially prevent a flow of fluid therethrough. Although the clamp 870 is shown as being separate from the coupler 860, in other embodiments, at least a portion of the clamp 870 can be integrated into the coupler 860, as described in further detail herein with respect to specific embodiments.

Figure 34:
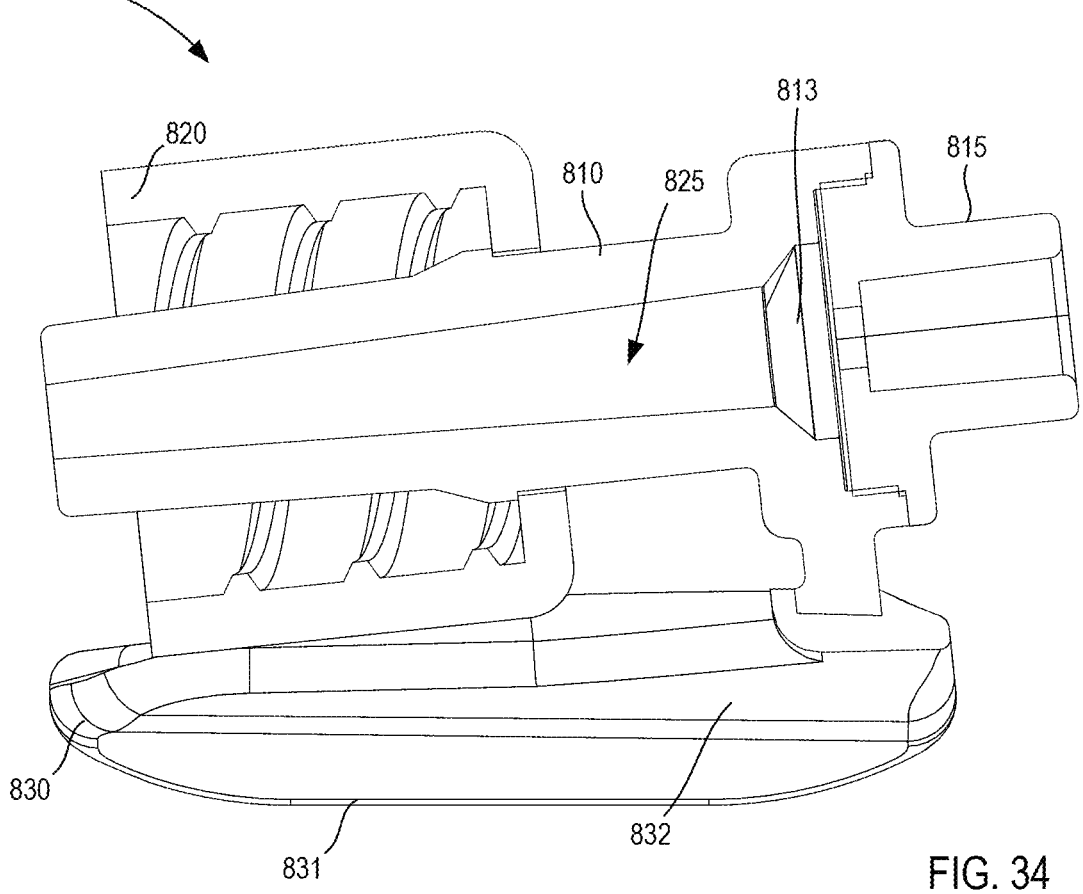
FIG. 34 is a cross-sectional view of the stabilizing connector taken along the line 34-34 in FIG. 33.

As described above with reference to the connector 700, in the embodiment shown in FIGS. 32-35, the connector portion 810, the distal coupler 820, and/or the proximal coupler 815 can include a fluid flow control device 813 (see e.g., FIGS. 34 and 35). The fluid flow control device 813 can be implemented to and/or can be operable in controlling a pressure or flow rate through at least a portion of the lumen 825. The fluid flow control device 813 can include, for example, one or more backflow preventers and/or valves (e.g., anti-reflux valves, check-valves, split septums, and/or the like), one or more pressure regulators, and/or any other suitable flow control device in accordance with specific embodiments. In some embodiments, the fluid flow control device 813 can be, for example, incorporated in, integral with, and/or otherwise disposed within or adjacent to the connector portion 810, the distal coupler 820, and/or the proximal coupler 815.

The stabilization portion 830 is coupled to and/or integrally formed with at least a part of the connector portion 810. The stabilization portion 830 can be any suitable shape, size, and/or configuration. For example, in some embodiments, the stabilization portion 830 can be similar to or substantially the same as the stabilization portion 730 described above. Accordingly, similar portions and/or aspects of the stabilization portion 830 are not described in further detail herein.

As shown in FIG. 32, the stabilization portion 730 can have a base surface 731 (or bottom surface) that has a contour and/or shape that is generally concave. In some embodiments, the concave contour and/or shape of the base surface 731 can be based at least in part on a curvature and/or shape of a portion of the patient's anatomy, as described above with reference to the stabilization portion 630. Moreover, the base surface 731 of the stabilization portion 730 can include and/or can define one or more contours, recesses, notches, cutouts, channels, etc. (referred to herein as "recess" 732 (see e.g., FIG. 32) configured to reduce an amount of force exerted by the stabilization portion 730 on or more veins of the patient (e.g., the vein in which the VAD is disposed), as described in detail above.

The stabilization portion 830 is configured to be placed in contact with a portion of the patient's skin at or near the insertion site (as described above). In addition, the stabilization portion 830 and/or the stabilizing connector 800 in general, is configured to be secured to the skin of the patient using any suitable securement means, such as those described above with reference to at least the stabilization portion 730. In some instances, securing the stabilizing connector 800 to the skin of the patient (e.g., via the strips of medical tape) results in the stabilizing connector 800 and/or the medical tape securing, stabilizing, and/or substantially immobilizing the VAD (e.g., an IV catheter) relative to the patient. That is to say, the arrangement of the stabilizing connector 800 is such that securing the stabilizing connector 800 and the IV catheter to the skin of the patient can reduce and/or substantially prevent movement of the IV catheter or at least a portion of the IV catheter relative to the vein in which the IV catheter is at least partially disposed. Moreover, the arrangement of the recess 832 along the base surface 831 is such that securing and/or adhering the stabilizing connector 800 to the skin of the patient does not exert a force on the vein in which the IV catheter is disposed, thereby reducing and/or substantially eliminating any obstruction and/or restriction otherwise resulting from such a force.

As described above, any of the stabilizing connectors 100, 200, 300, 400, 500, 600, 700, and/or 800 described herein can be coupled to tubing or the like that can be used, for example, to transfer fluids and/or the like to or from the stabilizing connectors. As described above with reference to the stabilizing connectors 700 and/or 800, in some embodiments, the tubing (e.g., the tubing 752 and/or 852) can have an end portion (opposite the end coupled to the stabilizing connectors 700 and/or 800, respectively) that includes a coupler, attachment device, connector, and/or any other suitable engagement feature (e.g., the couplers 760 and/or 860, respectively). Moreover, the tubing 752 and/or 852 can include and/or can be coupled to a clamp or other suitable device configured to selectively control a flow of fluid through the tubing 752 and/or 852 (e.g., the clamps 770 and/or 870, respectively). While the tubing 752 and 852, the couplers 760 and 860, and the clamps 770 and 870 are particularly described above with reference to FIGS. 26 and 32, respectively, in other embodiments, a stabilizing connector and/or any other suitable device can include and/or can be coupled to tubing having any suitable coupler, clamp, and/or a combination thereof.

Figure 36:
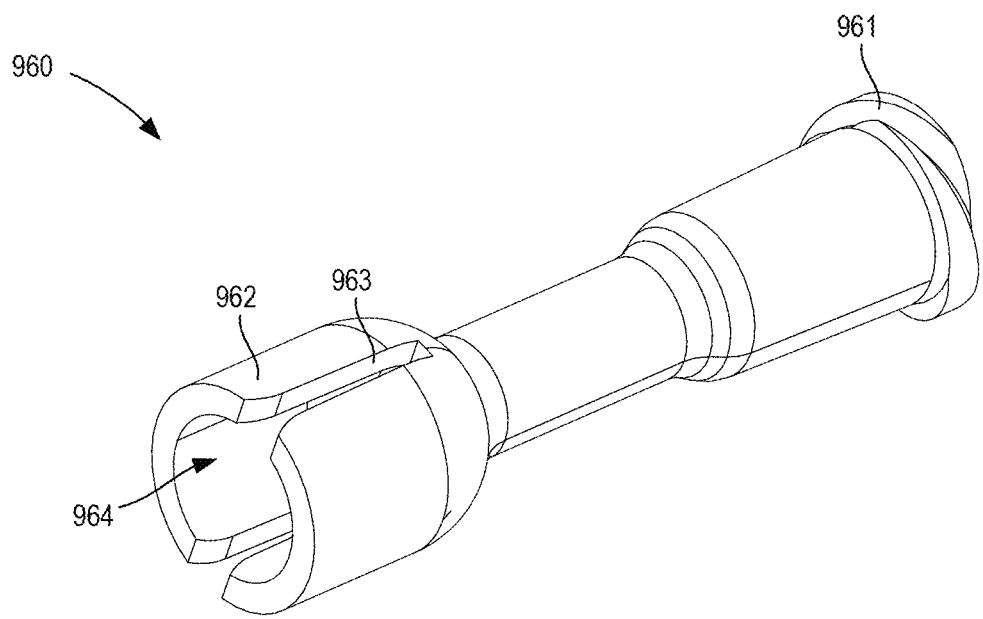
FIGS. 36 and 37 are a perspective view and a side view, respectively, of a coupler, according to an embodiment.
Figure 37:
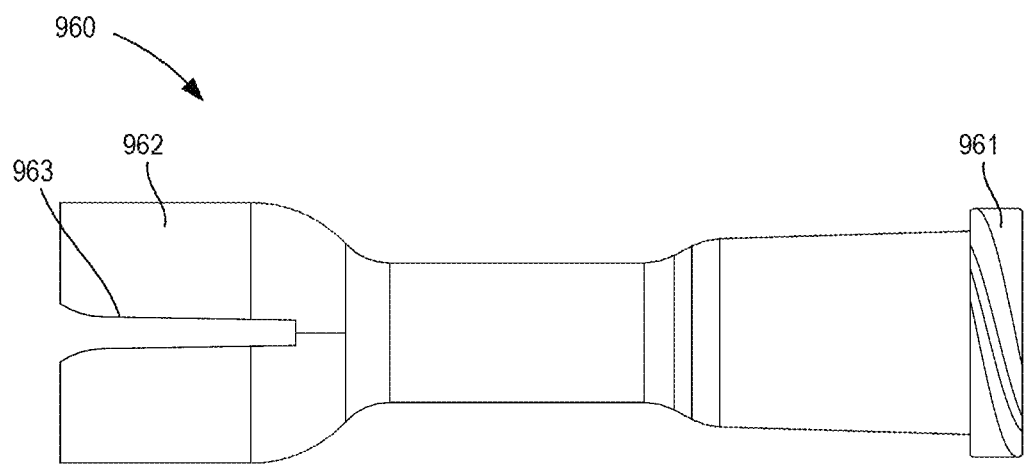

For example, FIGS. 36 and 37 are a perspective view and a side view, respectively, of at least a portion of a coupler 960, according to an embodiment. Any of stabilizing connectors 100, 200, 300, 400, 500, 600, 700, and/or 800 described herein can include tubing or the like (not shown), which in turn, includes and/or is connected to the coupler 960. The coupler 960 can be configured to couple one or more segments of tubing (e.g., of a tubing set) together and/or one or more segments of tubing to any suitable fluid source, fluid reservoir, fluid container, pump, syringe, and/or device. Moreover, in some instances, the coupler 960 can be physically and fluidically coupled to such a device or the like such that the coupler 960 and a lumen defined by the tubing places the device in fluid communication with the stabilizing connector to which the tubing is connected (e.g., any of the connectors 100, 200, 300, 400, 500, 600, 700, and/or 800, as described above).

The coupler 960 can be any suitable shape, size, and/or configuration. In some embodiments, the coupler 960 can be configured as an integrated or otherwise incorporated combination of one or more connectors or couplers (e.g., the couplers 760 and/or 860) and one or more tube clamps (e.g., the clamps 770 and/or 870) of a stabilization device, an extension set, and/or any other suitable device, such as those described herein. The coupler 960 can be arranged in any suitable manner to facilitate at least one of the functions of securing a connection between one or more tube segments and one or more connectors and/or any other suitable device. In some embodiments, the coupler 960 can be an integrated coupling and clamping device that can, for example, simplify manufacturing and/or assembly to thereby reduce operational cost. In some embodiments, the coupler 960 can be or include male or female luer locks, a female luer with an integrated tube clamp or tube clamping mechanism, and/or any other suitable coupler or fluid coupling.

The coupler 960 has a connector coupling interface or engagement portion 961 (also referred to herein as a "coupling portion" 961) and a clamping portion 962. The coupling portion 961 can be any suitable shape, size, and/or configuration. For example, in some embodiments, the coupling portion 961 can be, for example, a male or female luer lock, and/or any other suitable coupler. In some instances, the coupling portion 961 can be physically and fluidically coupled to any suitable medical device, fluid source, fluid reservoir, pump, syringe, and/or the like, such as any of those described herein. In some embodiments, the coupling portion 961 can be arranged and/or configured to accept a click to connect coupling (e.g., a click-lock-snap™ connection), a threaded coupling, a luer connection, and/or the like. In some embodiments, the coupling portion 961 can include, for example, a spin collar or the like and/or can otherwise be configured to form relatively easy, secure, and fluid tight connections. In some embodiments, the coupling portion 961 can be compatible with any suitable valve and/or seal (e.g., a valve used in a luer lock, a NFC valve, a split septum, a resealable valve or membrane, and/or the like), and/or can be a needleless or needle-free connector, an independent connector, and/or a swappable connector. In some embodiments, the coupling portion 961 can be configured to be compatible with any suitable known coupler or connector (e.g., such as those produced by Smiths, BD, Braun, ICU Medical, Terumo, etc.). As such, the coupling portion 961 can be coupled to any suitable device, mechanism, member, etc., which in turn, can be placed in fluid communication with a lumen of the tubing coupled to the clamping portion 962, as described in further detail herein.

The clamping portion 962 can be any suitable shape, size, and/or configuration. As shown in FIG. 36, the clamping portion 962 can define an inner volume, recess, port, opening, etc. (referred to herein as an "opening" 964) configured to receive at least an end portion of a tubing or the like (not shown). More particularly, the tubing can be inserted into and/or otherwise coupled to the clamping portion 962 such that a lumen of the tubing is placed in fluid communication with the coupling portion 961. As such, the coupler 960 can be configured to establish fluid communication between tubing physically and fluidically coupled to the clamping portion 962 and a device, mechanism, member, etc. physically and fluidically coupled to the coupling portion 961.

In addition, the clamping portion 962 can be and/or can include, for example, any suitable physical coupling or clamping device and/or mechanism such as a clamp, clip, slit, wedge, pinching device or mechanism, semi-ring (e.g., a two-sided open slide clamp, a slide clamp with loop, a two-sided closed slide clamp, a pinch clamp with a release lever, etc.), and/or any other suitable clamping feature. For example, in the embodiment shown in FIGS. 36 and 37, the clamping portion 962 defines a slot 963 along at least a portion of a length of the clamping portion 962 (e.g., substantially parallel to a longitudinal axis of at least the clamping portion 962).

The clamping portion 962 can be configured to selectively clamp, pinch, deform, occlude, and/or otherwise block at least a portion of the tubing and/or at least a portion of the lumen defined by the tubing. For example, in some instances, a user can manipulate at least a portion of the tubing coupled to the clamping portion 962 by inserting the portion of the tubing into the slot 963. Although not shown in FIGS. 36 and 37, the arrangement of the slot 963 can be such that a width of the slot 963 is less than a diameter of at least the portion of the tubing. As such, when the tubing is inserted into the slot 963, opposite surfaces of the clamping portion 962 that define the slot 963 can contact the portion of the tubing and can exert a force operable to bend, kink, pinch, clamp, and/or otherwise deform the portion of the tubing. In such instances, the deformation or the like of the tubing can be such that the lumen of the tubing is occluded, blocked, clamped or pinched closed, etc. Thus, the coupler 960 can be configured to function as a combination of a coupler (e.g., the couplers 760 and/or 860) and a clamp (770 and/or 870).

Figure 38:
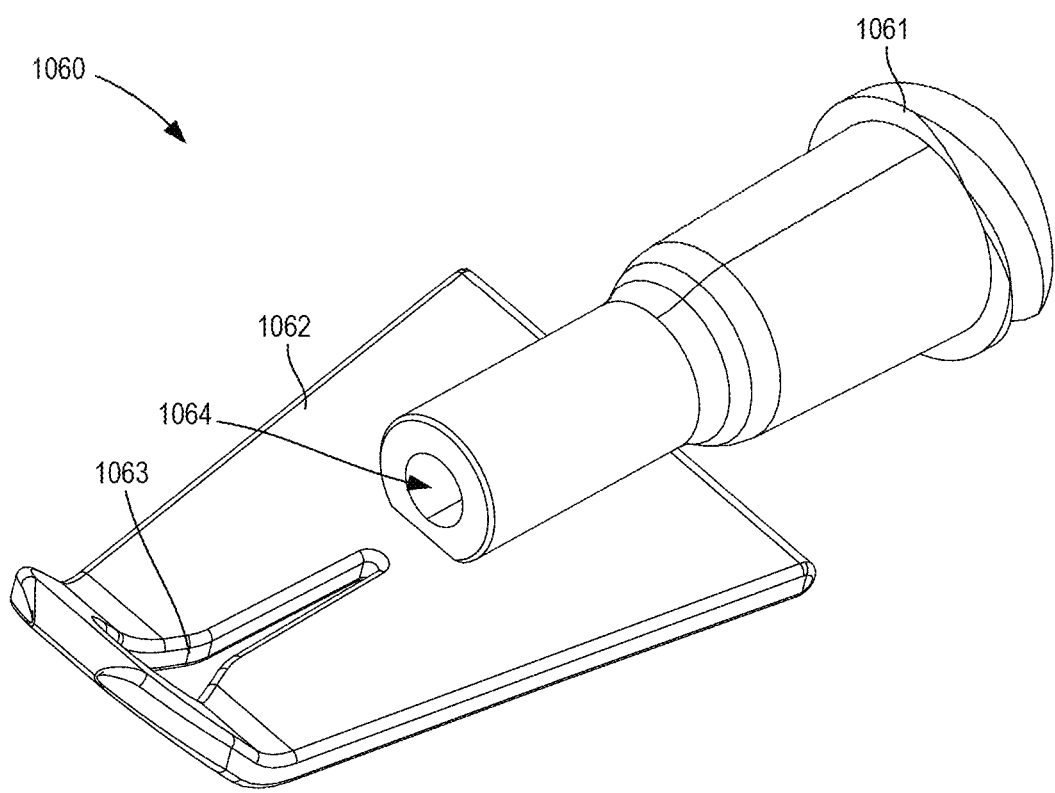
FIGS. 38 and 39 are a perspective view and a top view, respectively, of a coupler, according to an embodiment.
Figure 39:
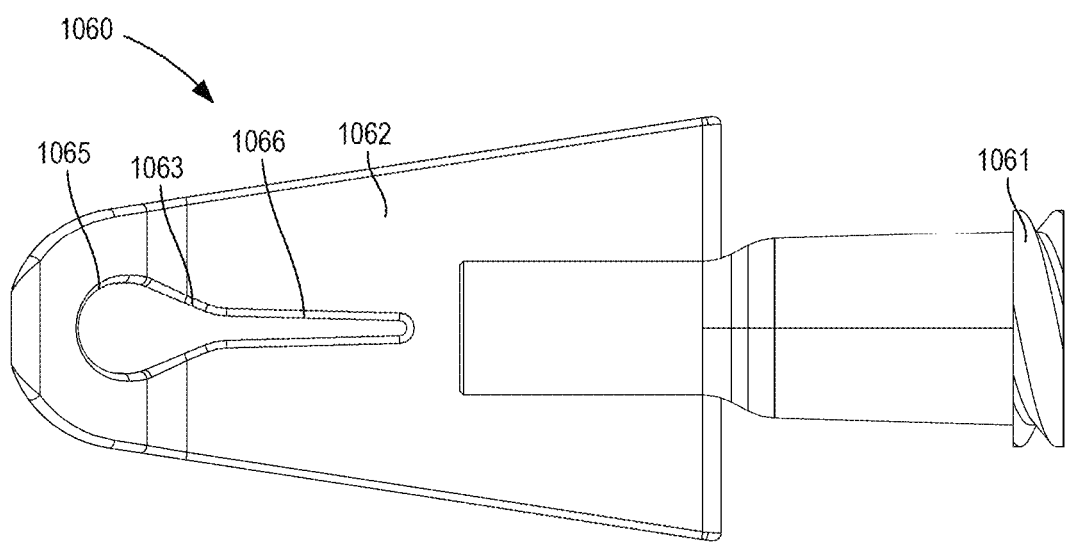

FIGS. 38 and 39 are a perspective view and a top view, respectively, of at least a portion of a coupler 1060, according to another embodiment. As described above, any of stabilizing connectors 100, 200, 300, 400, 500, 600, 700, and/or 800 can include tubing or the like (not shown), which in turn, includes and/or is coupled to the coupler 1060. The coupler 1060 can be configured to couple one or more segments of tubing (e.g., of a tubing set) together and/or one or more segments of tubing to any suitable fluid source, fluid reservoir, fluid container, pump, syringe, and/or device. Moreover, in some instances, the coupler 1060 can be physically and fluidically coupled to such a device or the like such that the coupler 1060 and a lumen defined by the tubing places the device in fluid communication with the stabilizing connector to which the tubing is connected (e.g., any of the connectors 100, 200, 300, 400, 500, 600, 700, and/or 800, as described above).

The coupler 1060 can be any suitable shape, size, and/or configuration. In some embodiments, the coupler 1060 can be configured as an integrated or otherwise incorporated combination of one or more connectors and one or more tube clamps of a stabilization device or stabilizing connector, extension set, and/or any other suitable device, as described above with reference to the coupler 960. In some embodiments, the coupler 1060 and/or at least portions or aspects thereof can be similar to and/or substantially the same as portions and/or aspects of the coupler 960, described above with reference to FIGS. 36 and 37. Accordingly, similar portions and/or aspects of the coupler 1060 are not described in further detail herein.

As shown in FIGS. 38 and 39, the coupler 1060 has a connector coupling interface or engagement portion 1061 (also referred to herein as "coupling portion" 1061) and a clamping portion 1062. The coupling portion 1061 can be any suitable shape, size, and/or configuration. For example, in some embodiments, the coupling portion 1061 can be, for example, a male or female luer lock, and/or any other suitable coupler. In some instances, the coupling portion 1061 can be physically and fluidically coupled to any suitable medical device, fluid source, fluid reservoir, pump, syringe, and/or the like, such as any of those described herein. In some embodiments, the coupling portion 1061 can be substantially similar in at least form and/or function to the coupling portion 961 of the coupler 960 and thus, is not described in further detail herein.

The clamping portion 1062 can be any suitable shape, size, and/or configuration. As shown in FIG. 38, the clamping portion 1062 can define an inner volume, recess, port, opening, etc. (referred to herein as an "opening" 1064) configured to receive at least an end portion of a tubing or the like (not shown). More particularly, the tubing can be inserted into and/or otherwise coupled to the clamping portion 1062 such that a lumen of the tubing is placed in fluid communication with the coupling portion 1061. As such, the coupler 1060 can be configured to establish fluid communication between tubing physically and fluidically coupled to the clamping portion 1062 and a device, mechanism, member, etc. physically and fluidically coupled to the coupling portion 1061.

In addition, the clamping portion 1062 can be and/or can include any suitable clamping mechanism and/or feature such as those described above with reference to the coupler 960. For example, in the embodiment shown in FIGS. 38 and 39, the clamping portion 1062 defines a slot 1063 along at least a portion of a length of the clamping portion 1062 (e.g., substantially parallel to a longitudinal axis of at least the clamping portion 1062). As shown in FIG. 39, the slot 1063 includes a first portion 1065 and a second portion 1066. In some embodiments, the first portion 1065 of the slot 1063 can have a diameter, size, and/or area that is larger than a diameter, size, and/or area of the second portion 1066 of the slot 1063. While the first portion 1065 and the second portion 1066 of the slot 1063 are particularly shown in FIG. 39, it should be understood that the slot 1063 and/or the clamping portion 1062 is shown by way of example only and not limitation. In other embodiments, the clamping portion 1062 can define a slot that has any suitable shape, size, and/or configuration and that is functionally similar to and/or substantially the same as the slot 1063.

As described above with reference to the coupler 960, the clamping portion 1062 can be configured to selectively clamp, pinch, deform, occlude, and/or otherwise block at least a portion of the tubing and/or at least a portion of the lumen defined by the tubing. For example, in some embodiments, an end portion of tubing can be inserted into the opening 1064 and/or otherwise coupled to the clamping portion 1062. Although not shown in FIGS. 38 and 39, a portion of the tubing can extend out of the opening 1064 and through at least a portion of the slot 1063. In some instances, a user can manipulate at least a portion of the tubing by placing and/or disposing the portion of the tubing in the first portion 1065 of the slot 1063 or the second portion 1066 of the slot 1063. As described above, in some embodiments, the first portion 1065 of the slot 1063 can have a larger diameter and/or size than the second portion 1066 of the slot and thus, when the portion of the tubing is disposed in and/or extends through the first portion 1065 of the slot 1063, the portion of the tubing can be in an undeformed or unclamped configuration in which the lumen of the tubing is substantially not clamped, not blocked, not occluded, etc., thereby allowing a flow of fluid therethrough.

Conversely, in some instances, a user can place and/or dispose the portion of the tubing in the second portion 1066 of the slot 1063 to clamp, pinch, close, block, and/or otherwise occlude the lumen of the tubing. For example, as described above with reference to the clamping portion 960, opposite surfaces of the clamping portion 1062 that define the second portion 1066 of the slot 1063 can contact the portion of the tubing and can exert a force operable to bend, kink, pinch, clamp, and/or otherwise deform the portion of the tubing such that the lumen of the tubing is occluded, blocked, clamped or pinched closed, etc. Thus, as described above with reference to the coupler 960, the coupler 1060 can be configured to function as a combination of a coupler (e.g., the couplers 760 and/or 860) and a clamp (770 and/or 870).

Figure 40:
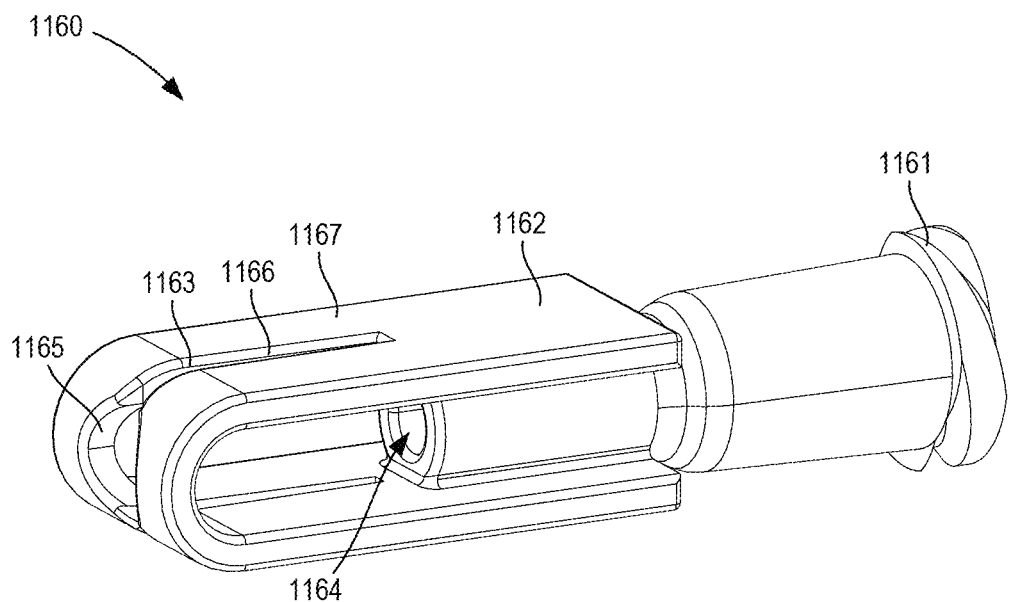
FIGS. 40 and 41 are a perspective view and a top view, respectively, of a coupler, according to an embodiment.
Figure 41:
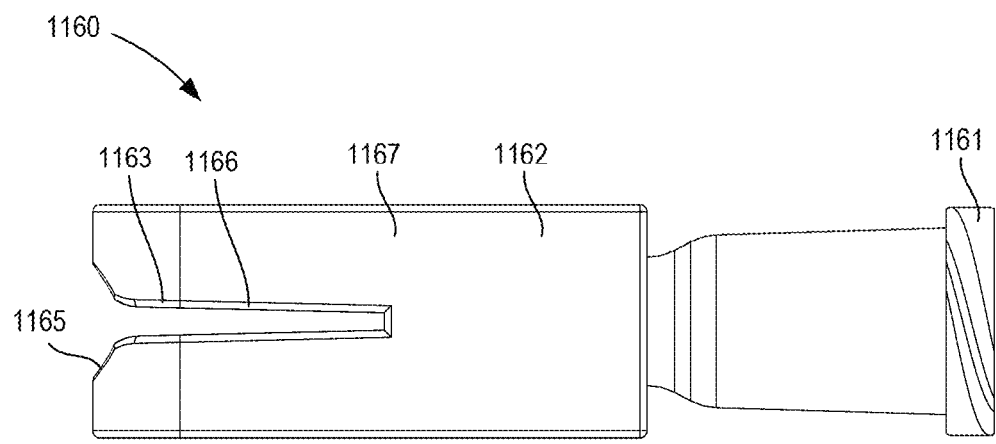

FIGS. 40 and 41 are a perspective view and a top view, respectively, of at least a portion of a coupler 1160, according to another embodiment. As described above, any of stabilizing connectors 100, 200, 300, 400, 500, 600, 700, and/or 800 can include tubing or the like (not shown), which in turn, includes and/or is coupled to the coupler 1160. The coupler 1160 can be configured to couple one or more segments of tubing (e.g., of a tubing set) together and/or one or more segments of tubing to any suitable fluid source, fluid reservoir, fluid container, pump, syringe, and/or device. Moreover, in some instances, the coupler 1160 can be physically and fluidically coupled to such a device or the like such that the coupler 1160 and a lumen defined by the tubing places the device in fluid communication with the stabilizing connector to which the tubing is connected (e.g., any of the connectors 100, 200, 300, 400, 500, 600, 700, and/or 800, as described above).

The coupler 1160 can be any suitable shape, size, and/or configuration. In some embodiments, the coupler 1160 can be configured as an integrated or otherwise incorporated combination of one or more connectors and one or more tube clamps of a stabilization device or stabilizing connector, extension set, and/or any other suitable device, as described above with reference to the coupler 1060. In some embodiments, the coupler 1160 and/or at least portions or aspects thereof can be similar to and/or substantially the same as portions and/or aspects of the coupler 1060, described above with reference to FIGS. 38 and 39. Accordingly, similar portions and/or aspects of the coupler 1160 are not described in further detail herein.

As shown in FIGS. 40 and 41, the coupler 1160 has a connector coupling interface or engagement portion 1161 (also referred to herein as "coupling portion" 1161) and a clamping portion 1162. The coupling portion 1161 can be any suitable shape, size, and/or configuration. For example, in some embodiments, the coupling portion 1161 can be, for example, a male or female luer lock, and/or any other suitable coupler. In some instances, the coupling portion 1161 can be physically and fluidically coupled to any suitable medical device, fluid source, fluid reservoir, pump, syringe, and/or the like, such as any of those described herein. In some embodiments, the coupling portion 1161 can be substantially similar in at least form and/or function to the coupling portion 1061 of the coupler 1060 and thus, is not described in further detail herein.

The clamping portion 1162 can be any suitable shape, size, and/or configuration. As shown in FIG. 40, the clamping portion 1162 can define an inner volume, recess, port, opening, etc. (referred to herein as an "opening" 1164) configured to receive at least an end portion of a tubing or the like (not shown), as described in detail above with reference to the clamping portion 1062. In addition, the clamping portion 1162 can be and/or can include any suitable clamping mechanism and/or feature such as those described above with reference to the couplers 960 and/or 1060. For example, in the embodiment shown in FIGS. 40 and 41, the clamping portion 1162 defines a slot 1163 having a first portion 1165 and a second portion 1166. In some embodiments, the first portion 1165 of the slot 1163 can have a diameter, size, and/or area that is larger than a diameter, size, and/or area of the second portion 1166 of the slot 1163, as described above with reference to the slot 1063.

The clamping portion 1162 can be substantially similar to the clamping portion 1062 described above with reference to FIGS. 38 and 39. As shown, the clamping portion 1162 can differ from the clamping portion 1062 by including a substantially U-shaped member 1167 with the first portion 1165 of the slot 1163 extending through an end portion or curved portion of the U-shaped member 1167 (see e.g., FIG. 40) and the second portion 1166 of the slot 1163 extending through each side (e.g., two opposing sides) of the U-shaped member 1167 (see e.g., FIG. 41). Thus, as described above with reference to the clamping portion 1062, the clamping portion 1162 can be configured to allow a portion of the tubing to extend through the first portion 1165 of the slot 1163 substantially without clamping or occluding the lumen of the tubing and can be configured to clamp, pinch, deform, and/or otherwise block at least a portion of the lumen when a portion of the tubing is placed and/or disposed in the second portion 1166 of the slot 1163. Accordingly, as described above with reference to the couplers 960 and/or 1060, the coupler 1160 can be configured to function as a combination of a coupler (e.g., the couplers 760 and/or 860) and a clamp (770 and/or 870).

Figure 42:
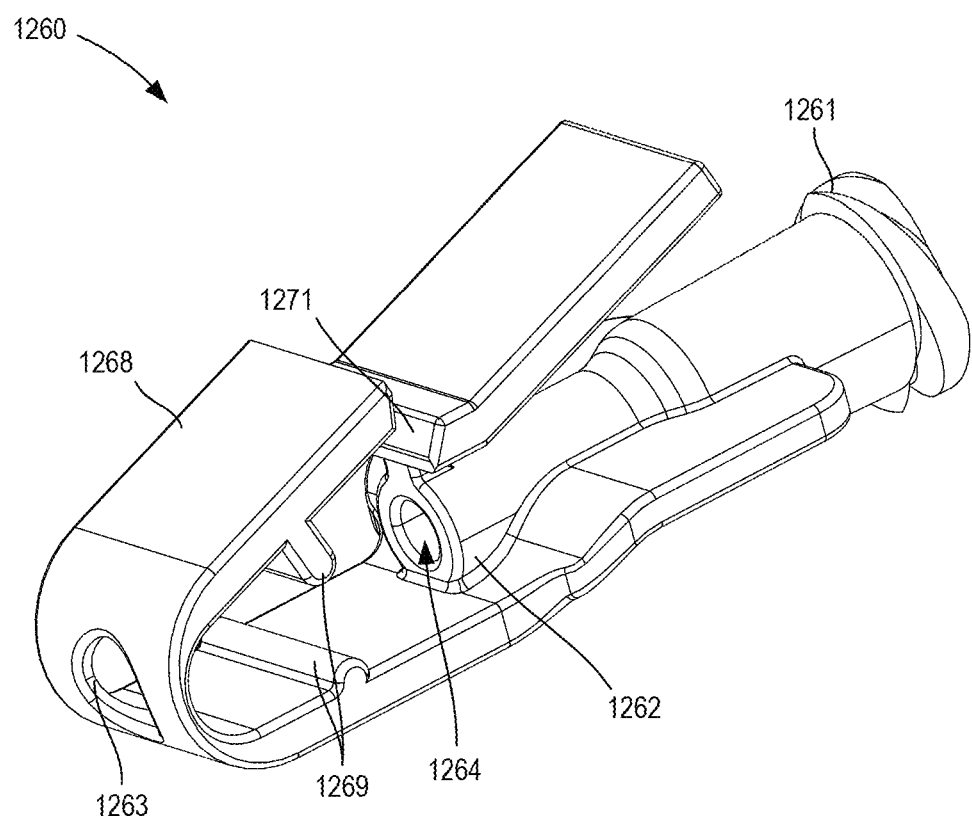
FIG. 42 is a perspective view of a coupler, according to an embodiment.
Figure 43:
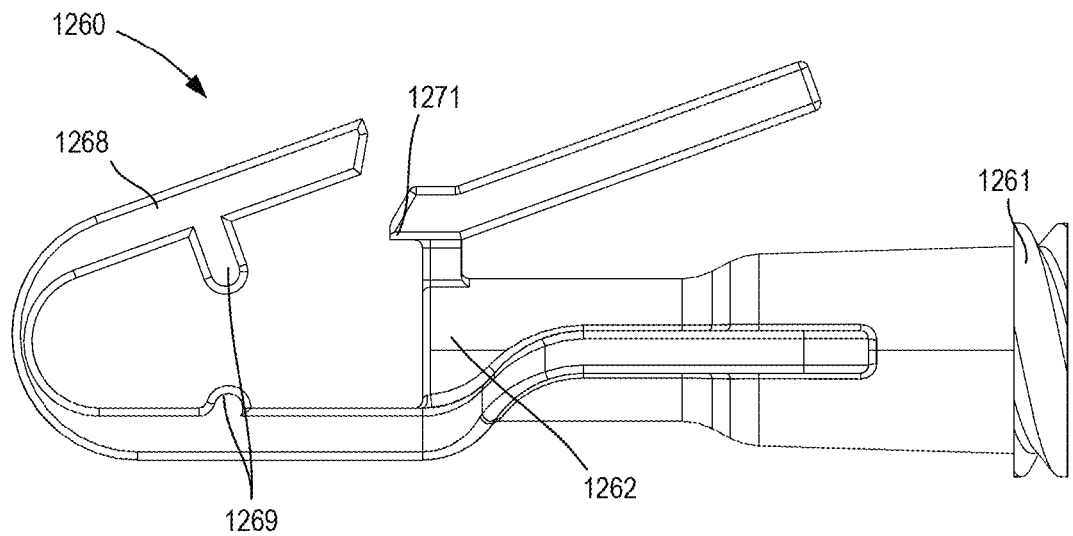
FIGS. 43 and 44 are side views of the coupler of FIG. 42 shown in a first configuration and a second configuration, respectively.
Figure 44:
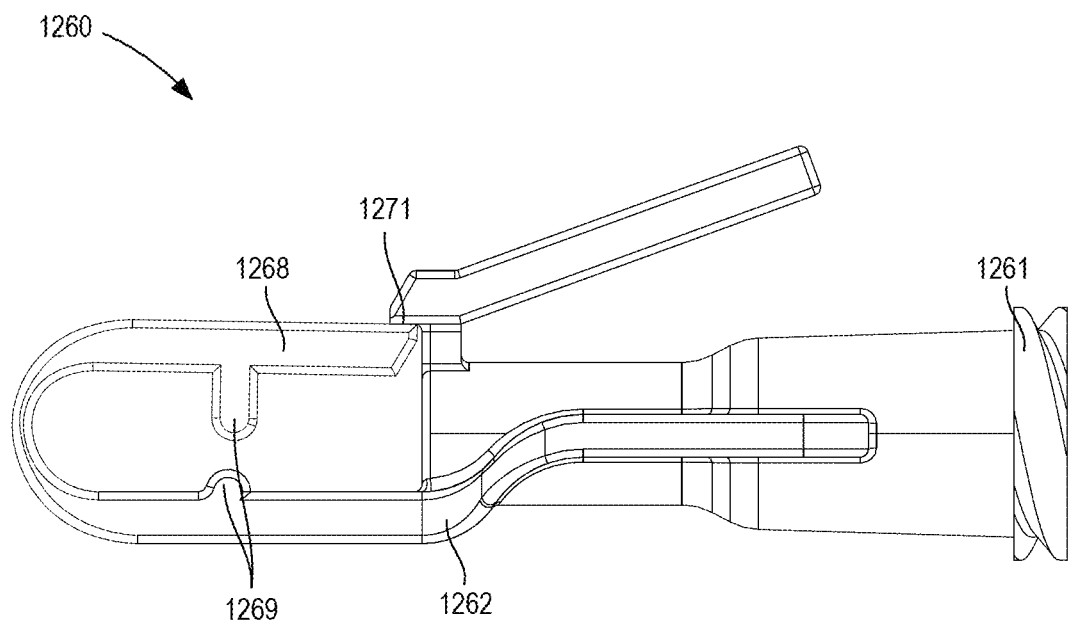

FIGS. 42-44 illustrate at least a portion of a coupler 1260, according to another embodiment. As described above, any of stabilizing connectors 100, 200, 300, 400, 500, 600, 700, and/or 800 can include tubing or the like (not shown), which in turn, includes and/or is coupled to the coupler 1260. The coupler 1260 can be configured to couple one or more segments of tubing (e.g., of a tubing set) together and/or one or more segments of tubing to any suitable fluid source, fluid reservoir, fluid container, pump, syringe, and/or device. Moreover, in some instances, the coupler 1260 can be physically and fluidically coupled to such a device or the like such that the coupler 1260 and a lumen defined by the tubing places the device in fluid communication with the stabilizing connector to which the tubing is connected (e.g., any of the connectors 100, 200, 300, 400, 500, 600, 700, and/or 800, as described above).

The coupler 1260 can be any suitable shape, size, and/or configuration. In some embodiments, the coupler 1260 can be configured as an integrated or otherwise incorporated combination of one or more connectors and one or more tube clamps of a stabilization device or stabilizing connector, extension set, and/or any other suitable device, as described above with reference to the couplers 960, 1060, and/or 1160. In some embodiments, the coupler 1260 and/or at least portions or aspects thereof can be similar to and/or substantially the same as portions and/or aspects of the couplers 960, 1060, and/or 1160, described in detail above. Accordingly, similar portions and/or aspects of the coupler 1260 are not described in further detail herein.

As shown in FIGS. 42-44, the coupler 1260 has a connector coupling interface or engagement portion 1261 (also referred to herein as "coupling portion" 1261) and a clamping portion 1262. The coupling portion 1261 can be any suitable shape, size, and/or configuration. For example, in some embodiments, the coupling portion 1261 can be, for example, a male or female luer lock, and/or any other suitable coupler. In some instances, the coupling portion 1261 can be physically and fluidically coupled to any suitable medical device, fluid source, fluid reservoir, pump, syringe, and/or the like, such as any of those described herein. In some embodiments, the coupling portion 1261 can be substantially similar in at least form and/or function to the coupling portions 961, 1061, and/or 1161 and thus, is not described in further detail herein.

The clamping portion 1262 can be any suitable shape, size, and/or configuration. As shown in FIG. 42, the clamping portion 1262 can define an inner volume, recess, port, opening, etc. (referred to herein as an "opening" 1264) configured to receive at least an end portion of a tubing or the like (not shown). In addition, the clamping portion 1262 can be and/or can include any suitable clamping mechanism and/or feature such as any of those described above with reference to the couplers 960, 1060, and/or 1160. For example, in the embodiment shown in FIGS. 42-44, the clamping portion 1262 includes a clip 1268 and/or any other suitable member configured to transition between a first state and/or configuration and a second state and/or configuration.

As shown in FIG. 42, the clip 1268 defines a slot 1263 or opening configured to receive a portion of the tubing. While the slots 963, 1063, and/or 1163 are described above as being configured to selectively engage a portion of the tubing to at least partially clamp the portion of the tubing, in the embodiment shown in FIGS. 42-44, the slot 1263 (or opening) can have a size and/or diameter sufficient to receive a portion of the tubing without clamping or otherwise blocking a lumen defined by the tubing. As such, the slot 1263 can receive a portion of the tubing and can act to direct, constrain, and/or at least partially limit a movement of the tubing relative to the clamping portion 1262.

The clip 1268 includes a set of protrusions extending from an inner surface of the clip 1268 and configured to selectively engage at least a portion of the tubing (not shown) that extends from the opening 1264 to the slot 1263. As shown in FIG. 43, the clip 1268 can be disposed in the first state and/or configuration in which a space defined between the protrusions 1269 is sufficient to receive the portion of the tubing without substantially clamping, bending, kinking, deforming, and/or otherwise engaging the tubing. Thus, when the clip 1268 is in the first state and/or configuration, the lumen of the tubing can be open or otherwise not blocked as a result of the portion of the tubing being clamped or the like.

Conversely, as shown in FIG. 44, a user can engage the clip 1268 to reduce the space defined between the protrusions 1269. For example, in some instances, the user can exert a force on a portion of the clip 1268 such that a first side of the clip 1268 is moved or brought into a closer proximity to a second side of the clip 1268, thereby reducing the space defined between the protrusions 1269. In some such instances, the transitioning of the clip 1268 from the first state and/or configuration to the second state and/or configuration is such that the protrusions 1269 engage opposite sides of the portion of the tubing, thereby clamping, pinching, deforming, bending, kinking, etc. the tubing, which in turn, can be sufficient to occlude, block, close, or clamp the lumen of the tubing. Moreover, as shown in FIGS. 43 and 44, the clamping portion 1262 can include a latch 1271 and/or the like configured to selectively engage a portion of the clip 1268 to maintain the clip 1268 in the second state and/or configuration until a user manipulates the clip 1268 in such a way that the clip 1268 is allowed to transition from the second state and/or configuration toward the first state and/or configuration. Accordingly, as described above with reference to the couplers 960, 1060, and/or 1160, the coupler 1260 can be configured to function as a combination of a coupler (e.g., the couplers 760 and/or 860) and a clamp (770 and/or 870).

While various embodiments have been described above, it should be understood that they have been presented by way of example only, and not limitation. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above. While the embodiments have been particularly shown and described, it will be understood that various changes in form and details may be made.

The specific configurations of the various components can also be varied. For example, the size and specific shape of the various components can be different from the embodiments shown, while still providing the functions as described herein. More specifically, the size and shape of the various components can be specifically selected for a desired or intended usage or to facilitate, simplify, and/or otherwise enable manufacturing and/or assembly. Thus, it should be understood that the size, shape, and/or arrangement of the embodiments and/or components thereof could be adapted for a given use unless the context explicitly states otherwise.

While the connectors 100, 200, 300, 400, 500, 600, 700, and/or 800 are described herein as being dual port adapters, connectors, and/or extension sets, in other embodiments, a stabilizing connector can be a single port connector, a dual port connector, a triple port connector, or a connector having four or more ports. For example, in some embodiments, any of the connectors 100, 200, 300, 400, 500, 600, 700, and/or 800 can include, for example, an additional port (e.g., similar to the port 250 or any other port described herein) extending from a side of the connector or connector portion. In some embodiments, the additional port (i.e., a third port) can be configured in a T-shaped arrangement, a Y-shaped arrangement, and/or any other suitable arrangement. In some embodiments, the third port can be disposed substantially perpendicularly relative to the bottom or second port. In other embodiments, the third port can be disposed at any suitable position along the connector portion. In such an arrangement, a user (e.g., a doctor, physician, surgeon, nurse, technician, etc.) can, for example, transfer multiple fluids and/or multiple volumes of the same fluid to or from the patient using, for example, the second port and the third port without accessing and/or using, for example, the proximal coupler. In other embodiments, a port of a connector can be coupled to a branched or bifurcated tubing that can place the tubing and the port in fluid communication with multiple fluid sources and/or reservoirs without including a multiple ports on or along the connector portion.

Any of the devices described herein can be included in a closed system that can be pre-assembled with any suitable access device or the like. For example, in some embodiments, the connectors 100, 200, 300, 400, 500, 600, 700, and/or 800 can be coupled to and and/or can include a VAD and a means for disposing at least a portion of the VAD within a desired portion of the patient. More particularly, in some embodiments, the VAD can be a peripheral IV catheter (PIV) or the like that can be coupled to and/or integrally formed with a stabilizing connector. In such embodiments, the stabilizing connector can be pre-assembled with the PIV and with a needle or trocar configured to initiate and/or facilitate a venipuncture event to dispose at least a portion of the PIV catheter in a desired or target vein of the patient. In some embodiments, such a stabilizing connector can be configured to be decoupled from the needle or trocar after the venipuncture event. In other words, after the portion of the PIV catheter is disposed in the desired and/or target vein, the needle or trocar can be removed from the stabilizing connector, leaving the portion of the PIV catheter in the portion of the vein. Moreover, after removing and/or decoupling the needle or trocar from the stabilizing connector, the user can secure the stabilizing connector to the patient, as described in detail above. Once secured, the stabilizing connector (e.g., the connectors 100, 200, 300, 400, 500, 600, 700, and/or 800) can be used in any suitable manner such as those described herein.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

What is claimed:

1. An apparatus, comprising:
a connector portion having a distal coupler and a proximal coupler and defining a lumen extending between the distal coupler and the proximal coupler, the proximal coupler including a fluid flow control device, the distal coupler configured to be coupled to a hub of an access device inserted, at least in part, into a patient at a predetermined angle relative to an insertion site of the patient, the lumen of the connector portion being placed in fluid communication with a lumen defined by the access device when the distal coupler is coupled to the hub; and
a stabilization portion integrally formed with at least a part of the connector portion, the stabilization portion configured to be in contact with the patient when the distal coupler is coupled to the hub of the access device to stabilize at least one of the connector portion or the access device, the connector portion being disposed at about the predetermined angle when the stabilization portion is in contact with the patient such that a common axis extends through the lumen defined by the connector portion and at least a portion of the lumen defined by the access device.

2. The apparatus of claim 1, wherein the predetermined angle is an insertion angle of at least a portion of the access device.

3. The apparatus of claim 1, wherein the lumen of the connector portion is a first lumen, the connector portion defines a second lumen in fluid communication with the first lumen, the second lumen is substantially perpendicular to the first lumen.

4. The apparatus of claim 1, wherein the lumen of the connector portion is a first lumen, the connector portion includes a port defining a second lumen in fluid communication with the first lumen, the port being disposed in a position along the connector portion that is adjacent to the proximal coupler.

5. The apparatus of claim 1, wherein the access device includes an intravenous catheter configured to be at least partially disposed within a vein of a patient.

6. The apparatus of claim 1, wherein the access device includes an intravenous catheter configured to be at least partially disposed within a vein of a patient,
the stabilization portion has a base surface that forms a recess, a portion of the base surface is configured to be in contact with the insertion site of the patient when the distal coupler is coupled to the hub of the access device such that the recess is aligned with the vein and spaced apart from the insertion site of the patient.

7. The apparatus of claim 6, wherein aligning the recess with the vein and spacing the recess apart from the insertion site reduces an amount of force exerted on the vein.

8. An apparatus, comprising:
a connector portion having a distal coupler and a proximal coupler and defining a lumen extending between the distal coupler and the proximal coupler, the distal coupler configured to be coupled to a hub of an access device at least partially inserted into a vein of a patient, the lumen of the connector portion being placed in fluid communication with a lumen defined by the access device when the distal coupler is coupled to the hub; and
a stabilization portion integrally formed with at least a part of the connector portion, the stabilization portion having a base surface, a portion of the base surface configured to be in contact with the patient when the distal coupler is coupled to the hub of the access device such that the stabilization portion stabilizes at least one of the connector portion or the access device and a common axis extends through the lumen defined by the connector portion and at least a portion of the lumen defined by the access device, the base surface forming a recess configured to be aligned with the vein and spaced apart from the patient when the portion of the base surface is in contact with the patient, wherein the base surface has a proximal edge and a distal edge, the recess extends between the proximal edge and the distal edge.

9. The apparatus of claim 8, wherein a portion of the access device is inserted into the vein at a predetermined angle relative to an insertion site of the patient, the stabilization portion configured to place the connector portion at about the predetermined angle relative to the insertion site when the distal coupler is coupled to the hub of the access device and the portion of the base surface is in contact with the patient.

10. The apparatus of claim 8, wherein the access device includes an intravenous catheter.

11. The apparatus of claim 8, wherein the proximal coupler is configured to be coupled to a fluid transfer device.

12. The apparatus of claim 11, wherein the proximal coupler includes a needle free connector (NFC) valve, the NFC valve configured to transition from a closed configuration to an open configuration in response to the fluid transfer device being coupled to the proximal coupler.

13. An apparatus, comprising:
a connector portion having a distal coupler and a proximal coupler and defining a lumen extending between the distal coupler and the proximal coupler, the distal coupler configured to be coupled to a hub of an access device at least partially inserted into a patient such that the lumen of the connector portion is in fluid communication with a lumen defined by the access device; and
a stabilization portion integrally formed with at least a part of the connector portion, the stabilization portion having a base surface, a portion of the base surface configured to be in contact with the patient when the distal coupler is coupled to the hub of the access device to stabilize at least one of the connector portion or the access device, the base surface forming a recess configured to be spaced apart from the patient when the portion of the base surface is in contact with the patient,
the connector portion being disposed at a predetermined angle when the distal coupler is coupled to the hub of the access device and the portion of the base surface is in contact with the patient such that a common axis extends through the lumen defined by the connector portion and at least a portion of the lumen defined by the access device, wherein the base surface has a proximal edge and a distal edge, the recess extends between the proximal edge and the distal edge.

14. The apparatus of claim 13, wherein the access device is a peripheral intravenous catheter configured to be at least partially disposed in a vein of the patient.

15. The apparatus of claim 14, wherein the recess is configured to be aligned with the vein and spaced apart from the patient when the portion of the base surface is in contact with the patient to reduce an amount of force otherwise exerted on the vein by the base surface.

16. The apparatus of claim 13, wherein the lumen of the connector portion is a first lumen, the connector portion includes a port defining a second lumen in fluid communication with the first lumen,
the port is disposed between the base surface of the stabilization portion and the proximal coupler.

17. The apparatus of claim 13, wherein the proximal coupler is configured to be coupled to a fluid transfer device.

18. The apparatus of claim 17, wherein the proximal coupler includes a needle free connector (NFC) valve, the NFC valve configured to transition from a closed configuration to an open configuration in response to the fluid transfer device being coupled to the proximal coupler.

* * * * *